(12) United States Patent
Buchstaller et al.

(10) Patent No.: US 7,691,886 B2
(45) Date of Patent: Apr. 6, 2010

(54) BENZIMIDAZOLE DERIVATIVES AS RAF KINASE INHIBITORS

(75) Inventors: Hans-Peter Buchstaller, Griesheim (DE); Dirk Finsinger, Darmstadt (DE); Matthias Wiesner, Seeheim-Jugenheim (DE); Lars Thore Burgdorf, Frankfurt (DE); Christiane Amendt, Darmstadt (DE); Matthias Grell, Darmstadt (DE); Christian Sirrenberg, Darmstadt (DE); Frank Zenke, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/564,185

(22) PCT Filed: Jun. 15, 2004

(86) PCT No.: PCT/EP2004/006419

§ 371 (c)(1),
(2), (4) Date: Aug. 7, 2006

(87) PCT Pub. No.: WO2005/004864

PCT Pub. Date: Jan. 20, 2005

(65) Prior Publication Data

US 2007/0010560 A1 Jan. 11, 2007

(30) Foreign Application Priority Data

Jul. 11, 2003 (EP) .................. 03015582

(51) Int. Cl.
*C07D 401/00* (2006.01)
*A01N 43/64* (2006.01)

(52) U.S. Cl. .................. 514/359; 546/273.4

(58) Field of Classification Search .......... None
See application file for complete search history.

(56) References Cited

U.S. PATENT DOCUMENTS 4,002,623 A 1/1977 Kadin 4,011,236 A 3/1977 Grier
2004/0110808 A1* 6/2004 Strobel et al. ............... 514/367
2007/0093532 A1 4/2007 Buchstaller et al.

FOREIGN PATENT DOCUMENTS

| WO | WO 00/27819 | 5/2000 |
| WO | WO 01/21160 A2 | 3/2001 |
| WO | WO 02/44156 A2 | 6/2002 |
| WO | WO 02/46171 A2 | 6/2002 |
| WO | WO 03/030902 A1 | 4/2003 |
| WO | WO 2004/001059 A2 | 12/2003 |
| WO | WO 2004/014369 A1 | 2/2004 |

OTHER PUBLICATIONS

Huang et al., "Sythesis and biological study of 2-amino-4-aryl-5-chloropyrimidine analogues as inhibitors of VEGFR-2 and cyclin dependent kinase 1", Bioorg & Med Chem Lett, 17, 2007, 2179-2183.*
Wickens et al., "SAR of a novel anthranilamide like series of VEGFR-2 multi protein kinase inhibitors for the treatment fo cancer", Bioorg Med Chem Lett, 17, 2007, 4378-4381.*
Khire et al., "Omega carboxypyridyl substituted ureas as Raf-kinase inhibitors: SAR of the amide subtituent", Bioorg Med Chem Lett, 14, 2004, 783-786.*
http://en.wikipedia.org/wiki/Kinase.*
Hacks Chemical Dictionary, Fourth Edition, Julius Grant, 1972, p. 203.*
Newman et al., DDT vol. 8, Oct. 2003, p. 898-90.*
Chawla et al., CRIPS vol. 5, No. 1, Jan.-Mar. 2004, p. 9-12.*
Arbiser, The Journal of Clinical Investigation, 117, 10, 2762-2765.*
Fischer et al., Cancer Treatment Reviews 2007, 33, 391-406.*
Madhusudan et al., Clinical Biochemistry, 2004, 37, 618-635.*
Collins, Expert Opinion Investig Drugs (2007), 16(11), p. 1743-1751.*

* cited by examiner

*Primary Examiner*—Golam M. M. Shameem
*Assistant Examiner*—Sun Jae Y Loewe
(74) *Attorney, Agent, or Firm*—Arent Fox LLP

(57) ABSTRACT

The present invention relates to benzimidazole derivatives of formula I, the use of the compounds of formula I as inhibitors of one or more kinases, the use of the compounds of formula I for the manufacture of a pharmaceutical compositions and methods of treatment, comprising administering said pharmaceutical compositions to patients.

9 Claims, No Drawings

BENZIMIDAZOLE DERIVATIVES AS RAF KINASE INHIBITORS

The present application claims priority to International Application No. PCT/EP2004/006419 filed Jun. 15, 2004, which claims priority to European Patent Application No. 03015582.4 filed Jul. 11, 2003. The contents of both applications are expressly incorporated herein by reference in their entireties.

The present invention relates to benzimidazole derivatives, benzimidazole derivatives as medicaments, benzimidazole derivatives as inhibitors of one or more kinases, preferably of raf-kinase, the use of benzimidazole derivatives for the manufacture of a pharmaceutical, a method for producing a pharmaceutical composition containing said benzimidazole derivatives, the pharmaceutical composition obtainable by said method and a method of treatment, comprising administering said pharmaceutical composition.

Protein phosphorylation is a fundamental process for the regulation of cellular functions. The coordinated action of both protein kinases and phosphatases controls the levels of phosphorylation and, hence, the activity of specific target proteins. One of the predominant roles of protein phosphorylation is in signal transduction, where extracellular signals are amplified and propagated by a cascade of protein phosphorylation and dephosphorylation events, e.g. in the $p21^{ras}/$raf pathway.

The $p21^{ras}$ gene was discovered as an oncogene of the Harvey (rasH) and Kirsten (rask) rat sarcoma viruses. In humans, characteristic mutations in the cellular ras gene (c-ras) have been associated with many different types of cancers. These mutant alleles, which render Ras constitutively active, have been shown to transform cells, such as the murine cell line NIH 3T3, in culture.

The $p21^{ras}$ oncogene is a major contributor to the development and progression of human solid cancers and is mutated in 30% of all human cancers (Bolton et al. (1994) Ann. Rep. Med. Chem., 29, 165-74; Bos. (1989) Cancer Res., 49, 4682-9). In its normal, unmutated form, the ras protein is a key element of the signal transduction cascade directed by growth factor receptors in almost all tissues (Avruch et al. (1994) Trends Biochem. Sci., 19, 279-83).

Biochemically, ras is a guanine nucleotide binding protein, and cycling between a GTP-bound activated and a GDP-bound resting form is strictly controlled by ras endogenous GTPase activity and other regulatory proteins. The ras gene product binds to guanine triphosphate (GTP) and guanine diphosphate (GDP) and hydrolyzes GTP to GDP. It is the GTP-bound state of Ras that is active. In the ras mutants in cancer cells, the endogenous GTPase activity is alleviated and, therefore, the protein delivers constitutive growth signals to downstream effectors such as the enzyme raf kinase. This leads to the cancerous growth of the cells which carry these mutants (Magnuson et al. (1994) Semin. Cancer Biol., 5, 247-53). The ras proto-oncogene requires a functionally intact c-rafl proto-oncogene in order to transduce growth and differentiation signals initiated by receptor and non-receptor tyrosine kinases in higher eukaryotes.

Activated Ras is necessary for the activation of the c-rafl proto-oncogene, but the biochemical steps through which Ras activates the Raf-1 protein (Ser/Thr) kinase are now well characterized. It has been shown that inhibiting the effect of active ras by inhibiting the raf kinase signaling pathway by administration of deactivating antibodies to raf kinase or by co-expression of dominant negative raf kinase or dominant negative MEK (MAPKK), the substrate of raf kinase, leads to the reversion of transformed cells to the normal growth phenotype see: Daum et al. (1994) Trends Biochem. Sci., 19, 474-80; Fridman et al. (1994) J. Biol. Chem., 269, 30105-8. Kolch et al. (1991) Nature, 349, 426-28) and for review Weinstein-Oppenheimer et al. Pharm. & Therap. (2000), 88, 229-279.

Similarly, inhibition of raf kinase (by antisense oligodeoxynucleotides) has been correlated in vitro and in vivo with inhibition of the growth of a variety of human tumor types (Monia et al., Nat. Med. 1996, 2, 668-75).

Raf serine- and threonine-specific protein kinases are cytosolic enzymes that stimulate cell growth in a variety of cell systems (Rapp, U. R., et al. (1988) in The oncogene handbook; T. Curran, E. P. Reddy, and A. Skalka (ed.) Elsevier Science Publishers; The Netherlands, pp. 213-253; Rapp, U. R., et al. (1988) Cold Spring Harbor Sym. Quant. Biol. 53:173-184; Rapp, U. R., et al. (1990) Inv Curr. Top. Microbiol. Amunol. Potter and Melchers (eds), Berlin, Springer-Verlag 166:129-139).

Three isozymes have been characterized:
c-Raf (Raf-1) (Bonner, T. I., et al. (1986) Nucleic Acids Res. 14:1009-1015). A-Raf (Beck, T. W., et al. (1987) Nucleic Acids Res. 15:595-609), and B-Raf (Qkawa, S., et al. (1998) Mol. Cell. Biol. 8:2651-2654; Sithanandam, G. et al. (1990) Oncogene:1775). These enzymes differ in their expression in various tissues. Raf-1 is expressed in all organs and in all cell lines that have been examined, and A- and B-Raf are expressed in urogenital and brain tissues, respectively (Storm, S. M. (1990) Oncogene 5:345-351).

Raf genes are proto-oncogenes: they can initiate malignant transformation of cells when expressed in specifically altered forms. Genetic changes that lead to oncogenic activation generate a constitutively active protein kinase by removal or interference with an N-terminal negative regulatory domain of the protein (Heidecker, G., et al. (1990) Mol. Cell. Biol. 10:2503-2512; Rapp, U. R., et al. (1987) in Oncogenes and cancer S. A. Aaronson, J. Bishop, T. Sugimura, M. Terada, K. Toyoshima, and P. K. Vogt (ed). Japan Scientific Press, Tokyo). Microinjection into NIH 3T3 cells of oncogenically activated but not wild-type versions of the Raf-protein prepared with Escherichia coli expression vectors results in morphological transformation and stimulates DNA synthesis (Rapp, U. R., et al. (1987) in Oncogenes and cancer; S. A. Aaronson, J. Bishop, T. Sugimura, M. Terada, K. Toyoshima, and P. K. Vogt (ed.) Japan Scientific Press, Tokyo; Smith, M. R., et al (1990) Mol. Cell. Biol. 10:3828-3833). Activating mutants of B-Raf have been identified in a wide range of human cancers e.g. colon, ovarien, melanomas and sarcomas (Davies, H., et al. (2002), Nature 417 949-945. Published online Jun. 9, 2002, 10.1038/nature00766). The preponderant mutation is a single phosphomimetic substitution in the kinase activation domain (V599E), leading to constitutive kinase activity and transformation of NIH3T3 cells.

Thus, activated Raf-1 is an intracellular activator of cell growth. Raf-1 protein serine kinase in a candidate downstream effector of mitogen signal transduction, since Raf oncogenes overcome growth arrest resulting from a block of cellular ras activity due either to a cellular mutation (ras revertant cells) or microinjection of anti-ras antibodies (Rapp, U. R., et al. (1988) in The Oncogene Handbook, T. Curran, E. P. Reddy, and A. Skalka (ed.), Elsevier Science Publishers; The Netherlands, pp. 213-253; Smith, M. R., et al. (1986) Nature (London) 320:540-543).

c-Raf function is required for transformation by a variety of membrane-bound oncogenes and for growth stimulation by mitogens contained in serums (Smith, M. R., et al. (1986) Nature (London) 320:540-543). Raf-1 protein serine kinase activity is regulated by mitogens via phosphorylation (Morrison, D. K., et al. (1989) Cell 58:648-657), which also effects sub cellular distribution (Olah, Z., et al. (1991) Exp. Brain Res. 84:403; Rapp, U. R., et al. (1988) Cold Spring Harbor Sym. Quant. Biol. 53:173-184. Raf-1 activating growth factors include platelet-derived growth factor (PDGF) (Morrison, D. K., et al. (1988) Proc. Natl. Acad. Sci. USA 85:8855-8859), colony-stimulating factor (Baccarini, M., et al. (1990) EMBO J. 9:3649-3657), insulin (Blackshear, P. J., et al. (1990) J. Biol. Chem. 265:12115-12118), epidermal growth factor (EGF) (Morrison, R. K., et al. (1988) Proc. Natl. Acad. Sci. USA 85:8855-8859), interleukin 2 (Turner, B. C., et al (1991) Proc. Natl. Acad. Sci. USA 88:1227), and interleukin 3 and granulocytemacrophage colony-stimulating factor (Carroll, M. P., et al (1990) J. Biol. Chem. 265:19812-19817).

Upon mitogen treatment of cells, the transiently activated Raf-1 protein serine kinase translocates to the perinuclear area and the nucleus (Olah, Z., et al. (1991) Exp. Brain Res. 84:403; Rapp, U. R., et al. (1988) Cold Spring Habor Sym. Quant. Biol. 53:173-184). Cells containing activated Raf are altered in their pattern of gene expression (Heidecker, G., et al. (1989) in Genes and signal transduction in multistage carcinogenesis, N. Colburn (ed.), Marcel Dekker, Inc., New York, pp. 339-374), and Raf oncogenes activate transcription from Ap-I/PEA3-dependent promoters in transient transfection assays (Jamal, S., et al (1990) Science 344:463-466; Kaibuchi, K., et al (1989) J. Biol. Chem. 264:20855-20858; Wasylyk, C., et al. (1989) Mol. Cell. Biol. 9:2247-2250).

There are at least two independent pathways for Raf-1 activation by extracellular mitogens: one involving protein kinase C (KC) and a second initiated by protein tyrosine kinases (Blackshear, P. J., et al. (1990) J. Biol. Chem. 265: 12131-12134; Kovacina, K. S., et al (1990) J. Biol. Chem. 265:12115-12118; Morrison, D. K., et al. (1988) Proc. Natl. Acad. Sci. USA 85:8855-8859; Siegel, J. N., et al (1990) J. Biol. Chem. 265:18472-18480; Turner, B. C., et al (1991) Proc. Natl. Acad. Sci. USA 88:1227). In either case, activation involves Raf-1 protein phosphorylation. Raf-1 phosphorylation may be a consequence of a kinase cascade amplified by autophosphorylation or may be caused entirely by autophosphorylation initiated by binding of a putative activating ligand to the Raf-1 regulatory domain, analogous to PKC activation by diacylglycerol (Nishizuka, Y. (1986) Science 233:305-312).

The process of angiogenesis is the development of new blood vessels, generally capillaries, from pre-existing vasculature. Angiogenesis is defined as involving one or more of the following steps: (i) activation of endothelial cells; (ii) increased vascular permeability; (iii) subsequent dissolution of the basement membrane and extravasation of plasma components leading to formation of a provisional fibrin gel extracellular matrix; (iv) proliferation and mobilization of endothelial cells; (v) reorganization of mobilized endothelial cells to form functional capillaries; (vi) capillary loop formation; and (vii) deposition of basement membrane and recruitment of perivascular cells to newly formed vessels.

Normal angiogenesis is activated during tissue growth, from embryonic development through maturity, and then enters a period of relative quiescence during adulthood.

Normal angiogensesis is also activated during wound healing, and at certain stages of the female reproductive cycle. Inappropriate or pathological angiogenesis has been associated with several disease states including various retinopathies; ischemic disease; atherosclerosis; chronic inflammatory disorders; rheumatoid arthritis, and cancer. The role of angiogenesis in disease states is discussed, for instance, in Fan et al, Trends in Pharmacol Sci. 16:54 66; Shawver et al, DOT Vol. 2, No. 2 Feb. 1997; Folkmann, 1995, Nature Medicine 1:27-31.

In cancer the growth of solid tumors has been shown to be angiogenesis dependent. (See Folkmann, J., J. Nat'l. Cancer Inst., 1990, 82, 4-6.) Consequently, the targeting of pro-angiogenic pathways is a strategy being widely pursued in order to provide new therapeutics in these areas of great, unmet medical need.

Raf is involved in angiogenic processes. Endothelial growth factors (e.g. vascular endothelial growth factor VEGF) activates receptor tyrosine kinases (e.g. VEGFR-2) and signal through the Ras/Raf/Mek/Erk kinase cascade. Activation of VEGFR-2 by VEGF is a critical step in the signal transduction pathway that initiates tumor angiogenesis. VEGF expression may be constitutive to tumor cells and can also be upregulated in response to certain stimuli. One such stimuli is hypoxia, where VEGF expression is upregulated in both tumor and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signaling proteins downstream of VEGFR-2 leading ultimately to initiation of angiogenesis (McMahon, G., The Oncologist, Vol. 5, No. 90001, 3-10, April 2000).

Mice with a targeted disruption in the Braf gene die of vascular defects during development (Wojnowski, L. et al. 1997, Nature genetics 16, page 293-296). These mice show defects in the formation of the vascular system and in angiogenesis e.g. enlarged blood vessels and increased apoptotic death of differentiated endothelial cells.

For the identification of a signal transduction pathway and the detection of cross talks with other signaling pathways suitable models or model systems have been generated by various scientists, for example cell culture models (e.g. Khwaja et al., EMBO, 1997, 16, 2783-93) and transgenic animal models (e.g. White et al., Oncogene, 2001, 20, 7064-7072). For the examination of particular steps in the signal transduction cascade, interfering compounds can be used for signal modulation (e.g. Stephens et al., Biochemical J., 2000, 351, 95-105). The compounds according to the invention may also be useful as reagents for the examination of kinase dependent signal transduction pathways in animal and/or cell culture models or any of the clinical disorders listed throughout this application.

The measurement of kinase activity is a well known technique feasible for each person skilled in the art. Generic test systems for kinase activity detection with substrates, for example histone (e.g. Alessi et al., FEBS Lett. 1996, 399, 3, page 333-8) or myelin basic protein are well described in the literature (e.g. Campos-González, R. and Glenney, Jr., J. R. 1992 *J. Biol. Chem.* 267, Page 14535).

For the identification of kinase inhibitors various assay systems are available (see for example Walters et al., Nature Drug Discovery 2003, 2; page 259-266). For example, in scintillation proximity assays (e.g. Sorg et al., J. of. Biomolecular Screening, 2002, 7, 11-19) or flashplate assays the radioactive phosphorylation of a protein or peptide as substrate with γATP can be measured. In the presence of an inhibitory compound no signal or a decreased radioactive signal is detectable. Furthermore homogeneous time-resolved fluorescence resonance energy transfer (HTR-FRET), and fluorescence polarization (FP) technologies are useful for assay methods (for example Sills et al., J. of Biomolecular Screening, 2002, 191-214).

Other non-radioactive ELISA based assay methods use specific phospho-antibodies (AB). The phospho-AB binds only the phosphorylated substrate. This binding is detectable with a secondary peroxidase conjugated antibody, measured for example by chemiluminescence (for example Ross et al., Biochem. J., 2002, 366, 977-981).

The present invention provides compounds generally described as benzimidazole derivatives, including both aryl and/or heteroaryl derivatives which are preferably kinase inhibitors and more preferably inhibitors of the enzyme raf kinase. Since the enzyme is a downstream effector of $p21^{ras}$, the inhibitors are useful in pharmaceutical compositions for human or veterinary use where inhibition of one or more kinase pathways, preferably of the raf kinase pathway, is indicated, e.g., in the treatment of tumors and/or cancerous cell growth mediated by kinases, preferably by raf kinase. In particular, the compounds are useful in the treatment of human or animal solid cancers, e.g. murine cancer, since the progression of these cancers is dependent upon the ras protein signal transduction cascade and therefore susceptible to treatment by interruption of the cascade, i.e., by inhibiting one or more kinases, preferably by inhibiting raf kinase. Accordingly, the compound of Formula I or a pharmaceutically acceptable salt thereof is administered for the treatment of diseases mediated by one or more kinase pathways, preferably by the raf kinase pathway, especially cancers, including solid cancers, such as, for example, carcinomas (e.g., of the lungs, pancreas, thyroid, bladder or colon), myeloid disorders (e.g., myeloid leukemia) or adenomas (e.g., villous colon adenoma), pathological angiogenesis and metastatic cell migration. Furthermore the compounds are useful in the treatment of complement activation dependent chronic inflammation (Niculescu et al. (2002) Immunol. Res., 24:191-199) and HIV-1 (human immunodeficiency virus type1) induced immunodeficiency (Popik et al. (1998) J Virol, 72: 6406-6413).

Therefore, subject of the present invention are compounds of formula I

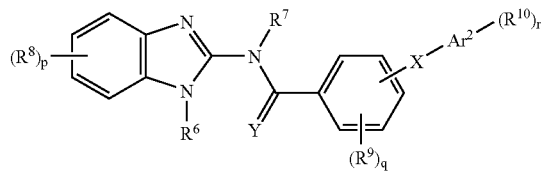

wherein
$R^6$, $R^7$ are independently from one another H, A or $SO_2A$,
A is independently selected from the group consisting of alkyl, alkenyl, cycloalkyl, alkylenecycloalkyl, alkoxy and alkoxyalkyl,
$R^8$, $R^9$ and $R^{10}$ are independently selected from a group consisting of H, A, cycloalkyl comprising 3 to 7 carbon atoms, Hal, $CH_2Hal$, $CH(Hal)_2$, $C(Hal)_3$, $NO_2$, $(CH_2)_nCN$, $(CH_2)_nNR^{11}R^{12}$, $(CH_2)_nOR^{11}$, $(CH_2)_nO(CH_2)_kNR^{11}R^{12}$, $(CH_2)_nCOOR^{12}$, $(CH_2)_nCONR^{11}R^{12}$, $(CH_2)_nNR^{11}COR^{12}$, $(CH_2)_nNR^{11}CONR^{11}R^{12}$, $(CH_2)_nNR^{11}SO_2A$, $(CH_2)_nSO_2NR^{11}R^{12}$, $(CH_2)_nS(O)_uR^{13}$, $(CH_2)_nOC(O)R^{13}$, $(CH_2)_nCOR^{13}$, $(CH_2)_nSR^{11}$, $CH=N-OA$, $CH_2CH=N-OA$, $(CH_2)_nNHOA$, $(CH_2)_nCH=N-R^{11}$, $(CH_2)_nOC(O)NR^{11}R^{12}$, $(CH_2)_nNR^{11}COOR^{12}$, $(CH_2)_nN(R^{11})CH_2CH_2OR^{13}$, $(CH_2)_nN(R^{11})CH_2CH_2OCF_3$, $(CH_2)_nN(R^{11})C(R^{13})HCOOR^{12}$, $C(R^{13})HCOR^{12}$, $(CH_2)_nN(R^{11})CH_2CH_2N(R^{12})CH_2COOR^{12}$, $(CH_2)_nN(R^{11})CH_2CH_2NR^{11}R^{12}$, $CH=CHCOOR^{11}$, $CH=CHCH_2NR^{11}R^{12}$, $CH=CHCH_2NR^{11}R^{12}$, $CH=CHCH_2OR^{13}$, $(CH_2)_nN(COOR^{11})COOR^{12}$, $(CH_2)_nN(CONH_2)COOR^{11}$, $(CH_2)_nN(CONH_2)CONH_2$, $(CH_2)_nN(CH_2COOR^{11})COOR^{12}$, $(CH_2)_nN(CH_2CONH_2)COOR^{11}$, $(CH_2)_nN(CH_2CONH_2)CONH_2$, $(CH_2)_nCHR^{13}COR^{11}$, $(CH_2)_nCHR^{13}COOR^{11}$, $(CH_2)_nCHR^{13}CH_2OR^{14}$, $(CH_2)_nOCN$ and $(CH_2)_nNCO$, wherein $R^{11}$, $R^{12}$ are independently selected from a group consisting of H, A, $(CH_2)_mAr^3$ and $(CH_2)_mHet$, or in $NR^{11}R^{12}$,
$R^{11}$ and $R^{12}$ form, together with the N-atom they are bound to, a 5-, 6- or 7-membered heterocyclus which optionally contains 1 or 2 additional hetero atoms, selected from N, O an S,
$R^{13}$, $R^{14}$ are independently selected from a group consisting of H, Hal, A, $(CH_2)_mAr^4$ and $(CH_2)_mHet$,
$Ar^3$, $Ar^4$ are independently from one another aromatic hydrocarbon residues comprising 5 to 12 and preferably 5 to 10 carbon atoms which are optionally substituted by one or more substituents, selected from a group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2R^{15}R^{16}$, $S(O)_uA$ and $OOCR^{15}$,
Het is a saturated, unsaturated or aromatic heterocyclic residue which is optionally substituted by one ore more substituents, selected from a group consisting of A, Hal, $NO_2$, CN, $OR^{15}$, $NR^{15}R^{16}$, $COOR^{15}$, $CONR^{15}R^{16}$, $NR^{15}COR^{16}$, $NR^{15}CONR^{15}R^{16}$, $NR^{16}SO_2A$, $COR^{15}$, $SO_2R^{15}R^{16}$, $S(O)_uA$ and $OOCR^{15}$,
$R^{15}$, $R^{16}$ are independently selected from a group consisting of H, A, and $(CH_2)_mAr^6$, wherein
$Ar^6$ is a 5- or 6-membered aromatic hydrocarbon which is optionally substituted by one or more substituents selected from a group consisting of methyl, ethyl, propyl, 2-propyl, tert.-butyl, Hal, CN, OH, $NH_2$ and $CF_3$,
k, m and n are independently of one another 0, 1, 2, 3, 4, or 5,
X represents a bond or is $(CR^{11}R^{12})_h$ or $(CHR^{11})_h-Q-(CHR^{12})_i$, wherein
Q is selected from a group consisting of O, S, $N-R^{15}$, $(CHal_2)_j$, $(O-CHR^{18})_j$, $(CHR^{18}-O)_j$, $CR^{18}=CR^{19}$, $(O-CHR^{18}CHR^{19})_j$, $(CHR^{18}CHR^{19}-O)_j$, C=O, C=S, $C=NR^{15}$, $CH(OR^{15})$, $C(OR^{15})(OR^{20})$, $C(=O)O$, $OC(=O)$, $OC(=O)O$, $C(=O)N(R^{15})$, $N(R^{15})C(=O)$, $OC(=O)N(R^{15})$, $N(R^{15})C(=O)O$, $CH=N-O$, $CH=N-NR^{15}$, S=O, $SO_2$, $SO_2NR^{15}$ and $NR^{15}SO_2$, wherein
$R^{18}$, $R^{19}$, $R^{20}$ are independently selected from the meanings given for $R^8$, $R^9$ and $R^{10}$, preferably independently selected from the group consisting of H, A, Hal, $CH_2Hal$, $CH(Hal)_2$, $C(Hal)_3$, $NO_2$, $(CH_2)_nCN$, $(CH_2)_nOR^{11}$, $(CH_2)_nNR^{11}R^{12}$, $(CH_2)_nO(CH_2)_kNR^{11}R^{12}$, $(CH_2)_nCOOR^{13}$, $(CH_2)_nCONR^{11}R^{12}$, $(CH_2)_nNR^{11}COR^{13}$, $(CH_2)_nNR^{11}CONR^{11}R^{12}$, $(CH_2)_nNR^{11}SO_2A$, $(CH_2)_nSO_2NR^{11}R^{12}$, $(CH_2)_nS(O)_uR^{13}$, $(CH_2)_nCOR^{13}$, $(CH_2)_nSR^{11}$, $(CH_2)_nNHOA$ and $(CH_2)_nNR^{11}COOR^{13}$,
h, i are independently from each other 0, 1, 2, 3, 4, 5, or 6, and
j is 1, 2, 3, 4, 5, or 6,
Y is selected from O, S, $NR^{21}$, $C(R^{22})-NO_2$, $C(R^{22})-CN$ and $C(CN)_2$, wherein
$R^{21}$ is independently selected from the meanings given for $R^{13}$, $R^{14}$ and $R^{22}$ is independently selected from the meanings given for $R^{11}, R^{12}$, p, r are independently from one another 0, 1, 2, 3, 4 or 5, q is 0, 1, 2, 3 or 4, preferably 0, 1 or 2, u is 0, 1, 2 or 3, preferably 0, 1 or 2, and Hal is independently selected from a group consisting of F, Cl, Br and I;

the tautomeric forms thereof; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Even more preferred are compounds of formula I wherein $Ar^2$ is selected from aromatic hydrocarbons containing 6 to 10 and especially 6 carbon atoms and ethylenical unsaturated or aromatic heterocyclic residues containing 3 to 8 and especially 4 to 6 carbon atoms and one or two heteroatoms, independently selected from N, O and S and especially selected from N and O, $R^8, R^9$ and $R^{10}$ are independently selected from a group consisting of H, A, cycloalkyl 3 to 7 carbon atoms, Hal, $CH_2Hal$, $CH(Hal)_2$, $C(Hal)_3$, $NO_2$, $(CH_2)_nCN$, $(CH_2)_n OR^{11}$, $(CH_2)_nNR^{11}R^{12}$, $(CH_2)_nO(CH_2)_kNR^{11}R^{12}$, $(CH_2)_n COOR^{13}$, $(CH_2)_nCONR^{11}R^{12}$, $(CH_2)_nNR^{11}COR^{13}$, $(CH_2)_nNR^{11}CONR^{11}R^{12}$, $(CH_2)_nNR^{11}SO_2A$, $(CH_2)_n SO_2NR^{11}R^{12}$, $(CH_2)_nS(O)_uR^{13}$, $(CH_2)_nOC(O)R^{13}$, $(CH_2)_nCOR^{13}$, $(CH_2)_nSR^{11}$, $(CH_2)_nNHOA$, $(CH_2)_nNR^{11} COOR^{13}$, $(CH_2)_nN(R^{11})CH_2CH_2OR^{13}$, $(CH_2)_nN(R^{11}) CH_2CH_2OCF_3$, $(CH_2)_nN(R^{11})C(R^{13})HCOOR^8$, $(CH_2)_nN (R^{11})$, $C(R^{13})HCOR^8$, $(CH_2)_nN(COOR^{13})COOR^{14}$, $(CH_2)_nN(CONH_2)COOR^{13}$, $(CH_2)_nN(CONH_2)CONH_2$, $(CH_2)_nN(CH_2COOR^{13})COOR^{14}$, $(CH_2)_nN(CH_2CONH_2) COOR^{13}$, $(CH_2)_nN(CH_2CONH_2)CONH_2$, $(CH_2)_nCHR^{13} COR^{14}$, $(CH_2)_nCHR^{13}COOR^{14}$ and $(CH_2)_nCHR^{13} CH_2OR^{14}$, X represents a bond or is $(CR^{11}R^{12})_h$, or $(CHR^{11})_h—Q—(CHR^{12})_i$, wherein Q is selected from a group consisting of O, S, N—$R^{15}$, $(CHal_2)_j$, $(O—CHR^{18})_j$, $(CHR^{18}—O)_j$, $CR^{18}=CR^{19}$, $(O—CHR^{18}CHR^{19})_j$, $(CHR^{18}CHR^{19}—O)_j$, C=O, C=NR^{15}$, $CH(OR^{15})$, $C(OR^{15})(OR^{20})$, $C(=O)N(R^{15})$, $N(R^{15})C(=O)$, CH=N—$NR^{15}$, S=O, $SO_2$, $SO_2NR^{15}$ and $NR^{15}SO_2$, wherein h, i are independently from each other 0, 1, 2, 3, 4, 5 or 6, preferably 0, 1, 2 or 3 and j is 1, 2, 3, 4, 5 or 6, preferably 1, 2, 3 or 4, p is 1, 2, 3 or 4, preferably 1, 2 or 3, and r is 0, 1, 2, or 3, preferably 0, 1 or 2;

the tautomeric forms thereof; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "alkyl" preferably refers to a straight or branched chain hydrocarbon having from one to twelve carbon atoms, optionally substituted with substituents selected from the group consisting of $C_1$-$C_6$ alkyl, $C_1$-$C_6$ alkoxy, $C_1$-$C_6$ alkylsulfanyl, $C_1$-$C_6$ alkylsulfenyl, $C_1$-$C_6$ alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or $C_1$-$C_6$ perfluoroalkyl, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "alkylene" preferably refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl, optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene and the like.

As used herein, the term "halogen" or "hal" preferably refers to fluorine (F), chlorine (Cl), bromine (Br) or iodine (I).

As used herein, the term "haloalkyl" preferably refers to an alkyl group as defined above, preferably containing at least 1 and at most 6 carbon atoms, substituted with at least one halogen, halogen being as defined herein. Examples of branched or straight chained "haloalkyl" groups useful in the present invention include, but are not limited to, methyl, ethyl, propyl, isopropyl, isobutyl and n-butyl substituted independently with one or more halogens, e.g., fluoro, chloro, bromo and iodo.

As used herein, the term "cycloalkyl" preferably refers to a non-aromatic cyclic hydrocarbon ring, preferably having from three to seven carbon atoms, which optionally includes an alkyl linker, preferably a $C_1$-$C_6$ alkyl linker, through which it may be attached. The alkyl or $C_1$-$C_6$ alkyl group is as defined above. Exemplary "cycloalkyl" groups include, but are not limited to, cyclopropyl, cyclobutyl, cyclopentyl, cyclohexyl and cycloheptyl.

As used herein, the term "cycloalkylene" preferably refers to a non-aromatic alicyclic divalent hydrocarbon radical, preferably having from three to seven carbon atoms, which is optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "heterocyclic" or the term "heterocyclyl" preferably refers to a three to twelve-membered heterocyclic ring having one or more degrees of unsaturation containing one or more heteroatomic substitutions selected from S, SO, SO$_2$, O or N, optionally substituted with substituents selected from the group consisting of alkyl, haloalkyl, alkoxy, alkylsulfanyl, haloalkylsulfanyl, alkylsulfenyl, alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or perfluoroalkyl, multiple degrees of substitution being allowed. Such a ring may be optionally fused to one or more other "heterocyclic" ring(s) or cycloalkyl ring(s). Examples of "heterocyclic" moieties include, but are not limited to, tetrahydrofuran, pyran, 1,4-dioxane, 1,3-dioxane, pyrrolidine, piperidine, morpholine, tetrahydrothiopyran, tetrahydrothiophene, and the like.

As used herein, the term "heterocyclylene" preferably refers to a three to twelve-membered heterocyclic ring diradical having one or more degrees of unsaturation containing one or more heteroatoms selected from S, SO, SO$_2$, O or N, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" preferably refers to an optionally substituted benzene ring or to an optionally substituted benzene ring system fused to one or more optionally substituted benzene rings to form, for example, anthracene, phenanthrene, or napthalene ring systems. Exemplary optional substituents include alkyl, alkoxy, alkylsulfanyl, alkylsulfenyl, alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, perfluoroalkyl, heteroaryl, or aryl, multiple degrees of substitution being allowed. Examples of "aryl" groups include, but are not limited to Phenyl, 2-naphthyl, 1-naphthyl, biphenyl, as well as substituted derivatives thereof.

As used herein, the term "arylene" preferably refers to a benzene ring diradical or to a benzene ring system diradical fused to one or more optionally substituted benzene rings, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl and aryl, multiple degrees of substitution being allowed. Examples of "arylene" include, but are not limited to benzene-1,4-diyl, naphthalene-1,8-diyl, anthracene-1,4-diyl, and the like.

As used herein, the term "aralkyl" preferably refers to an aryl or heteroaryl group, as defined herein, attached through a alkyl linker, wherein alkyl is as defined herein. Examples of "aralkyl" include, but are not limited to, benzyl, phenylpropyl, 2-pyridylmethyl, 3-isoxazolylmethyl, 5-methyl-3-isoxazolylmethyl and 2-imidazolylethyl.

As used herein, the term "heteroaryl" preferably refers to a monocyclic five to seven-membered aromatic ring, or to a fused bicyclic aromatic ring system comprising two of such monocyclic five to seven-membered aromatic rings. These heteroaryl rings contain one or more nitrogen, sulfur and/or oxygen heteroatoms, where N-Oxides and sulfur Oxides and dioxides are permissible heteroatom substitutions and may be optionally substituted with up to three members selected from a group consisting of alkyl, haloalkyl, alkoxy, alkylsulfanyl, haloalkylsulfanyl, alkylsulfenyl, alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, perfluoroalkyl, heteroaryl or aryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinolinyl, isoquinolinyl, benzofuranyl, benzothiophenyl, indolyl, indazolyl, and substituted versions thereof.

As used herein, the term "heteroarylene" preferably refers to a five to seven-membered aromatic ring diradical, or to a polycyclic heterocyclic aromatic ring diradical, containing one or more nitrogen, oxygen, or sulfur heteroatoms, where N-Oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "alkoxy" preferably refers to the group $R_aO$—, where $R_a$ is alkyl as defined above and the term "alkoxy" preferably refers to an alkoxy group as defined herein wherein the alkyl moiety contains at least 1 and at most 6 carbon atoms. Exemplary alkoxy groups useful in the present invention include, but are not limited to methoxy, ethoxy, n-propoxy, isopropoxy, n-butoxy and t-butoxy.

As used herein, the term "haloalkoxy" preferably refers to the group $R_aO$—, where $R_a$ is haloalkyl as defined above and the term "haloalkoxy" preferably refers to an haloalkoxy group as defined herein wherein the haloalkyl moiety contains at least 1 and at most 6 carbon atoms. Exemplary haloalkoxy groups useful in the present invention include, but are not limited to, methoxy, ethoxy, n-propoxy, isopropoxy, n-butoxy and t-butoxy substituted with one or more halo groups, for instance trifluoromethoxy.

As used herein the term "aralkoxyl" preferably refers to the group $R_CR_BO$—, where $R_B$ is alkyl and $R_C$ is aryl as defined above.

As used herein the term "aryloxy" preferably refers to the group $R_CO$—, where $R_C$ is aryl as defined above.

As used herein, the term "alkylsulfanyl" preferably refers to the group $R_AS—$, where $R_A$ is alkyl as defined above and the term "alkylsulfanyl" preferably refers to an alkylsulfanyl group as defined herein wherein the alkyl moiety contains at least 1 and at most 6 carbon atoms.

As used herein, the term "haloalkylsulfanyl" preferably refers to the group $R_DS—$, where $R_D$ is haloalkyl as defined above and the term "haloalkylsulfanyl" preferably refers to a haloalkylsulfanyl group as defined herein wherein the alkyl moiety contains at least 1 and at most 6 carbon atoms.

As used herein, the term "alkylsulfenyl" preferably refers to the group $R_AS(O)—$, where $R_A$ is alkyl as defined above and the term "alkylsulfenyl" preferably refers to an alkylsulfenyl group as defined herein wherein the alkyl moiety contains at least 1 and at most 6 carbon atoms.

As used herein, the term "alkylsulfonyl" preferably refers to the group $R_ASO_2—$, where $R_A$ is alkyl as defined above and the term "alkylsulfonyl" preferably refers to an alkylsulfonyl group as defined herein wherein the alkyl moiety contains at least 1 and at most 6 carbon atoms.

As used herein, the term "oxo" preferably refers to the group $=O$.

As used herein, the term "mercapto" preferably refers to the group $—SH$.

As used herein, the term "carboxy" preferably refers to the group $—COOH$.

As used herein, the term "cyano" preferably refers to the group $—CN$.

As used herein, the term "cyanoalkyl" preferably refers to the group $—R_BCN$, wherein $R_B$ is alkylene as defined above. Exemplary "cyanoalkyl" groups useful in the present invention include, but are not limited to, cyanomethyl, cyanoethyl and cyanisopropyl.

As used herein, the term "aminosulfonyl" preferably refers to the group $—SO_2NH_2$.

As used herein, the term "carbamoyl" preferably refers to the group $—C(O)NH_2$.

As used herein, the term "sulfanyl" shall refer to the group $—S—$.

As used herein, the term "sulfenyl" shall refer to the group $—S(O)—$.

As used herein, the term "sulfonyl" shall refer to the group $—S(O)_2—$ or $—SO_2—$.

As used herein, the term "acyl" preferably refers to the group $R_FC(O)—$, where $R_F$ is alkyl, cycloalkyl or heterocyclyl as defined herein.

As used herein, the term "aroyl" preferably refers to the group $R_CC(O)—$, where $R_C$ is aryl as defined herein.

As used herein, the term "heteroaroyl" preferably refers to the group $R_EC(O)—$, where $R_E$ is heteroaryl as defined herein.

As used herein, the term "alkoxycarbonyl" preferably refers to the group $R_AOC(O)—$, where $R_A$ is alkyl as defined herein.

As used herein, the term "acyloxy" preferably refers to the group $R_FC(O)O—$, where $R_F$ is alkyl, cycloalkyl, or heterocyclyl as defined herein.

As used herein, the term "aroyloxy" preferably refers to the group $R_CC(O)O—$, where $R_C$ is aryl as defined herein.

As used herein, the term "heteroaroyloxy" preferably refers to the group $R_EC(O)O—$, where $R_E$ is heteroaryl as defined herein.

As used herein, the term "carbonyl" or "carbonyl moiety" preferably refers to the group $C=O$.

As used herein, the term "thiocarbonyl" or "thiocarbonyl moiety" preferably refers to the group $C=S$.

As used herein, the term "amino", "amino group" or "amino moiety" preferably refers to the group $NR_GR_{G'}$, wherein $R_G$ and $R_{G'}$ are preferably selected, independently from one another, from the group consisting of hydrogen, alkyl, haloalkyl, alkenyl, cycloalkyl, alkylenecycloalkyl, cyanoalkyl, aryl, aralkyl, heteroaryl, acyl and aroyl. If both $R_G$ and $R_{G'}$ are hydrogen, $NR_GR_{G'}$ is also referred to as "unsubstituted amino moiety" or "unsubstituted amino group". If $R_G$ and/or $R_{G'}$ are other than hydrogen, $NR_GR_{G'}$ is also referred to as "substituted amino moiety" or "substituted amino group".

As used herein, the term "imino" or "imino moiety" preferably refers to the group $C=NR_G$, wherein $R_G$ is preferably selected from the group consisting of hydrogen, alkyl, haloalkyl, alkenyl, cycloalkyl, alkylenecycloalkyl, cyanoalkyl, aryl, aralkyl, heteroaryl, acyl and aroyl. If $R_G$ is hydrogen, $C=NR_G$ is also referred to as "unsubstituted imino moiety". If $R_G$ is a residue other than hydrogen, $C=NR_G$ is also referred to as "substituted imino moiety".

As used herein, the term "ethene-1,1-diyl moiety" preferably refers to the group $C=CR_KR_L$, wherein $R_K$ and $R_L$ are preferably selected, independently from one another, from the group consisting of hydrogen, halogen, cyano, alkyl, haloalkyl, alkenyl, cycloalkyl, nitro, alkylenecycloalkyl, cyanoalkyl, aryl, aralkyl, heteroaryl, acyl and aroyl. If both hydrogen $R_K$ and $R_L$ are hydrogen, $C=CR_KR_L$ is also referred to as "unsubstituted ethene-1,1-diyl moiety". If one of $R_K$ and $R_L$ or both are a residue other than hydrogen, $C=CR_KR_L$ is also referred to as "substituted ethene-1,1-diyl moiety".

As used herein, the terms "group", "residue" and "radical" or "groups", "residues" and "radicals" are usually used as synonyms, respectively, as it is common practice in the art.

As used herein, the term "optionally" means that the subsequently described event(s) may or may not occur, and includes both event(s), which occur, and events that do not occur.

As used herein, the term "pharmaceutically acceptable derivative" preferably refers to any physiologically functional derivative of a compound of the present invention, for example, an ester or an amide, which upon administration to a mammal is capable of providing (directly or indirectly) a compound of the present invention or an active metabolite thereof. Such derivatives are clear to those skilled in the art, without undue experimentation, and with reference to the teaching of Burger's Medicinal Chemistry And Drug Discovery, 5th Edition, Vol 1: Principles and Practice, which is incorporated herein by reference to the extent that it teaches physiologically functional derivatives. Such derivatives preferably include so-called prodrug-compounds, for example compounds according to the invention that are derivatized with alkyl groups, acyl groups, sugars or peptides, such as oligopeptides, and that are easily degraded or metabolized to the active compounds according to the invention. Such derivatives preferably include biodegradable polymer derivatives of the compounds according to the invention. Suitable polymers and methods for producing biodegradable polymeric derivatives are known in the art, for example from Int. J. Pharm. 115, 61-67 (1995).

As used herein, the term "solvate" preferably refers to a complex of variable stoichiometry formed by a solute (in this invention, a compound of formula I or formula II or a salt or physiologically functional derivative thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid. Most preferably the solvent used is water. Examples for suitable solvates are the mono- or dihydrates or alcoholates of the compounds according to the invention.

As used herein, the term "substituted" preferably refers to substitution with the named substituent or substituents, multiple degrees of substitution being allowed unless otherwise stated.

Certain of the compounds described herein may contain one or more chiral atoms, or may otherwise be capable of existing as two or more stereoisomers, which are usually enantiomers and/or diastereomers. Accordingly, the compounds of this invention include mixtures of stereoisomers, especially mixtures of enantiomers, as well as purified stereoisomers, especially purified enantiomers, or stereoisomerically enriched mixtures, especially enantiomerically enriched mixtures. Also included within the scope of the invention are the individual isomers of the compounds represented by formulae I above as well as any wholly or partially equilibrated mixtures thereof. The present invention also covers the individual isomers of the compounds represented by the formulas above as mixtures with isomers thereof in which one or more chiral Centers are inverted. Also, it is understood that all tautomers and mixtures of tautomers of the compounds of formula I are included within the scope of the compounds of formula I and preferably the formulae and subformulae corresponding thereto. It is understood that if $R^6$ is Hydrogen (H) or any other group prone to dissociation, the benzimidazole moiety can exist in two or more tautomeric forms, which are usually in an equilibrium relation with one another and thus usually are inseparatable. The equilibrium can be depending on various matters, such as the state of aggregation, the pH value, the solvent the compounds are diluted in etc. Hence, all tautomeric forms are subject of the present invention, no matter which one of the tautomeric forms is depicted in the respective formula.

Racemates obtained can be resolved into the isomers mechanically or chemically by methods known per se. Diastereomers are preferably formed from the racemic mixture by reaction with an optically active resolving agent. Examples of suitable resolving agents are optically active acids, such as the D and L forms of tartaric acid, diacetyltartaric acid, dibenzoyltartaric acid, mandelic acid, malic acid, lactic acid or the various optically active camphorsulfonic acids, such as β-camphorsulfonic acid. Also advantageous is enantiomer resolution with the aid of a column filled with an optically active resolving agent (for example dinitrobenzoylphenylglycine); an example of a suitable eluent is a hexane/isopropanol/acetonitrile mixture.

The diastereomer resolution can also be carried out by standard purification processes, such as, for example, chromatography or fractional crystallization.

It is of course also possible to obtain optically active compounds of the formula I by the methods described above/below by using starting materials which are already optically active.

Unless indicated otherwise, it is to be understood that reference to the compounds of formula I preferably includes the reference to the sub formulae corresponding thereto, for example the sub formulae I.1 to I.18 and preferably formulae Ia to Id. It is also understood that the following embodiments, including uses and compositions, although recited with respect to formula I are preferably also applicable to sub formulae I.1 to I.18 and preferably formulae Ia to Id.

Subject of the present invention are especially compounds of formula I in which one or more substituents or groups, preferably the major part of the substituents or groups has a meaning which is indicated as preferred, more preferred, even more preferred or especially preferred.

In compounds of formula I, the term alkyl more preferably refers to an unbranched or branched alkyl residue, preferably an unbranched alkyl residue comprising 1, 2, 3, 4, 5, 6, 7, 8, 9 or 10, preferably 1, 2, 3, 4, 5 or 6, more preferred 1, 2, 3 or 4 and especially 1 or 2 carbon atoms, or a branched alkyl residue comprising 3, 4, 5, 6, 7, 8, 9 or 10, preferably 3, 4, 5 or 6 more preferred 3 or 4 carbon atoms. The alkyl residues can be optionally substituted, especially by one or more halogen atoms, for example up to perhaloalkyl, by one or more hydroxy groups or by one or more amino groups, all of which can optionally be substituted by alkyl. If an alkyl residue is substituted by halogen, it usually comprises 1, 2, 3, 4 or 5 halogen atoms, depending on the number of carbon atoms of the alkyl residue. For example, a methyl group can comprise, 1, 2 or 3 halogen atoms, an ethyl group (an alkyl residue comprising 2 carbon atoms) can comprise 1, 2, 3, 4 or 5 halogen atoms. If an alkyl residue is substituted by hydroxy groups, it usually comprises one or two, preferably one hydroxy groups. If the hydroxy group is substituted by alkyl, the alkyl substituent comprises preferably 1 to 4 carbon atoms and is preferably unsubstituted or substituted by halogen and more preferred unsubstituted. If an alkyl residue is substituted by amino groups, it usually comprises one or two, preferably one amino groups. If the amino group is substituted by alkyl, the alkyl substituent comprises preferably 1 to 4 carbon atoms and is preferably unsubstituted or substituted by halogen and more preferred unsubstituted. According to compounds of formula I, alkyl is preferably selected from the group consisting of methyl, ethyl, trifluoro methyl, pentafluoro ethyl, isopropyl, tert.-butyl, 2-amino ethyl, N-methyl-2-amino ethyl, N,N-dimethyl-2-amino ethyl, N-ethyl-2-amino ethyl, N,N-diethyl-2-amino ethyl, 2-hydroxy ethyl, 2-methoxy ethyl and 2-ethoxy ethyl, further preferred of the group consisting of 2-butyl, n-pentyl, neo-nentyl, isopentyl, hexyl and n-decyl, more preferred of methyl, ethyl, trifluoro methyl, isoproply and tert.-butyl.

In compounds of formula I, alkenyl is more preferably selected from the group consisting of allyl, 2- or 3-butenyl, isobutenyl, sec-butenyl, furthermore preferably 4-pentenyl, isopentenyl and 5-hexenyl.

In compounds of formula I, alkylene is more preferably unbranched and is even more preferably methylene or ethylene, furthermore preferably propylene or butylene.

In compounds of formula I, alkylenecycloalkyl more preferably has 5 to 10 carbon atoms and is even more preferably methylenecyclopropyl, methylenencyclobutyl, furthermore preferably methylenecyclopentyl, methylenecyclohexyl or methylenecycloheptyl, furthermore alternatively ethylenecyclopropyl, ethylenecyclobutyl, ethylenecyclopentyl, ethylenecyclohexyl or ethylenencycloheptyl, propylenecyclopentyl, propylenecyclohexyl, butylenecyclopentyl or butylenecyclohexyl.

In compounds of formula I, the term "alkoxy" more preferably comprises groups of formula O-alkyl, where alkyl is an alkyl group as defined above. Even more preferred, alkoxy is selected from group consisting of methoxy, ethoxy, n-propoxy, isopropoxy, 2-butoxy, tert.-butoxy and halogenated, especially perhalogenated, derivatives thereof. Preferred perhalogenated derivatives are selected from the group consisting of O—$CCl_3$, O—$CF_3$, O—$C_2Cl_5$, O—$C_2F_5$, O—C($CCO_3$)$_3$ and O—C($CF_3$)$_3$.

In compounds of formula I, the term "alkoxyalkyl" more preferably comprises branched and unbranched residues, even more preferred unbranched residues, of formula $C_uH_{2u+1}$—O—$(CH_2)_v$, wherein u and v are independently from each other 1 to 6. Especially preferred is u=1 and v=1 to 4.

In compounds of formula I the term "alkoxyalkyl" includes alkoxyalkyl groups as defined above, wherein one or more of the hydrogen atoms are substituted by halogen, for example up to perhalo alkoxyalkyl.

In compounds of formula I, cycloalkyl more preferably has 3-7 carbon atoms and is even more preferred cyclopropyl or cyclobutyl, furthermore preferably cyclopentyl or cyclohexyl, furthermore also cycloheptyl, particularly preferably cyclopentyl.

In compounds of formula I, $Ar^2$ is preferably selected from unsubstituted or substituted aryl groups and heteroaryl groups as defined herein. Aryl groups in this respect are preferably selected from unsubstituted or substituted phenyl, 2-naphthyl, 1-naphthyl and biphenyl, more preferably unsubstituted or substituted phenyl. Heteroaryl groups in this respect are preferably selected from unsubstituted or substituted pyridinyl, pyrimidyl, chinolinyl, isochinolinyl, thiophenyl, thiadiazolyl, benzothiadiazolyl, oxazolyl, isoxazolyl, pyrazolyl and imidazolyl, more preferably from unsubstituted or substituted pyridinyl and pyrimidyl.

In compounds of formula I, $Ar^2$ is more preferably selected from the group consisting of phenyl, pyridinyl, pyrimidyl, chinolinyl, isochinolinyl, thiophenyl, thiadiazolyl, benzothiadiazolyl, oxazolyl, isoxazolyl, pyrazolyl and imidazolyl, even more preferably from phenyl, pyridinyl and pyrimidyl and especially preferred from phenyl and pyridinyl.

In compounds of formula I, $Ar^3$ to $Ar^6$ are more preferably selected independently from one another from phenyl, naphthyl and biphenyl which is optionally substituted by one or more substituents, selected from the group consisting of A, Hal, $NO_2$, CN, $OR^{15}$, $NR^{15}R^{16}$, $COOR^{15}$, $CONR^{15}R_{11}$, $NR^{15}COR^{16}$, $NR^{15}CONR^{15}R^{16}$, $NR^{18}SO_2A$, $COR^{15}$, $SO_2R^{15}R^{16}$, $S(O)_uA$ and $OOCR^{15}$.

In compounds of formula I, het is more preferably an optionally substituted aromatic heterocyclic residue and even more preferred an optionally substituted saturated heterocyclic residue, wherein the substituents are preferably selected from A, CN and Hal. Even more preferred, het is selected from the group consisting of 1-piperidyl, 1-piperazyl, 1-(4-methyl)-piperazyl, 4-methylpiperazin-1-yl amine, 4-morpholinyl, 1-4pyrrolidinyl, 1-pyrazolidinyl 1-(2-methylpyrazolidinyl, 1-imidazolidinyl or 1-(3-methyl)-imidazolidinyl, thiophen-2-yl, thiophen-3-yl, 2-pyridyl, 3-pyridyl, 4-pyridyl, 2-oxazolyl, 4-oxazolyl, 5-oxazolyl, 2-thiazolyl, 4-thiazolyl, 5-thiazolyl, chinolinyl, isochinolinyl, 2-pyridazyl, 4-pyridazyl, 2-pyrimidyl, 4-pyrimidyl, 5-pyrimidyl, 2-pyrazinyl and 3-pyrazinyl.

A preferred aspect of the instant invention relates to compounds of formula I, wherein n is 0 or 1 and especially 0.

Another preferred aspect of the instant invention relates to compounds of formula I, wherein n is 0 in the residues $R^8$, $R^9$ and/or $R^{10}$ and especially in $R^{10}$.

Another preferred aspect of the instant invention relates to compounds of formula I, wherein X represents a bridging group, selected from $(CR^{11}R^{12})_h$ or $(CHR^{11})_h$—Q—$(CHR^{12})_j$.

If the bridging group X is $(CR^{11}R^{12})_h$, h is preferably selected from 0, 1, 2, 3 and 4, more preferably from 1, 2, 3 and 4 and especially from 1 or 2.

If the bridging group X is $(CHR^{11})_h$—Q—$(CHR^{12})_i$, h and/or i are preferably selected from 0, 1, 2, 3 and 4, more preferably from 0, 1, 2 and 3 and especially from 0, 1 or 2, and even more preferred, both h and i are 0. The invention relates in particular to compounds of the formula I in which at least one of said radicals has one of the preferred meanings given above.

Some more preferred groups of compounds may be expressed by the following sub-formulae I.1) to I.18), which correspond to the formula I and in which radicals not denoted in greater detail are as defined in the formula I, but in which I.1) p is 1, 2 or 3;

I.2) p is 1, 2 or 3,
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}$, $R^{12}$, $(CH_2)_nSO_2NR^{11}R^{12}$ and $(CH_2)_nS(O)_uR^{13}$;

I.3) p is 1, 2 or 3,
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
n is 0, 1 or 2, preferably 0 or 1;

I.4) p is 1, 2 or 3,
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
n is 0, 1 or 2, preferably 0 or 1, and
q is 0 or 1;

I.5) p is 1, 2 or 3,
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
n is 0, 1 or 2, preferably 0 or 1,
q is 0 or 1, and
X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S;

I.6) p is 1, 2 or 3,
$R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
n is 0, 1 or 2, preferably 0 or 1,
q is 0 or 1, and
X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S,
$Ar^2$ is phenyl, pyridinyl or pyrimidyl, and especially is phenyl or pyridinyl;

I.7) p is 1, 2 or 3,
  $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R_{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
  n is 0, 1 or 2, preferably 0 or 1,
  q is 0 or 1, and
  X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S,
  $Ar^2$ is phenyl, pyridinyl or pyrimidyl, and especially is phenyl or pyridinyl, and
  $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$;

I.8) p is 1, 2 or 3,
  $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
  n is 0, 1 or 2, preferably 0 or 1,
  q is 0 or 1, and
  X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S,
  $Ar^2$ is phenyl, pyridinyl or pyrimidyl, and especially is phenyl or pyridinyl, and
  $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$,
  k is 0, 1 or 2, preferably 0 or 2;

I.9) p is 1, 2 or 3,
  $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
  n is 0, 1 or 2, preferably 0 or 1,
  q is 0 or 1, and
  X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S,
  $Ar^2$ is phenyl, pyridinyl or pyrimidyl, and especially is phenyl or pyridinyl, and
  $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$,
  k is 0, 1 or 2, preferably 0 or 2 and
  r is 0, 1 or 2, preferably 0 or 1;

I.10) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
  n is 0, 1 or 2, preferably 0 or 1,
  q is 0 or 1, and
  X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S,
  $Ar^2$ is phenyl, pyridinyl or pyrimidyl, and especially is phenyl or pyridinyl, and
  $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$,
  k is 0, 1 or 2, preferably 0 or 2 and
  r is 0, 1 or 2, preferably 0 or 1;

I.11) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$,
  q is 0 or 1, and
  X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S,
  $Ar^2$ is phenyl, pyridinyl or pyrimidyl, and especially is phenyl or pyridinyl, and
  $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, k is 0, 1 or 2, preferably 0 or 2 and r is 0, 1 or 2, preferably 0 or 1;

I.12) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl, and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, k is 0, 1 or 2, preferably 0 or 2 and r is 0, 1 or 2, preferably 0 or 1;

I.13) $R^8$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kN^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, q is 0 or 1, and X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$, and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, k is 0, 1 or 2, preferably 0 or 2 and r is 0, 1 or 2, preferably 0 or 1;

I.14) q is 0 or 1, and

X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl, and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, k is 0, 1 or 2, preferably 0 or 2 and r is 0, 1 or 2, preferably 0 or 1;

I.15) X is selected from the group consisting of O, S, $NR^{11}$, $CHOR^{11}$, $CH_2$, $CH_2CH_2$, $OCH_2$, $CH_2O$, $OCH_2CH_2$, $CH_2CH_2O$, preferably O, S and $CH_2$ and especially O and S, $Ar^2$ is phenyl, pyridinyl or pyrimidyl, and especially is phenyl or pyridinyl, and $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kN^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, k is 0, 1 or 2, preferably 0 or 2 and r is 0, 1 or 2, preferably 0 or 1;

I.16) $Ar^2$ is phenyl, pyridinyl or pyrimidyl, and especially is phenyl or pyridinyl, and $R^{10}$ is selected from the group consisting of alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, k is 0, 1 or 2, preferably 0 or 2 and r is 0, 1 or 2, preferably 0 or 1;

I.17) $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$ and especially $(CH_2)_nCONR^{11}R^{12}$, k is 0, 1 or 2, preferably 0 or 2 and r is 0, 1 or 2, preferably 0 or 1;

I.18) $R^{10}$ is selected from the group consisting of H, alkyl comprising 1 to 4 carbon atoms, alkoxy comprising 1 to 4 carbon atoms, Hal, $CH_2Hal$, $CH(Hal)_2$, perhaloalkyl comprising 1 to 4 carbon atoms, $NO_2$, $(CH_2)_nCN$, $(CH_2)_nNR^{11}R^{12}$, $(CH_2)_nO(CH_2)_kNR^{11}R^{12}$, $(CH_2)_nCOR^{13}$, $(CH_2)_nCOOR^{13}$, $(CH_2)_nCONR^{11}R^{12}$, $(CH_2)_nSO_2NR^{11}R^{12}$ and $(CH_2)_nS(O)_uR^{13}$, preferably selected from the group consisting of alkyl comprising 1 to 4 carbon atoms, $(CH_2)_nNR^{11}R^{12}$, $(CH_2)_nO(CH_2)_kNR^{11}R^{12}$, $(CH_2)_n$ $COR^{13}$, $(CH_2)_nCOOR^{13}$, $(CH_2)_nCONR^{11}R^{12}$ and especially $(CH_2)_nCONR^{11}R^{12}$, and r is 0, 1 or 2, preferably 0 or 1.

One preferred embodiment of the instant invention relates to compounds of formula I and preferably one or more of sub formulae I.1) to I.18), wherein p is 1, 2 or 3 and $R^8$ is independently selected from the group consisting of methyl, ethyl, isopropyl, tert.-butyl, F, Cl, Br, $CF_3$, $C(CF_3)_3$, methoxy, ethoxy, tert.-butoxy, perfluoro tert.-butoxy ($OC(CF_3)_3$), methyl sulfanyl ($SCH_3$), ethyl sulfanyl ($SCH_2CH_3$), acetyl ($COCH_3$), propionyl ($COCH_2CH_3$), butyryl ($COCH_2CH_2CH_3$) and $SO_2CF_3$. If p is 2 or 3, all substituents can be the same or different.

Another preferred embodiment of the instant invention relates to compounds of formula I and preferably one or more of sub formulae I.1) to I.18), wherein the sum of h and i exceeds 0.

Another more preferred embodiment of the instant invention relates to compounds of formula I and preferably one or more of sub formulae I.1) to I.18), wherein h and/or i are 0.

Another preferred embodiment of the instant invention relates to compounds of formula I and preferably one or more of sub formulae I.1) to I.18), wherein X is selected from the group consisting of O, S, N—$R^{21}$, $CH_2$, $CH_2CH_2$, $OCH_2$, $CH_2O$, $C=O$, $C(=O)$—NH and NH—$C(=O)$.

Another preferred embodiment of the instant invention relates to compounds of formula I and preferably one or more of sub formulae I.1) to I.18), wherein X is selected from the group consisting of S, N—$R^{21}$, $CH_2$, $CH_2CH_2$, $OCH_2$, $CH_2O$, $C=O$, $C(=O)$—NH and NH—$C(=O)$.

Another preferred embodiment of the instant invention relates to compounds of formula I and preferably one or more of sub formulae I.1) to I.18), wherein X is selected from the group consisting of S, $CH_2$.

Another even more preferred embodiment of the instant invention relates to compounds of formula I and preferably one or more of sub formulae I.1) to I.18), wherein X is O.

Another preferred embodiment of the instant invention relates to compounds of formula I and preferably one or more of sub formulae I.1) to I.18), wherein Y is selected from the group consisting of $C(R^{22})$—$NO_2$, $C(R^{22})$—CN and $C(CN)_2$.

Another more preferred embodiment of the instant invention relates to compounds of formula I and preferably one or more of sub formulae I.1) to I.18), wherein Y is selected from the group consisting of O, S and $NR^{21}$.

Another even more preferred embodiment of the instant invention relates to compounds of formula I and preferably one or more of sub formulae I.1) to I.18), wherein Y is selected from the group consisting of O and S.

Another even more preferred embodiment of the instant invention relates to compounds of formula I and preferably one or more of sub formulae I.1) to I.18), wherein Y is O.

Another preferred embodiment of the instant invention relates to compounds of formula I and preferably one or more of sub formulae I.1) to I.18), wherein $Ar^2$ is pyridinyl.

Another preferred embodiment of the instant invention relates to compounds of formula I and preferably one or more of sub formulae I.1) to I.18), wherein r is either 0 or 1. If r is 1, $R^{10}$ is preferably $(CH_2)_nCONR^{11}R^{12}$ and especially $(CH_2)_nCONR^{11}R^{12}$, wherein n is 0. In this embodiment, $R^{11}$ is preferably selected from the group consisting of H and A, more preferred from H and alkyl and especially is H, and $R^{12}$ is preferably selected from the group consisting of H and A and more preferred from H, unsubstituted alkyl and substituted alkyl, preferably comprising 1 to 6 and especially 1 or 2 carbon atoms. Suitable for substituents include amino groups, such as $NH_2$, $NHCH_3$, $NHCH_2CH_3$, $N(CH_3)_2$ and $NH(CH_2CH_3)$, and carboxyl groups and derivatives thereof, such as COOH, $COOCH_3$, $CONH_2$, and $CONHCH_3$. Especially preferred as residue $R^{10}$ are $CONHCH_3$, $CONHCH_2CH_2NH_2$, $CONHCH_2CH_2NHCH_3$, $CONH CH_2CH_2N(CH_3)_2$, $CONHCH_2COOH$ and $CONH CH_2CH_2COOH$. This embodiment is especially preferred when $Ar^2$ is pyridinyl. When $Ar^2$ is pyridinyl, $R^{10}$ is preferably bonded in a vicinal position to the nitrogen atom of the pyrindiyl residue, i.e. in 2- and/or 6-position of the pyridinyl residue.

Another preferred embodiment of the instant invention relates to compounds of formula I and preferably one or more of sub formulae I.1) to I.18), wherein the benzimidazole-moiety comprises two or more substituents $R^8$, wherein one or more, preferably one substituent $R^8$ is selected from the group consisting of $(CH_2)_nNR^{11}R^{12}$, $(CH_2)_nO(CH_2)_k NR^{11}R^{12}$, $(CH_2)_nNR^{11}(CH_2)_kOR^{12}$, $(CH_2)_nNR^{11}(CH_2)_k NR^{12}R^{12}$, $(CH_2)_nCOOR^{13}$ and $(CH_2)_nS(O)_uR^{13}$ wherein $R^{11}R^{12}$ and $R^{13}$ are defined as above and n is as defined above, preferably n is 0, 1 or 2 and especially is 0, k is 1 to 4 and preferably 1 or 2, and u is preferably 2. In this embodiment $R^{11}$, $R^{12}$ and $R^{13}$ are more preferably selected independently from each other from the group consisting of H, methyl and ethyl. In this embodiment, one or two substituents $R^8$ and preferably one substituent $R^8$ is especially preferably selected from the group consisting of $NH_2$, $N(CH_3)_2$, $N(C_2H_5)_2$, $NHCH_2CH_2NH_2$, $N(CH_3)CH_2CH_2NH_2$, $N(CH_3)CH_2CH_2N (CH_3)_2$, $N(CH_3)CH_2CH_2N(CH_3)_2$, $N(CH_3)CH_2CH_2OCH_3$, $OCH_2CH_2N(CH_3)_2$, $SCH_3$, $SC_2H_5$, $SO_2CH_3$, $COOCH_3$ and COOH. Accordingly, in this embodiment the benzimidazole-moiety especially preferably comprises at least one substituent $R^8$ other than $(CH_2)_nNR^{11}R^{12}$, $(CH_2)_nO(CH_2)_kNR^{11}R^{12}$, $(CH_2)_nNR^{11}(CH_2)_kOR^{12}$, $(CH_2)_nNR^{11}(CH_2)_kNR^{12}R^{12}$, $(CH_2)_nCOOR^{13}$ and $(CH_2)_nS(O)_uR^{13}$ as defined in this paragraph and especially other than $NH_2$, $N(CH_3)_2$, $N(C_2H_5)_2$, $NHCH_2CH_2NH_2$, $N(CH_3)CH_2CH_2NH_2$, $N(CH_3)CH_2CH_2N (CH_3)_2$, $N(CH_3)CH_2CH_2N(CH_3)_2$, $N(CH_3)CH_2CH_2OCH_3$, $OCH_2CH_2N(CH_3)_2$, $SCH_3$, $SC_2H_5$, $SO_2CH_3$, $COOCH_3$ and COOH.

Another preferred embodiment of the instant invention relates to compounds of formula I and preferably one or more of sub formulae I.1) to I.18), wherein q is 1, i.e. the phenylene moiety bound to the oxamide group and the radical X is substituted once, preferably by a substituent selected from the group consisting of alkyl and halogen and more preferred from methyl, ethyl, F, Cl and Br.

Another preferred embodiment of the instant invention relates to compounds of formula I and preferably one or more of sub formulae I.1) to I.18), wherein q is 0, i.e. the phenylene moiety bound to the oxamide group and the radical X is unsubstituted.

Another preferred embodiment of the instant invention relates to compounds of formula I and preferably one or more of sub formulae I.1) to I.18), wherein the $(R^8)_p$-benzimidazole-moiety is as defined above, but comprises one or more additional residues, preferably one additional residue. The additional residues are preferably selected from the meanings given for $R^8$ and more preferably selected from the group consisting of $(CH_2)_nNR^{11}R^{12}$, $(CH_2)_nO(CH_2)_kNR^{11}R^{12}$, $(CH_2)_nNR^{11}(CH_2)_kOR^{12}$, $(CH_2)_nNR^{11}(CH_2)_kNR^{12}R^{12}$, $(CH_2)_nCOOR^{13}$ and $(CH_2)_nS(O)_uR^{13}$ wherein $R^{11}$, $R^{12}$ and $R^{13}$ are defined as above and n is as defined above, preferably n is 0, 1 or 2 and especially is 0, k is 1 to 4 and preferably 1 or 2, and u is preferably 2. In this embodiment $R^{11}$, $R^{12}$ and $R^{13}$ are more preferably selected independently from each other from the group consisting of H, methyl and ethyl. Even more preferred, the additional residue(s) is/are selected from the group consisting of $NH_2$, $N(CH_3)_2$, $N(C_2H_5)_2$, $NHCH_2CH_2NH_2$, $N(CH_3)CH_2CH_2NH_2$, $N(CH_3)CH_2CH_2N(CH_3)_2$, $N(CH_3)CH_2CH_2N(CH_3)_2$, $N(CH_3)CH_2CH_2OCH_3$, $OCH_2CH_2N(CH_3)_2$, $SCH_3$, $SC_2H_5$, $SO_2CH_3$, $COOCH_3$ and $COOH$.

Another preferred embodiment of the instant invention relates to compounds of formula I and preferably one or more of sub formulae I.1) to I.18), wherein X is bonded in the para-(p-) or metha-(m-)position to the phenyl residue that is bonded directly to the oxamide moiety.

Another preferred embodiment of the instant invention relates to compounds of formula I and preferably one or more of sub formulae I.1) to I.18), wherein $Ar^2$ is a pyridinyl residue and wherein said pyridinyl residue is bonded to X in the 3- or 4-position, preferably the 4-position, relative to the nitrogen atom of the pyridinyl residue.

Another preferred embodiment of the instant invention relates to compounds of formula I and preferably one or more of sub formulae I.1) to I.18), wherein $Ar^2$ comprises one or more substituents $R^{10}$ and wherein one or two, preferably one substituent $R^{10}$ is selected from unsubstituted or substituted carbamoyl moieties. Substituted carbamoyl moieties are preferably selected from $CONHR^{23}$ or $CONR^{23}R^{24}$, preferably $CONHR^{23}$, wherein $R^{23}$ and $R^{24}$ are independently selected from the definitions given for $R^8$, more preferably selected from alkyl, preferably methyl, ethyl, propyl and butyl, $(CH_2)_nNR^{11}R^{12}$ and $(CH_2)_nOR^{12}$, wherein $R^{11}$, $R^{12}$ and n are as defined above. In this embodiment, n is preferably not 0 and more preferred 1 to 3 and especially 1 or 2. Preferred examples for $R^{23}$ are selected from the group consisting of methyl, ethyl, $CH_2CH_2NH_2$, $CH_2CH_2N(CH_3)_2$, $CH_2CH_2N(CH_2CH_3)_2$, $CH_2CH_2OH$, $CH_2CH_2OCH_3$ and $CH_2CH_2OCH_2CH_3$.

Another preferred embodiment of the instant invention relates to compounds of formula I and preferably one or more of sub formulae I.1) to I.18), wherein $Ar^2$ comprises one or more substituents $R^{10}$ and wherein one or two, preferably one substituent $R^{10}$ is selected from substituted carbamoyl moieties. Substituted carbamoyl moieties are preferably selected from $CONHR^{23}$, wherein $R^{23}$ is preferably unsubstituted $C_1$-$C_4$-alkyl and especially methyl.

Another preferred embodiment of the instant invention relates to compounds of formula I and preferably one or more of sub formulae I.1) to I.18), wherein $Ar^2$ comprises one or more substituents $R^{10}$ and wherein one or two, preferably one substituent $R^{10}$ is selected from substituted carbamoyl moieties. Substituted carbamoyl moieties are preferably selected from $CONHR^{23}$, wherein $R^{23}$ is selected from $(CH_2)_nNR^{11}R^{12}$ and $(CH_2)_nOR^{12}$, wherein $R^{11}$, $R^{12}$ and n are as defined above. In this embodiment, n is preferably not 0 and more preferred 1 to 3 and especially 1 or 2. Preferred examples for $R^{23}$ are selected from the group consisting of $CH_2CH_2NH_2$, $CH_2CH_2N(CH_3)_2$, $CH_2CH_2N(CH_2CH_3)_2$, $CH_2CH_2OH$, $CH_2CH_2OCH_3$ and $CH_2CH_2OCH_2CH_3$.

Another preferred embodiment of the instant invention relates to compounds of formula I and preferably one or more of sub formulae I.1) to I.18), wherein —$Ar^2$—($R^{10}$) is selected from the formulae

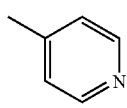 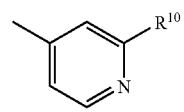

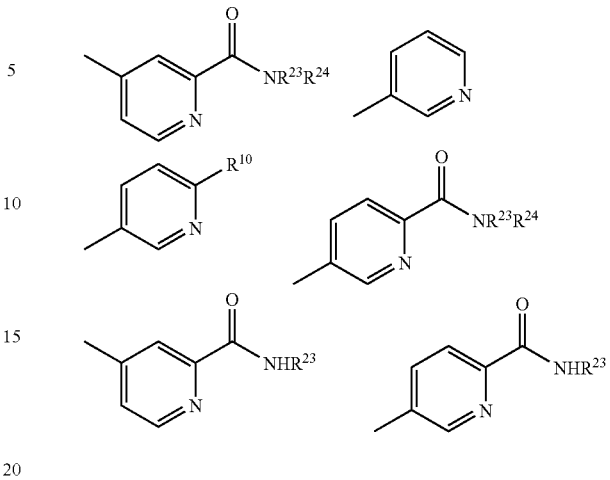

wherein $R^{10}$, $R^{23}$ and $R^{24}$ are as defined above and below.

Another preferred embodiment of the instant invention relates to compounds of formula I and preferably one or more of sub formulae I.1) to I.18), wherein the benzimidazole-moiety comprises one or more substituents $R^8$ and wherein one or two, preferably one substituent $R^8$ is selected from the group consisting of $NH_2$, $N(CH_3)_2$, $NHCH_3$, $N(C_2H_5)_2$, $HNCH_2CH_2NH_2$, $OCH_2CH_2NH_2$, $HOCH_2CH_2NH$, $OCH_2CH_2NHCH_3$, $N(CH_3)CH_2CH_2NH_2$, $HN(CH_3)CH_2CH_2NH$, $N(CH_3)CH_2CH_2N(CH_3)_2$, $N(CH_3)CH_2CH_2N(CH_3)_2$, $N(CH_3)CH_2CH_2OCH_3$, $OCH_2CH_2N(CH_3)_2$, $OCH_2CH_2N(CH_2CH_3)_2$, $SCH_3$, $SC_2H_5$, and compounds of the formulae

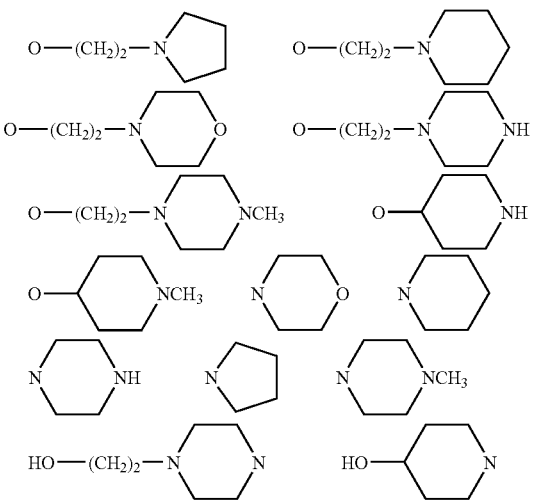

and/or $Ar^2$ comprises one or more substituents $R^{10}$ and wherein one or two, preferably one substituent $R^{10}$ is independently selected from the meanings given for $R^8$ in this paragraph.

Another especially preferred embodiment of the instant invention relates to compounds of formula I and preferably one or more of sub formulae I.1) to I.18), wherein one or more features of the above and below mentioned embodiments are combined in one compound.

Subject of the present invention are therefore especially preferred compounds of formula I according to one or more of the formulae Ia, Ib, Ic and Id,

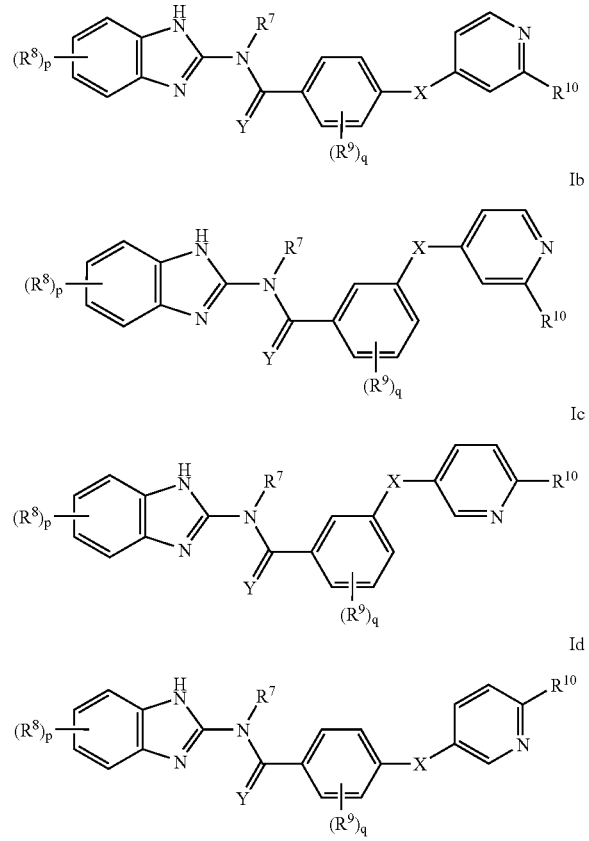

wherein $R^7$, $R^8$, p, X, Y, $R^9$ and q are as defined above and below, and $R^{10}$ is H or as defined above and below, and preferably all are as defined in sub formulae I.1) to I.18) and/or the embodiments related thereto; the tautomeric forms thereof; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

Another preferred embodiment of the instant invention relates to compounds of formula I and preferably one or more of sub formulae I.1) to I.18) and Ia to Id, wherein $R^{10}$ is a substituted carbamoyl moiety $CONHR^{23}$ or $CONR^{23}R^{24}$, preferably $CONHR^{23}$, wherein $R^{23}$ and $R^{24}$ are independently selected from the definitions given for $R^8$, more preferably selected from $(CH_2)_nNR^{11}R^{12}$ and $(CH_2)_nOR^{12}$, wherein $R^{11}$, $R^{12}$ and n are as defined above. In this embodiment, n is preferably not 0 and more preferred 1 to 3 and especially 1 or 2. Preferred examples for $R^{23}$ are selected from the group consisting of $CH_2CH_2NH_2$, $CH_2CH_2N(CH_3)_2$, $CH_2CH_2N(CH_2CH_3)_2$, $CH_2CH_2OH$, $CH_2CH_2OCH_3$, $CH_2CH_2OCH_2CH_3$ and from the formulae

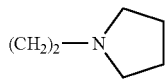 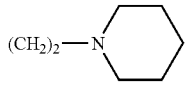

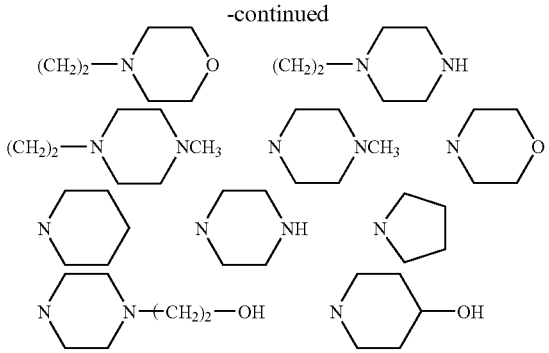

It is understood that when a residue, for example $R^8$, $R^9$, $R^{10}$ or $R^{14}$ or $R^{23}$, is comprised twice or more times in one or more of the formulae I and the sub formulae corresponding thereto, it is in each case independently from one another selected from the meanings given for the respective residue. For example, $R^{11}$ and $R^{12}$ are defined to be independently selected from a group consisting of H, A, $(CH_2)_mAr^3$ and $(CH_2)_m$Het. Then $(CH_2)_nNR^{11}(CH_2)_mNR^{12}R^{12}$ can be $(CH_2)_nNA(CH_2)_mNA_2$ (if $R^{11}=A$, $R^{12}=A$ and $R^{12}=H$) as well as $(CH_2)_nNA(CH_2)_mNHA$ (if $R^{11}=A$, $R^{12}=H$ and $R^{12}=A$ or $(CH_2)_nNA(CH_2)_mNH(CH_2)_m$Het (if $R^{11}=A$, $R^{12}=H$ and $R^{12}=(CH_2)_m$Het). Accordingly, if a compound of formula I comprises one residue $R^8$, $R^9$ and $R^{10}$, then for example $R^8$, $R^9$ and $R^{10}$ can all be $(CH_2)_nCOOR^{13}$, wherein all residues $R^{13}$ are the same (for example $CH_2$Hal, wherein Hal is Cl; then all residues $R^8$, $R^9$ and $R^{10}$ are the same) or different (for example $CH_2$Hal, wherein in $R^8$ Hal is Cl; in $R^9$ Hal is F; and in $R^{10}$ Hal is Br; then all residues $R^8$, $R^9$ and $R^{10}$ are different); or for example $R^8$ is $(CH_2)_nCOOR^{13}$, $R^9$ is $NO_2$ and $R^{10}$ is $(CH_2)_nSR^{11}$, wherein $R^{11}$ and $R^{13}$ can be the same (for example both can be H or both can be A which is methyl) of different (for example $R^{11}$ can be H and $R^{13}$ can be A which is methyl).

If not stated otherwise, reference to compounds of formula I also includes the sub formulae related thereto, especially sub formulae I.1) to I.18) and Ia to Id.

Subject of the instant invention are especially those compounds of formula I in which at least one of the residues mentioned in said formulae has one of the preferred or especially preferred meanings given above and below.

The present invention further relates to compounds of formula Ie

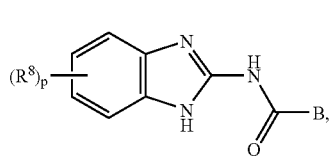

wherein $(R^8)_p$ denotes no substituent;

$(R^8)_p$ is 4-$CH_3$;

$(R^8)_p$ is 4-$CF_3$;

$(R^8)_p$ is 5-Cl;

$(R^8)_p$ is 5-$CF_3$;

$(R^8)_p$ is 4-CH$_3$ and 5-CH$_3$;

$(R^8)_p$ is 4-CH$_3$ and 5-Cl;

$(R^8)_p$ is 4-Br and 6-CF$_3$;

$(R^8)_p$ is 4-CF$_3$ and 6-Br;

$(R^8)_p$ is 5-Cl and 6-CF$_3$;

$(R^8)_p$ is 4-CH$_3$;

$(R^8)_p$ is 4-Cl, 6-CF$_3$;

$(R^8)_p$ is 4-CF$_3$, 6-Cl;

$(R^8)_p$ is 5-Cl and 6-CH$_3$;

$(R^8)_p$ is 5-Cl and 6-CF$_3$;

$(R^8)_p$ is 4-CF$_3$ and 6-CF$_3$;

$(R^8)_p$ is 5-Cl and 6-Cl;

and/or $(R^8)_p$ is 5-CH$_3$;

and wherein B is selected from the group as given below:

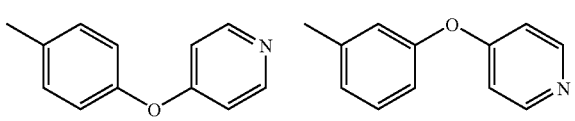

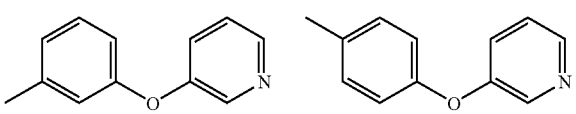

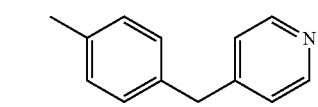

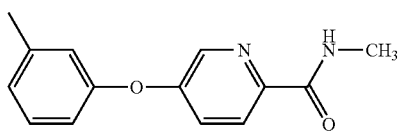

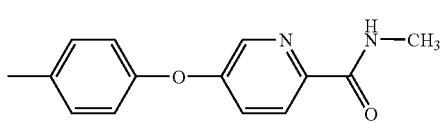

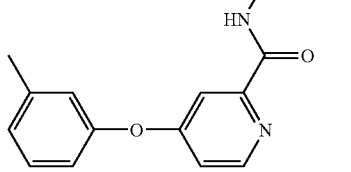

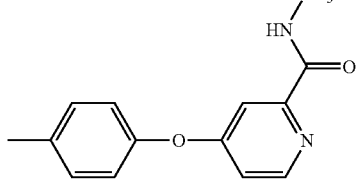

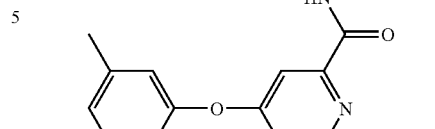

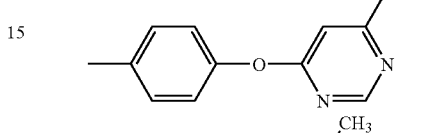

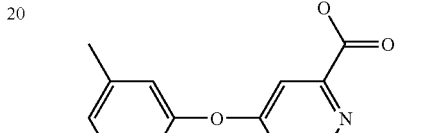

the tautomeric forms thereof; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

The present invention further relates to compounds of formula Iee

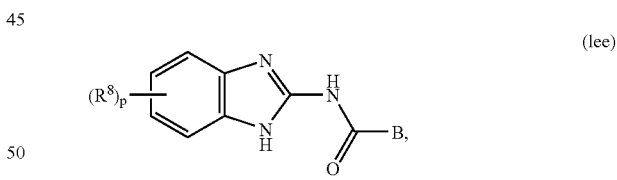

(Iee)

wherein $(R^8)_p$ denotes no substituent;

$(R^8)_p$ is 5-Cl;

$(R^8)_p$ is 5-CF$_3$;

$(R^8)_p$ is 4-CH$_3$ and 5-Cl;

$(R^8)_p$ is 4-Br and 6-CF$_3$;

$(R^8)_p$ is 5-Cl and 6-CF$_3$;

$(R^8)_p$ is 4-CH$_3$;

$(R^8)_p$ is 4-Cl, 6-CF$_3$;

$(R^8)_p$ is 5-Cl and 6-CH$_3$;

($R^8$)$_p$ is 4-CF$_3$ and 6-CF$_3$;

($R^8$)$_p$ is 5-Cl and 6-Cl;

and/or ($R^8$)$_p$ is 5-CH$_3$;

and wherein B is selected from the group as given below:

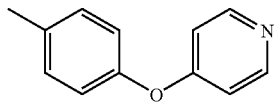

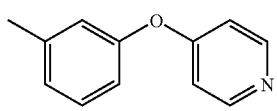

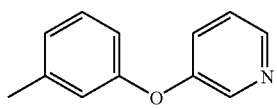

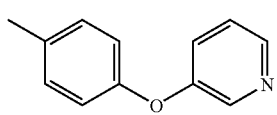

-continued

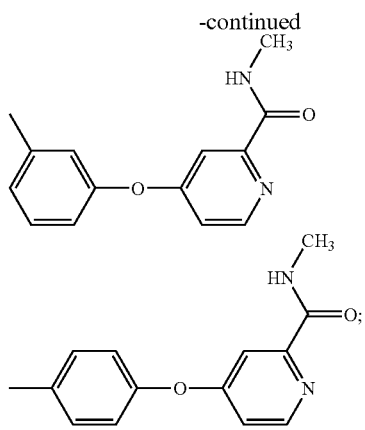

the tautomeric forms thereof; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof.

The present invention further relates to compounds (1) to (78) of formula A—NH—CO—B, wherein A— and —B are as given in the table 1 below:

| | A- | ,-B |
|---|---|---|
| (1) | 2-methylbenzimidazole | 4-(pyridin-4-yloxy)toluene |
| (2) | 2-methylbenzimidazole | 3-(pyridin-4-yloxy)toluene |
| (3) | 2-methylbenzimidazole | 3-(pyridin-3-yloxy)toluene |
| (4) | 2-methylbenzimidazole | 4-(pyridin-3-yloxy)toluene |
| (5) | 2-methylbenzimidazole | N-methyl-4-(3-methylphenoxy)pyridine-2-carboxamide |

|  | A- | ,-B |
|---|---|---|
| (6) | 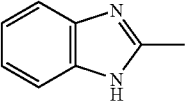 |  |
| (7) | 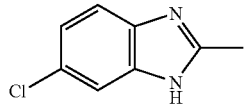 | 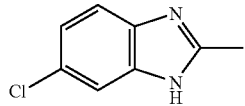 |
| (8) | 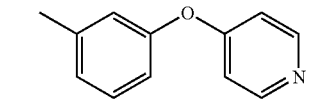 | 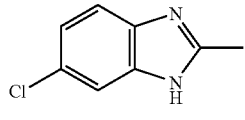 |
| (9) | 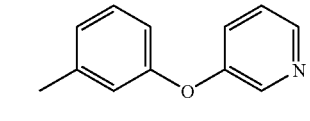 | 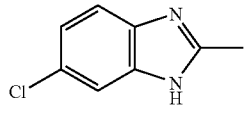 |
| (10) | 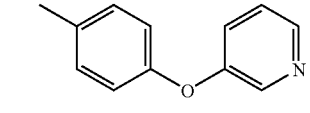 | 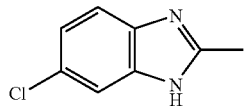 |
| (11) | 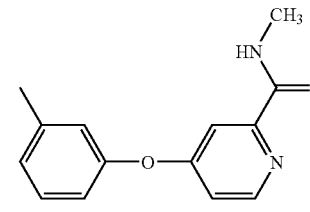 | 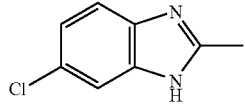 |
| (12) | 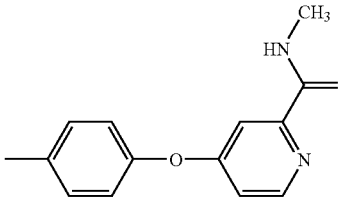 | 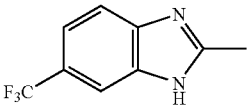 |
| (13) | 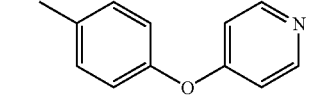 | 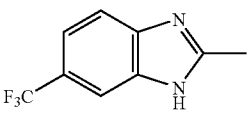 |
| (14) | 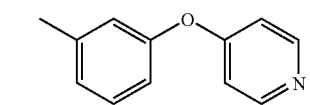 | 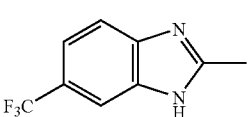 |
| (15) | 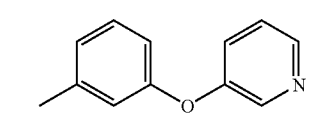 | |

-continued
| | A- | ,-B |
|---|---|---|
| (16) | 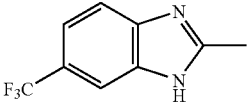 | 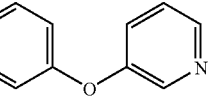 |
| (17) | 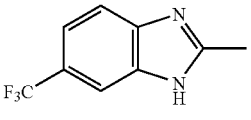 | 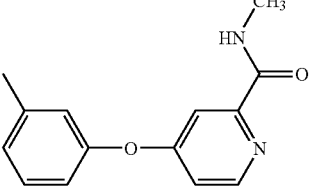 |
| (18) | 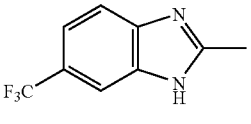 | 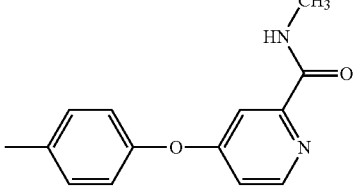 |
| (19) | 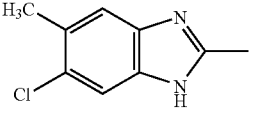 | 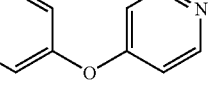 |
| (20) | 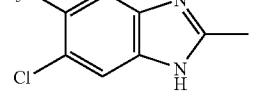 | 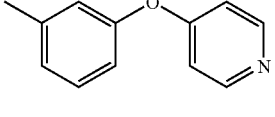 |
| (21) | 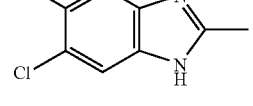 | 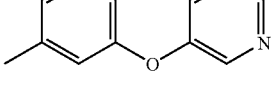 |
| (22) | 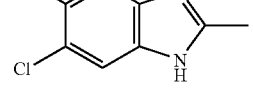 | 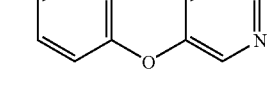 |
| (23) | 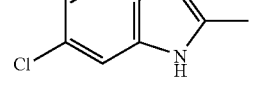 | 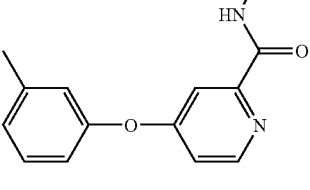 |
| (24) | 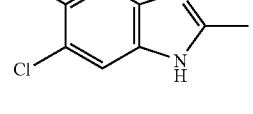 | 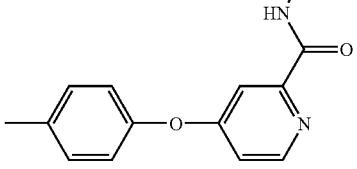 |

-continued

| | A- | ,-B |
|---|---|---|
| (25) | 5-bromo-2-methyl-7-trifluoromethyl-1H-benzimidazole | 4-(4-methylphenoxy)pyridine |
| (26) | 5-bromo-2-methyl-7-trifluoromethyl-1H-benzimidazole | 4-(3-methylphenoxy)pyridine |
| (27) | 5-bromo-2-methyl-7-trifluoromethyl-1H-benzimidazole | 3-(3-methylphenoxy)pyridine |
| (28) | 5-bromo-2-methyl-7-trifluoromethyl-1H-benzimidazole | 3-(4-methylphenoxy)pyridine |
| (29) | 5-bromo-2-methyl-7-trifluoromethyl-1H-benzimidazole | 4-(3-methylphenoxy)-N-methylpyridine-2-carboxamide |
| (30) | 5-bromo-2-methyl-7-trifluoromethyl-1H-benzimidazole | 4-(4-methylphenoxy)-N-methylpyridine-2-carboxamide |
| (31) | 5-chloro-2-methyl-7-trifluoromethyl-1H-benzimidazole | 4-(4-methylphenoxy)pyridine |
| (32) | 5-chloro-2-methyl-7-trifluoromethyl-1H-benzimidazole | 4-(3-methylphenoxy)pyridine |
| (33) | 5-chloro-2-methyl-7-trifluoromethyl-1H-benzimidazole | 3-(3-methylphenoxy)pyridine |

| | A- | ,-B |
|---|---|---|
| (34) | 5-chloro-2-methyl-4-(trifluoromethyl)-1H-benzimidazole | 3-(4-methylphenoxy)pyridine |
| (35) | 5-chloro-2-methyl-4-(trifluoromethyl)-1H-benzimidazole | N-methyl-4-(3-methylphenoxy)pyridine-2-carboxamide |
| (36) | 5-chloro-2-methyl-4-(trifluoromethyl)-1H-benzimidazole | N-methyl-4-(4-methylphenoxy)pyridine-2-carboxamide |
| (37) | 2,5-dimethyl-1H-benzimidazole | 4-(4-methylphenoxy)pyridine |
| (38) | 2,5-dimethyl-1H-benzimidazole | 4-(3-methylphenoxy)pyridine |
| (39) | 2,5-dimethyl-1H-benzimidazole | 3-(3-methylphenoxy)pyridine |
| (40) | 2,5-dimethyl-1H-benzimidazole | 3-(4-methylphenoxy)pyridine |
| (41) | 2,5-dimethyl-1H-benzimidazole | N-methyl-4-(3-methylphenoxy)pyridine-2-carboxamide |
| (42) | 2,5-dimethyl-1H-benzimidazole | N-methyl-4-(4-methylphenoxy)pyridine-2-carboxamide |

-continued
| | A- | ,-B |
|---|---|---|
| (43) | 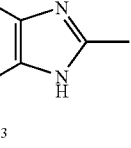 | 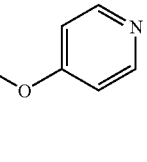 |
| (44) | 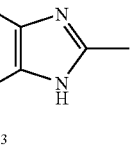 | 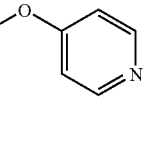 |
| (45) | 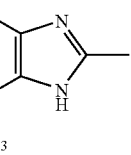 | 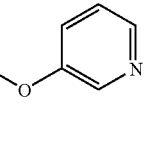 |
| (46) | 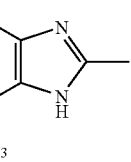 | 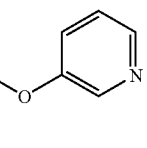 |
| (47) | 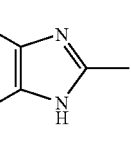 | 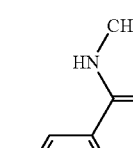 |
| (48) | 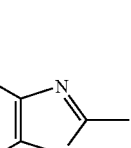 | 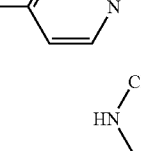 |
| (49) | 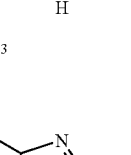 | 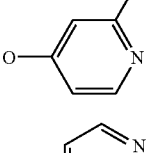 |
| (50) | 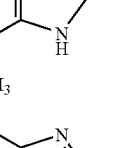 | 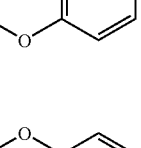 |
| (51) | 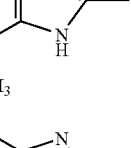 | 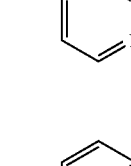 |

-continued

| | A- | ,-B |
|---|---|---|
| (52) | 5-chloro-4-methyl-2-methyl-1H-benzimidazole | 4-methylphenoxy-3-pyridine |
| (53) | 5-chloro-4-methyl-2-methyl-1H-benzimidazole | N-methyl 4-(3-methylphenoxy)pyridine-2-carboxamide |
| (54) | 5-chloro-4-methyl-2-methyl-1H-benzimidazole | N-methyl 4-(4-methylphenoxy)pyridine-2-carboxamide |
| (55) | 5-trifluoromethyl-7-trifluoromethyl-2-methyl-1H-benzimidazole | 4-methylphenoxy-4-pyridine |
| (56) | 5-trifluoromethyl-7-trifluoromethyl-2-methyl-1H-benzimidazole | 3-methylphenoxy-4-pyridine |
| (57) | 5-trifluoromethyl-7-trifluoromethyl-2-methyl-1H-benzimidazole | 3-methylphenoxy-3-pyridine |
| (58) | 5-trifluoromethyl-7-trifluoromethyl-2-methyl-1H-benzimidazole | 4-methylphenoxy-3-pyridine |
| (59) | 5-trifluoromethyl-7-trifluoromethyl-2-methyl-1H-benzimidazole | N-methyl 4-(3-methylphenoxy)pyridine-2-carboxamide |

| | A- | ,-B |
|---|---|---|
| (60) | 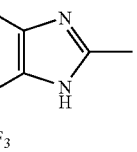 | 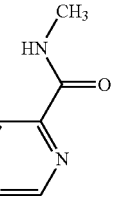 |
| (61) | 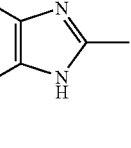 | 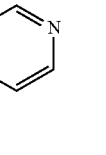 |
| (62) | 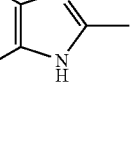 | 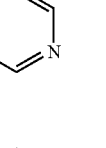 |
| (63) | 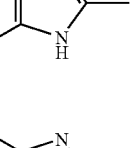 | 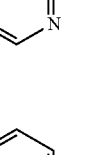 |
| (64) | 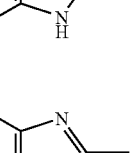 | 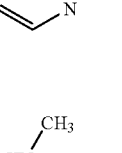 |
| (65) |  | 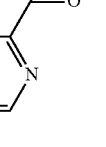 |
| (66) | 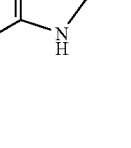 | 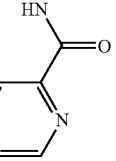 |
| (67) | 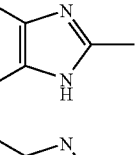 | 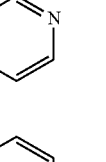 |
| (68) | 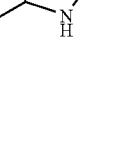 | 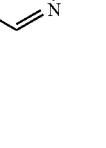 |

-continued

| | A- | ,-B |
|---|---|---|
| (69) | 5-methyl-2-methyl-1H-benzimidazole | 3-(m-tolyloxy)pyridine |
| (70) | 5-methyl-2-methyl-1H-benzimidazole | 3-(p-tolyloxy)pyridine |
| (71) | 5-methyl-2-methyl-1H-benzimidazole | N-methyl-4-(m-tolyloxy)picolinamide |
| (72) | 5-methyl-2-methyl-1H-benzimidazole | N-methyl-4-(p-tolyloxy)picolinamide |
| (73) | 5-trifluoromethyl-6-chloro-2-methyl-1H-benzimidazole | 4-(p-tolyloxy)pyridine |
| (74) | 5-trifluoromethyl-6-chloro-2-methyl-1H-benzimidazole | 4-(m-tolyloxy)pyridine |
| (75) | 5-trifluoromethyl-6-chloro-2-methyl-1H-benzimidazole | 3-(m-tolyloxy)pyridine |
| (76) | 5-trifluoromethyl-6-chloro-2-methyl-1H-benzimidazole | 3-(p-tolyloxy)pyridine |
| (77) | 5-trifluoromethyl-6-chloro-2-methyl-1H-benzimidazole | N-methyl-4-(m-tolyloxy)picolinamide |

| A- | ,-B |
|---|---|
| (78) | 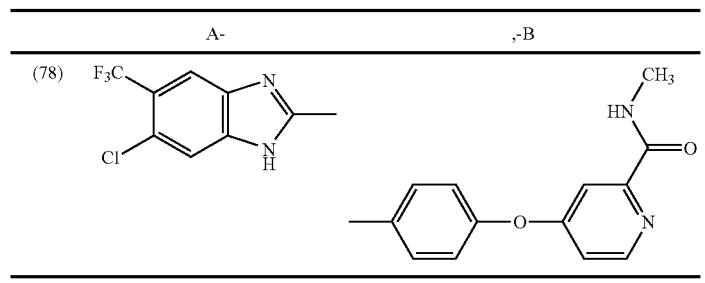 | the tautomeric forms thereof; and the pharmaceutically acceptable derivatives, solvates, salts and stereoisomers thereof, including mixtures thereof in all ratios, and more preferred the salts and/or solvates thereof, and especially preferred the physiologically acceptable salts and/or solvates thereof In a special embodiment, the benzimidazole derivatives according to sub formulae Ia, Ib, Ic, Id and/or Ie additionally comprise one or two substituents selected from the group consisting of $O(CH_2)_nNR^{11}R^{12}$, $NR(CH_2)_nNR^{11}R^{12}$, $O(CH_2)_nOR^{12}$ and $NR^{11}(CH_2)_nOR^{12}$, wherein $R^{11}$, $R^{12}$ are independently selected from a group consisting of H, A, $(CH_2)_mAr^3$ and $(CH_2)_m$Het, or in $NR^{11}R^{12}$, $R^{11}$ and $R^{12}$ form, together with the N-atom they are bound to, a 5-, 6- or 7-membered heterocyclus which optionally contains 1 or 2 additional hetero atoms, selected from N, O an S, and n is 1, 2, 3, 4, 5 or 6.

In this embodiment, the substituents are preferably selected from the group consisting of $HNCH_2CH_2NH_2$, $OCH_2CH_2NH_2$, $HOCH_2CH_2NH$, $OCH_2CH_2NHCH_3$, $N(CH_3)CH_2CH_2NH_2$, $HN(CH_3)CH_2CH_2NH$, $N(CH_3)CH_2CH_2N(CH_3)_2$, $N(CH_3)CH_2CH_2N(CH_3)_2$, $N(CH_3)CH_2CH_2OCH_3$, $OCH_2CH_2N(CH_3)_2$, $OCH_2CH_2N(CH_2CH_3)_2$ and compounds of the formulae

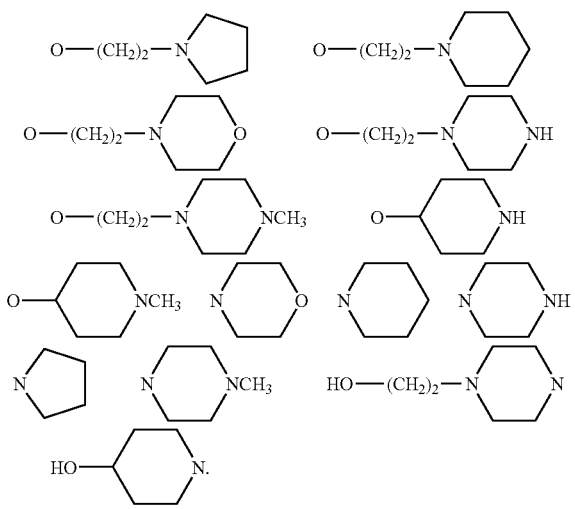

The nomenclature as used herein for defining compounds, especially the compounds according to the invention, is in general based on the rules of the IUPAC-organisation for chemical compounds and especially organic compounds.

Another aspect of the invention relates to a method for producing compounds of formula I, characterised in that a) A compound of formula II

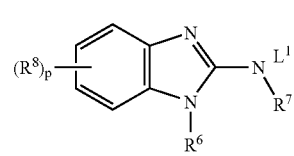

II wherein $L^1$ is H or a metal ion, and $R^6$, $R^7$, $R^8$ and p are as defined above and below, is reacted b) with a compound of formula III,

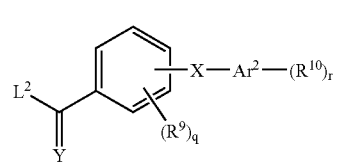

III wherein $L^2$ is Cl, Br, I, OH, an esterified OH-group or a diazonium moiety, and Y, $R^9$, q, X, $Ar^2$, $R^{10}$ and r are as defined above and below, and optionally c) isolating and/or treating the compound of formula I obtained by said reaction with an acid, to obtain the salt thereof.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ by not isolating them from the reaction mixture, but instead immediately converting them further into the compounds of the formula I. On the other hand, it is possible to carry out the reaction stepwise.

The compounds of the formula I and especially the compounds of formula I can preferably be obtained by reacting compounds of the formula II with compounds of the formula III.

In detail, the reaction of the compounds of the formula II with the compounds of the formula III is carried out in the presence or absence of a preferably inert solvent at temperatures between about −20° and about 200° C., preferably between 0° and 100° C. and especially at about room temperature (25° C.). In some cases, it can be advantageous to combine one compound of formula II with one compound of formula III at the lower end of the given temperature range, preferably between −20° and 75° C., more preferred between 0° and 60° C. and especially between 10° and 40° C., for example at about room temperature, and heat the mixture up to a temperature at the upper end of the given temperature range, preferably between 80° and 180°, more preferred between 90° and 150° and especially between 950 and 120°, for example at about 100° or at about 110°.

In general, the compounds of formula II and/or formula III are new. In any case, they can be prepared according to methods known in the art.

In the compounds of formula II, $L^1$ is preferably H or a moiety which activates the amino group it is bonded to, for example a metal ion. Suitable metal ions are preferably selected from the group consisting of alkaline metal ions, alkaline-earth metal ions and aluminium ions. Especially preferred metal ions are alkaline metal ions, of which Li, Na and K are especially preferred. In case of multi-valent metal ions, the metal ions and the compounds of formula II form a complex containing one or more compounds of formula II and one or more metal ions wherein the ratio between compounds of formula II and metal ions is depending on the valency of the metal ion(s) according to the rules of stoichiometry and/or electroneutrality.

In the compounds of formula III, $L^2$ is preferably Cl, Br, I, OH, a reactive derivatized OH-moiety, especially an esterified OH-moiety, for example an OR-moiety wherein R' is an alkyl moiety, preferably an alkyl moiety as described above/below comprising 1 to 10 and more preferably 1 to 6 carbon atoms, or a reactive esterified OH-moiety, for example an alkylsulfonyloxy-moiety comprising 1 to 6 carbon atoms (preferably methylsulfonyloxy) or an arylsulfonyloxy-moiety comprising 6 to 10 carbon atoms (preferably phenyl-oder p-tolylsulfonyloxy), or diazonium moiety, more preferred Cl, Br or I and OR', wherein R' is as defined above/below, and even more preferred OH and OR', wherein R' is preferably selected from the group consisting of methyl, ethyl, n-propyl, isopropyl, n-butyl, isobutyl and t-butyl. Especially preferred as $L^2$ is OH.

The reaction between the compounds of formula II and compounds of formula III can in many cases advantageously be carried out in the presence of an acid binding means, for example one or more bases. Suitable acid binding means are known in the art. Preferred as acid binding means are inorganic bases and especially organic bases. Examples for inorganic bases are alkaline or alkaline-earth hydroxides, alkaline or alkaline-earth carbonates and alkaline or alkaline-earth bicarbonates or other salts of a weak acid and alkaline or alkaline-earth metals, preferably of potassium, sodium, calcium or cesium. Examples for organic bases are triethyl amine, diisopropyl ethyl amine (DIPEA), dimethyl aniline, pyridine or chinoline. If an organic base is used, it is advantageous in general to use a base with a boiling point that is higher than the highest reaction temperature employed during the reaction. Especially preferred as organic base is DIPEA.

In many cases, it is advantageous to carry out the reaction of a compound of formula II with a compound of formula III in the presence of one or more compounds that promote the reaction between the said compounds, for example one or more catalysts and/or one or more compounds that are acting as condensing agents. Suitable compounds in this respect are O-(Benzotriazole-1-yl)-N,N,N',N'-tetramethyluronium hexafluorophosphate tetrafluoroborate (TBTU), O-(Benzotriazole-1-yl)-N,N,N',N'-tetramethyluronium tetrafluoroborate and 1-Hydroxy-1H-benzotriazole (HOBT).

Reaction times are generally in the range between some minutes and several days, depending on the reactivity of the respective compounds and the respective reaction conditions. Suitable reaction times are readily determinable by methods known in the art, for example reaction monitoring. Based on the reaction temperatures given above, suitable reaction times generally lie in the range between 10 min and 36 hrs, preferably 20 min and 24 hrs and especially between 12 min and 12 hrs, for example about 1 h, about 3 hrs, about 6 hrs or about 10 hrs.

Preferably, the reaction of the compounds of the formula II with the compounds of the formula III is carried out in the presence of a suitable solvent, that is preferably inert under the respective reaction conditions. Examples of suitable solvents are hydrocarbons, such as hexane, petroleum ether, benzene, toluene or xylene; chlorinated hydrocarbons, such as trichlorethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, dimethylformamide (DMF) or N-methylpyrrolidinone (NMP); nitriles, such as acetonitrile; sulfoxides, such as dimethyl sulfoxide (DMSO); nitro compounds, such as nitromethane or nitrobenzene; esters, such as ethyl acetate, or mixtures of the said solvents. Polar solvents are in general preferred. Examples for suitable polar solvents are chlorinated hydrocarbons, alcohols, glycol ethers, nitrites, amides and sulfoxides or mixtures thereof. More preferred are amides, especially dimethylformamide (DMF).

If compounds of formula I are desired wherein Y is other than O, it can be advantageous, however, to carry out the reaction of a compound of formula II, wherein Y is O, and a compound of formula III according to the invention to obtain a compound of formula I, wherein Y is O, and to modify or convert the corresponding C=O group (i.e. the C=Y group, wherein Y is O) in the compound of formula I into a C=NR$^{21}$, C=C(R$^{22}$)—NO$_2$, C=C(R$^{22}$)—CN or C=C(CN)$_2$ group according to methods known in the art, for example from Houben-Weyl, Methods of Organic Chemistry.

Especially preferred, the reaction between a compound of formula III, wherein Y is O and $L^2$ is OH, and a compound of formula II, wherein preferably $L^1$ is H, is carried out in the presence of an organic base, such as DIPEA, a polar organic solvent, such as DMF, in the presence of TBTU and HOBT at a temperature between 0° C. and 60° C., for example at about room temperature. In many cases, it can be advantageous to add an acid at a later stage of the reaction, for example after 2-5 h reaction time, to complete the reaction and/or to facilitate the working up procedure.

The compounds of formula II can be obtained according to methods known in the art. In an advantageous manner, they can be readily obtained by reacting a compound of formula IV

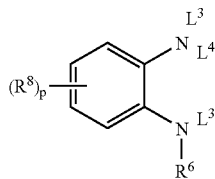

wherein $R^6$, $R^8$ and p are as defined above/below and $L^3$ and $L^4$ are selected independently from each other from the meanings given for $L^2$ and more preferred are hydrogen, with halogen cyanide, preferably bromine cyanide, in the presence of a suitable solvent, such as acetonitrile, water, methanol or mixtures thereof.

Especially preferably, compounds of formula II can readily obtained by adding a compound of formula IV, wherein both $L^3$ and $L^4$ are hydrogen and preferably $R^6$ is also hydrogen, preferably diluted in methanol, to a solution of bromine cyanide, preferably diluted in a mixture of acetonitrile/water, especially preferred a mixture acetonitrile/water about 1:10, to yield a compound of formula V,

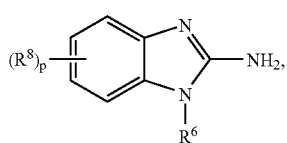

and especially preferred a compound of formula VI

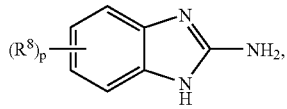

wherein $R^6$ and/or $R^8$ and p are as defined above/below.

This reaction is preferably carried out in a temperature range between 0° C. and 50° C. and especially at about room temperature. Reaction times preferably lie in the range between 2 hours and 4 hrs.

Some of the starting materials of the formula IV are known and preferably commercially available. If they are not known, they can be prepared by methods known per se.

The compounds of formula III can be obtained according to methods known in the art.

If the compound of formula III is a compound according to formula IIIa,

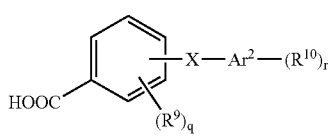

it can be readily obtained in an advantageous manner by reacting a compound of formula VIIIa,

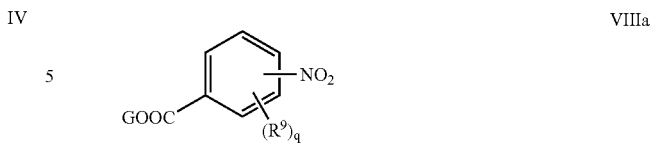

wherein $R^9$ and q are as defined above/below, and wherein G is a protecting group, preferably selected from the meanings given for A and especially is alkyl, for example methyl or ethyl, with a compound of formula IX, $$L^9-X-Ar^2-(R^{10})_r \qquad \text{IX}$$

wherein $L^9$ is H or a metal ion, preferably a metal ion selected from the group consisting of alkaline metal ions, and more preferred is H; and $Ar^2$, $R^{10}$, r and X are as defined above/below, and especially wherein X is $(CHR^{11})_h-Q-(CHR^{12})_i$, wherein $R^{11}$, h, $R^{12}$ and i are defined above/below, and preferably wherein h and/or i are 0, and especially Q is selected from a group consisting of O, S, N—$R^{17}$, $(CHR^{18}-O)_j$, $(CHR^{18}CHR^{19}-O)_j$, CH=N—O, CH—N—$NR^{17}$, $SO_2NR^{17}$, wherein j, $R^{17}$, $R^{18}$ and $R^{19}$ are as defined above/below;

optionally isolating the reaction product, and transferring the obtained reaction product of formula XI

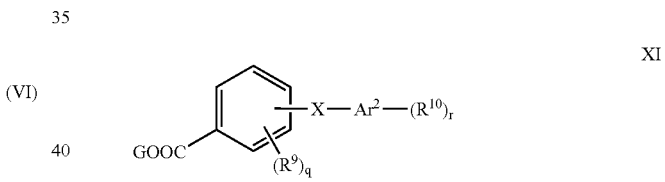

into a compound of formula IIIa, preferably by solvolysing or hydrolysing the COOG-moiety of the compound of formula XI into a COOH-moiety. Methods and reaction conditions for hydrolysing said moiety are known in the art. In general, it is advantageous to carry out said solvolysing or hydrolysing reaction in an acidic or basic medium, in the presence of a suitable solvent. Preferably it is carried out in a basic medium, for example in the presence of one or more bases, preferably inorganic bases such as alkaline or alkaline-earth hydroxides, more preferably NaOH or KOH, in a preferably polar solvent such as water or alcohol, for example alcohols as described above/below, or mixtures thereof. Suitable reaction temperatures usually lie in the range between 0° C. and the boiling point of the solvent chosen and especially at about room temperature. The preferred are hydrolysing conditions, such as carrying out the hydrolysation in ethanol/and water/NaOH, preferably at lower temperatures, for example at temperatures between −20 and 50° C., for example at about 0° C.

$Ar^2$ is preferably pyridinyl. Accordingly, the compound of formula IX is preferably selected from the group consisting of formulae IXa and IXb,

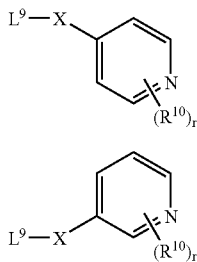

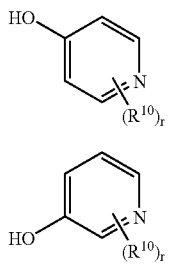

wherein $L^9$, X, $R^{10}$ and r are as defined above, and especially preferred from the group consisting of formulae IXc and IXd,

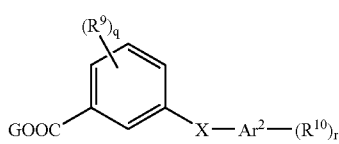

wherein $R^{10}$ and r are as defined above.

Accordingly, in formulae IIIa, IX, IXa, IXb and XI, the bridging group X is preferably O, S, $OCH_2$ and $OCH_2CH_2$ and especially is O.

In the formulae IX, IXa and IXb, $L^9$ is preferably H.

In general, this reaction is advantageous to produce compounds of formula IIIaa,

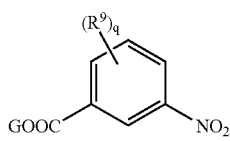

wherein $R^9$, q, X, $Ar^2$, $R^{10}$ r and G and are as defined above/below.

To obtain compounds of formula IIIaa, it is reasonable to employ a compound of formula VIII that is selected from the compounds of formula VIIIa,

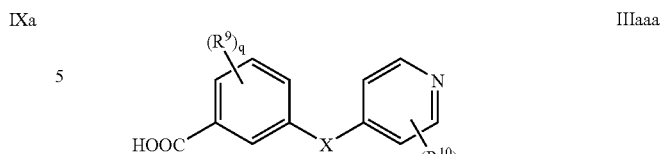

and proceed the reaction as described above/below.

Accordingly, by starting from a compound of formula VIIIa and a compound of formula IXa, the reaction preferably leads to compounds of formula IIIaaa,

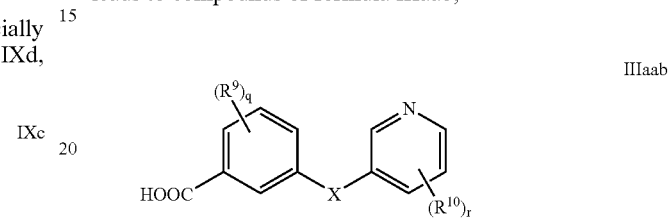

wherein $R^9$, q, X, $R^{10}$ and r are as defined above/below.

Accordingly, by starting from a compound of formula VIIIa and a compound of formula IXb, the reaction preferably leads to compounds of formula IIIaab,

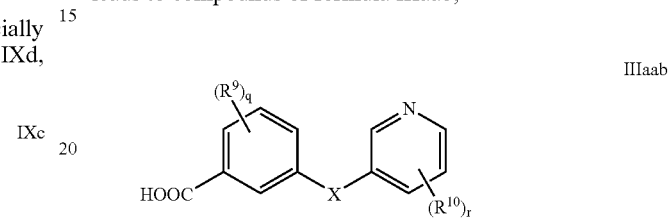

wherein $R^9$, q, X, $R^{10}$ and r are as defined above/below.

Accordingly, by starting from a compound of formula VIIIa and a compound of formula IXc, the reaction preferably leads to compounds of formula IIIaac,

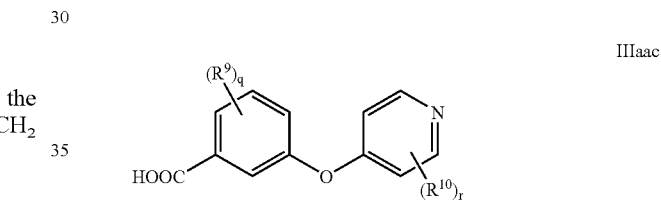

wherein $R^9$, q, $R^{10}$ and r are as defined above/below.

Accordingly, by starting from a compound of formula VIIIa and a compound of formula IXd, the reaction preferably leads to compounds of formula

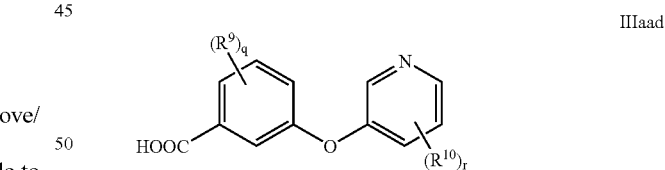

wherein $R^9$, q, $R^{10}$ and r are as defined above/below.

Some of the starting materials of the formula VIII and/or the formula IX are known and preferably commercially available. If they are not known, they can be prepared by methods known per se.

The reaction between the compound of formula VIII and IX is preferably carried out in the temperature range between 0° and 250°, more preferred room temperature and 200°, for example at about 120°, at about 150° or at about 180°. Reaction times depend on the respective reactants and the respective reaction temperature, but generally lie in the range between 30 min and 36 hrs, preferably 3 hrs and 24 hrs, more preferably 8 hrs and 20 hrs for example about 10 hrs, about 16 hrs or about 18 hrs.

The reaction can be carried out in the absence of solvent or preferably in the presence of a solvent, preferable a solvent that is inert under the respective reaction conditions. Suitable inert solvents for carrying out the reaction are known in the art. Examples for suitable solvents are high boiling aliphatic hydrocarbons, high boiling aromatic carbons, for example toluene, xylenes, high boiling chlorinated hydrocarbons, such as trichloroethylene, tetrachloroethanes, pentachloroethanes and hexachloroethanes; high boiling ethers, such as ethylene glycol and propylene glycols; glycol ethers, such as ethylene glycol monomethyl or monoethyl ether or ethylene glycol dimethyl ether (diglyme); amides, such as acetamide, dimethylacetamide, dimethylformamide (DMF) or N-methyl pyrrolidone (NMP); sulfoxides, such as dimethyl sulfoxide (DMSO); or mixtures of the said solvents. Preferred are amides, especially dimethylformamide (DMF).

Preferably, the reaction is carried out in the presence of a base. Suitable bases are known in the art. Preferred bases are organic bases and especially inorganic bases. Examples for inorganic bases are alkaline or alkaline-earth hydroxides, alkaline or alkaline-earth carbonates and alkaline or alkaline-earth bicarbonates or other salts of a weak acid and alkaline or alkaline-earth metals, preferably of potassium, sodium, calcium or cesium. Preferred inorganic bases are $K_2CO_3$, $Na_2CO_3$, $MgCO_3$, $CaCO_3$, NaOH and KOH, especially preferred is $K_2CO_3$. Examples for organic bases are triethyl amine, diisopropyl ethyl amine (DIPEA), dimethyl aniline, pyridine or chinoline. If an organic base is used, it is advantageous in general to use a base with a boiling point that is higher than the highest reaction temperature employed during the reaction.

Alternatively, if the compound of formula III is a compound according to formula IIIb,

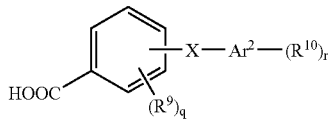

IIIb it can be readily obtained in an advantageous manner by reacting a compound of formula VIIIb,

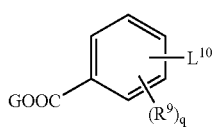

VIIIb wherein $R^9$, q and G are as defined above/below and wherein $L^{10}$ is selected independently from the meanings given for $L^2$. Preferably, $L^{10}$ is halogen. More preferred, $L^{10}$ is selected from the group consisting of Cl, Br and I. Especially preferred, $L^{10}$ is Cl.

with a compound of formula IXbβ,

IXbβ wherein $L^{11}$ is H or a metal ion, preferably a metal ion, more preferred a metal ion selected from the group consisting of alkaline metal ions, and especially is H; and $Ar^2$, $R^{10}$, r and X are as defined above/below, and especially wherein X is $(CHR^{11})_h$—Q—$(CHR^{12})_i$, CH=N—O, CH=N—$NR^{17}$, $SO_2NR^{17}$, wherein Q, h, i, $R^{11}$, $R^{12}$ and $R^{17}$ are as defined above/below; and especially X is O.

optionally isolating the reaction product, and transferring the obtained reaction product of formula XIb

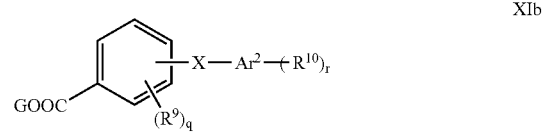

XIb into a compound of formula IIIa, preferably by solvolysing or hydrolysing the the COOG-moiety of the compound of formula XI into a COOH-moiety, preferably under conditions as described above.

$Ar^2$ is preferably pyridinyl. Accordingly, the compound of formula IXbβ is preferably selected from the group consisting of formulae IXe and IXf,

IXe

IXf wherein $L^{11}$, X, $R^{10}$ and r are as defined above, and especially preferred from the group consisting of formulae IXg and IXh,

IXg

IXh wherein $R^{10}$ and r are as defined above.

Accordingly, in formulae IIIb, IXb, IXbβ, IXe, IXf and XIb, the bridging group X is preferably O, S, $OCH_2$ and $OCH_2CH_2$ and especially is O.

In general, this alternative reaction is advantageous to produce compounds of formula IIIbb,

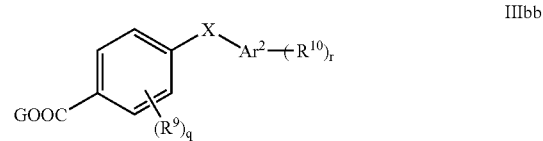

IIIbb wherein $R^9$, q, X, $Ar^2$, $R^{10}$, r and G are as defined above/below.

To obtain compounds of formula IIIbb, it is reasonable to employ a compound of formula VIIIb that is selected from the compounds of formula VIIIbb,

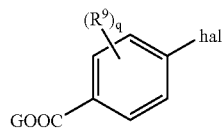

VIIIbb wherein hal and G are as defined above/below, and especially hal is Cl; and proceed the alternative reaction as described above/below.

Accordingly, by starting from a compound a formula VIIIbb and a compound of formula VIIIe, the reaction preferably leads to compounds of formula IIIbbe,

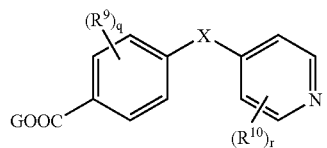

IIIbbe wherein $R^9$, q, X, $R^{10}$, r and G are as defined above/below.

Accordingly, by starting from a compound of formula VIIIbb and a compound of formula IXf, the reaction preferably leads to compounds of formula IIIbbf,

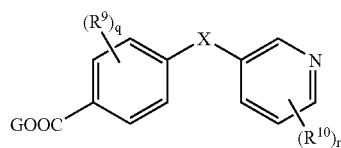

IIIbbf wherein G, $R^9$, q, X, $R^{10}$ and r are as defined above/below.

Accordingly, by starting from a compound of formula VIIIbb and a compound of formula IXg, the reaction preferably leads to compounds of formula IIIbbg,

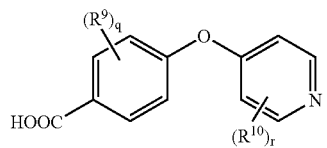

IIIbbg wherein $R^9$, q, $R^{10}$ and r are as defined above/below.

Accordingly, by starting from a compound of formula VIIIb and a compound of formula IXh, the reaction preferably leads to compounds of formula IIIbbh,

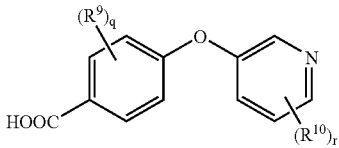

IIIbbh wherein $R^9$, q, $R^{10}$ and r are as defined above/below.

Some of the starting materials of the formula VIIIb and/or the formula IXbβ are known and preferably commercially available. If they are not known, they can be prepared by methods known per se.

The reaction between the compound of formula VIIIb and IXbβ is preferably carried out in the temperature range between 0° and 250°, more preferred 50° and 220°, for example at about 90°, at about 120°, at about 160°, at about 180° or at about 200°. Reaction times depend on the respective reactants and the respective reaction temperature, but generally lie in the range between 10 min and 24 hrs, preferably 30 min and 12 hrs, more preferably 1 h and 6 hrs for example about 1.5 hrs, about 3 hrs, about 4 hrs or about 5 hrs.

The reaction can be carried out in the absence or the presence of a solvent, preferable a solvent that is inert under the respective reaction conditions. Suitable inert solvents for carrying out the reaction are known in the art. Examples for suitable solvents are aliphatic hydrocarbons, aromatic carbons, for example toluene and xylenes, chlorinated hydrocarbons, such as dichlormethane, trichloromethane trichloroethylene, tetrachloroethanes, pentachloroethanes and hexachloroethanes; ethers, such as diethylether, tert.-butyl methyl ether, ethylene glycol and propylene glycols; glycol ethers, such as ethylene glycol monomethyl or monoethyl ether or ethylene glycol dimethyl ether (diglyme); nitriles, such as acetonitrile, amides such as acetamide, dimethylformamide (DMF) or N-methylpyrrolidone (NMP); sulfoxides, such as dimethyl sulfoxide (DMSO); or mixtures of the said solvents.

Preferably, the reaction is carried out in the presence of a catalyst. Suitable catalysts are known in the art. Preferred catalytic active metals and especially copper.

Preferably, the reaction is carried out by heating up a reaction mixture comprising one compound of formula VIIIb and one compound of formula IXb to a suitable reaction temperature, which preferably lies at the upper end of the given temperature ranges and more preferred is in the range between 150° and 200°, for example at about 180°, preferably in the presence of the suitable catalyst and especially in the presence of copper. Reaction times at this temperature are preferably as given above and especially in the range between 1 h and 5 hrs, for example about 3 hrs. Preferably, the reaction mixture is then allowed to cool down to a temperature in the lower range of the given temperature, more preferred to a temperature in the range between 50° and 150°, for example to about 90°. Preferably, a suitable solvent, especially tert.-butyl methyl ether, is then added and the reaction mixture is preferably kept at about the same temperature for some more time, preferably for 30 min to 2 hrs and more preferred for about one hour.

As a preferred further alternative, if the compound of formula III is a compound according to formula IIIc,

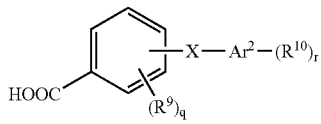

IIIc it can be readily obtained in an advantageous manner by reacting a compound of formula VIIIb,

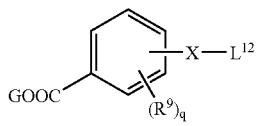

VIIIc wherein $R^9$, q and G are as defined above/below, X is (CH $R^{11}$)$_h$—Q—(CHR$^{12}$)$_i$, CH=N—O, CH=N—NR$^{17}$, SO$_2$NR$^{17}$, wherein Q, h, i, $R^{11}$, $R^{12}$ and $R^{17}$ are as defined above/below and especially X is O; and wherein $L^{12}$ is selected independently from the meanings given for $L^1$ and especially is H;

with a compound of formula IXc,

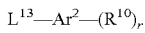

IXc wherein $L^{13}$ is a suitable leaving group, preferably Cl, Br, I, an esterified OH-group or a diazonium moiety, more preferred Cl, Br or I and especially is Cl; and Ar$^2$, $R^{10}$ and r are as defined above/below, optionally isolating the reaction product, and transferring the obtained reaction product of formula XIc XIc

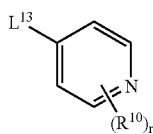

into a compound of formula IIIc, preferably by solvolysing or hydrolysing the the COOG-moiety of the compound of formula XIc into a COOH— moiety, preferably under conditions as described above.

Ar$^2$ is preferably pyridinyl. Accordingly, the compound of formula IXc is preferably selected from the group consisting of formulae IXce and IXcf,

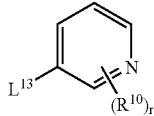

IXce

-continued

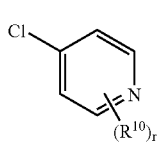

IXcf wherein $L^{13}$, $R^{10}$ and r are as defined above, and especially preferred from the group consisting of formulae IXcg and IXch,

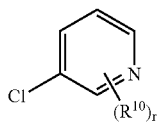

IXcg

IXch wherein $R^{10}$ and r are as defined above.

In general, this alternative reaction is advantageous to produce compounds of formula IIIcc,

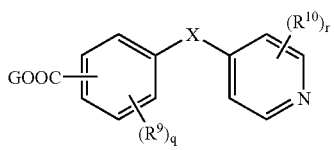

IIIcc wherein $R^9$, q, X, Ar$^2$, $R^{10}$, r and G are as defined above/below, and especially compounds of formula IIIccc,

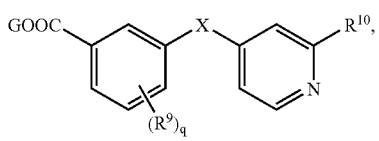

IIIccc wherein $R^9$, q, X, $R^{10}$ and G are as defined above/below and especially wherein $R^9$, q, X, and G are as defined above/below and $R^{10}$ is unsubstituted or preferably substituted carbamoyl.

The reaction between a compound of formula VIIIc and the compound of formula IXc can be performed under reaction times and reaction conditions known in the art. Advantageously, the reaction can be in the absence or preferably in the presence of the suitable solvent, preferably a polar solvent, for example polar solvents as described above. Preferably, the reaction is carried out in the presence of DMF as solvent. The reaction is preferably carried out in a temperature range between 0° C. and 120° C., more preferred 25° C. and 100° C. and especially 45° C. and 80° C. Reaction times preferably lie in the range between 15 minutes and 48 hrs, preferably 1 h and 36 hrs and especially 6 hrs and 30 hrs. In many cases, it can be advantageous to combine the compound of formula VIIIc and the compound of formula IXc at a temperature at the lower end of the given ranges for a reaction time at the lower end of the given ranges, and then heating up the reaction mixture to a temperature at the upper end of the given ranges for a reaction time given at the upper end of the reaction time ranges. Especially preferred, the compound of formula VIIIc and the compound of formula IXc are combined and heated to a temperature of about 45° C. for a reaction time between 5 min and 30 min, then heated to a temperature of about 80° C. for a reaction time between 20 and 30 hrs.

Also alternatively, if the compound III is a compound according to formula IIId,

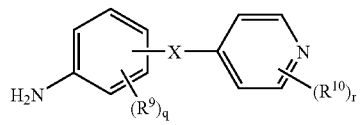

it can be readily obtained in an advantageous manner by reacting a compound of formula XII

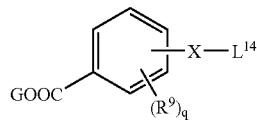

wherein $L^{14}$ is H or a metal ion, preferably a metal ion selected from the group consisting of alkaline metal ions, alkaline-earth metal ions and aluminium ions, especially preferred alkaline metal ions, of which Li, Na and K are especially preferred, and even more preferred is H; and $R^9$, q and X are as defined above/below, and especially wherein X is $(CHR^{11})_h$—Q—$(CHR^{12})_i$, wherein $R^{11}$, h, $R^{12}$ and i are defined above/below, and wherein h and/or i preferably are 0, and Q is selected from a group consisting of O, S, N—$R^{17}$, $(CHR^{18}$—O$)_j$, $(CHR^{18}CHR^{19}$—O$)_j$, CH=N—O, CH=N—$NR^{17}$, $SO_2NR^{17}$, wherein j, $R^{17}$, $R^{18}$ and $R^{19}$ are as defined above/below;

with a compound of formula XIII,

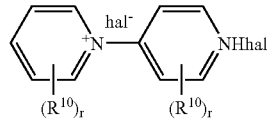

wherein hal is independently selected from the group consisting of Cl, Br and I, the residue $R^{10}$ are the same or different and have the meanings given above/below and preferably have both the same meaning, and the indices r are the same or different and have the meanings given above/below and preferably are the same, optionally isolating the reaction product, and transferring the obtained reaction product of formula XIV

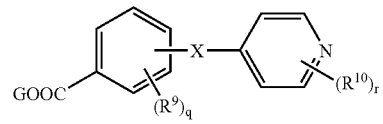

into a compound of formula IIId, preferably by solvolysing or hydrolysing the COOG-moiety of the compound of formula XIV into a COOH— moiety, preferably under conditions as described above.

The reaction between the compound of formula XII and XIII is preferably carried out in the temperature range between 0° and 250°, more preferred room temperature and 200°, for example at about 120°, at about 150° or at about 180°. Reaction times depend on the respective reactants and the respective reaction temperature, but generally lie in the range between 30 min and 24 hrs, preferably one hour and 12 hrs, for example about 2 hrs, about 3 hrs or about 6 hrs. The reaction can be carried out in the absence of solvent or in the presence of a solvent, preferable a solvent that is inert under the respective reaction conditions. Suitable inert solvents for carrying out the reaction are known in the art.

Some of the starting materials of the formula XII and/or the formula XIII are known and preferably commercially available. If they are not known, they can be prepared by methods known per se.

In the compounds III, IIIa, IIIaa, IIIaaa, IIIaab, IIIb, IIIbb, IIIbbc, IIIbbf, IIIc, IIIcc, IIIccc, IIId, VIIIc, IX, IXa, IXb, IXbβ, IXe, IXf, XI, XII and/or XIV, the bridging group X is preferably O, S, $OCH_2$ and $OCH_2CH_2$, more preferably O or $CH_2$ and especially is O.

In the compounds IIId, XIII and XIV, r is preferably in each case identical and even more preferred in each case 0.

In the formula XII, $L^{10}$ is preferably H or selected from the group consisting of Na and K and especially preferred is H.

Independently of the chosen reaction route, it is in many cases possible or even feasible to introduce residues $R^8$, $R^9$ and/or $R^{10}$ into one or more of the compounds described above, or, if the compound already comprises one or more residues $R^8$, $R^9$ and/or $R^{10}$, to introduce additional residues $R^8$, $R^9$ and/or $R^{10}$ into said compound. The introduction of additional residues can be readily performed by methods known in the art and especially by aromatic substitution, for example nucleophilic aromatic substitution or electrophilic aromatic substitution. For example, in compounds, wherein the benzimidazole-moiety and/or $Ar^2$ comprise one or more halogen and preferably fluorine substituents, one or more of the halogen/fluorine substituents can be easily substituted by hydroxy, thio and/or amino substituted hydrocarbons, preferably selected from the group consisting of HO $(CH_2)_nNR^{11}R^{12}$, $HO(CH_2)_nO(CH_2)_kNR^{11}R^{12}$, $HO(CH_2)_n NR^{11}(CH_2)_kOR^{12}$, $HO(CH_2)_nNR^{11}(CH_2)_kNR^{11}R^{12}$, HO $(CH_2)_nCOOR^{13}$, $HO(CH_2)_nS(O)_uR^{13}$ $HNR^{11}(CH_2)_nNR^{11}R^{12}$, $HNR^{11}(CH_2)_nO(CH_2)_kNR^{11}R^{12}$, $HNR^{11}(CH_2)_nNR^{11}$ $(CH_2)_kOR^{12}$, $HNR^{11}(CH_2)_nNR^{11}(CH_2)_kNR^{11}R^{12}$, $HNR^{11}$ $(CH_2)_nCOOR^{13}$ and $HNR^{11}(CH_2)_nS(O)_uR^{13}$ wherein $R^{11}$, $R^{12}$ and $R^{13}$ are defined as above and n is as defined above, preferably n is 0, 1 or 2 and especially is 0, k is 1 to 4 and preferably 1 or 2, and u is preferably 2. In this embodiment $R^{11}$, $R^{12}$ and $R^{13}$ are more preferably selected independently from each other from the group consisting of H, methyl and ethyl. Even more preferred, the hydroxy, thio and/or amino substituted hydrocarbons are selected from the group consisting of $NH_3$, $HN(CH_3)_2$, $NH_2CH_3$, $HN(C_2H_5)_2$, $H_2NCH_2CH_2NH_2$, $HOCH_2CH_2NH_2$, $HOCH_2CH_2NHCH_3$, $HN(CH_3)CH_2CH_2NH_2$, $HN(CH_3)CH_2CH_2N(CH_3)_2$, $HN(CH_3)CH_2CH_2N(CH_3)_2$, $HN(CH_3)CH_2CH_2OCH_3$, $HOCH_2CH_2N(CH_3)_2$, $HOCH_2CH_2N(CH_2CH_3)_2$, $HSCH_3$, $HSC_2H_5$, and compounds of the formulae

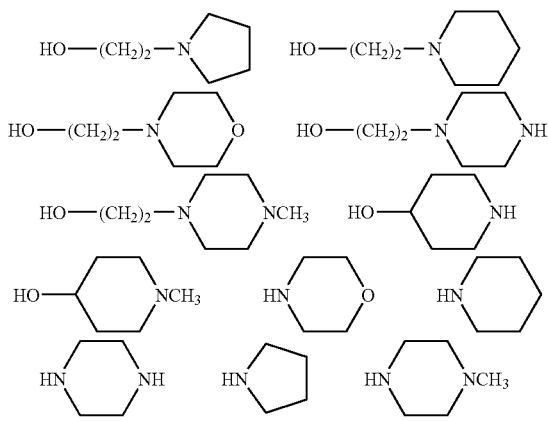

or salts and especially metal salts thereof.

On the other hand, it is in many cases possible or even feasible to modify or derivatize one or more of the residue is $R^8$, $R^9$ and $R^{10}$ into residues $R^8$, $R^9$ and/or $R^{10}$ other than the ones originally present. For example, $CH_3$-groups can be oxidised into aldehyde groups or carboxylic acid groups, thio atom containing groups, for example S-alkyl or S-aryl groups, can be oxidised into $SO_2$-alkyl or $SO_2$-aryl groups, respectively, carboxylic acid groups can be derivatized to carboxylic acid ester groups or carboxylic acid amide groups, and carboxylic acid ester groups or carboxylic acid amide groups can be hydrolysed into the corresponding carboxylic acid groups. Methods for performing such modifications or derivatizations are known in the art, for example from Houben-Weyl, Methods of Organic Chemistry.

Every reaction step described herein can optionally be followed by one or more working up procedures and/or isolating procedures. Suitable such procedures are known in the art, for example from standard works, such as Houben-Weyl, Methoden der organischen Chemie [Methods of Organic Chemistry], Georg-Thieme-Verlag, Stuttgart). Examples for such procedures include, but are not limited to evaporating a solvent, distilling, crystallization, fractionised crystallization, extraction procedures, washing procedures, digesting procedures, filtration procedures, chromatography, chromatography by HPLC and drying procedures, especially drying procedures in vacuo and/or elevated temperature.

A base of the formula I can be converted into the associated acid-addition salt using an acid, for example by reaction of equivalent amounts of the base and the acid in a preferably inert solvent, such as ethanol, followed by evaporation. Suitable acids for this reaction are, in particular, those which give physiologically acceptable salts. Thus, it is possible to use inorganic acids, for example sulfuric acid, sulfurous acid, dithionic acid, nitric acid, hydrohalic acids, such as hydrochloric acid or hydrobromic acid, phosphoric acids, such as, for example, orthophosphoric acid, sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, hexanoic acid, octanoic acid, decanoic acid, hexadecanoic acid, octadecanoic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, trimethoxybenzoic acid, adamantanecarboxylic acid, p-toluenesulfonic acid, glycolic acid, embonic acid, chlorophenoxyacetic acid, aspartic acid, glutamic acid, proline, glyoxylic acid, palmitic acid, parachlorophenoxyisobutyric acid, cyclohexanecarboxylic acid, glucose 1-phosphate, naphthalenemono- and -disulfonic acids or laurylsulfuric acid. Salts with physiologically unacceptable acids, for example picrates, can be used to isolate and/or purify the compounds of the formula I. On the other hand, compounds of the formula I can be converted into the corresponding metal salts, in particular alkali metal salts or alkaline earth metal salts, or into the corresponding ammonium salts, using bases (for example sodium hydroxide, potassium hydroxide, sodium carbonate or potassium carbonate). Suitable salts are furthermore substituted ammonium salts, for example the dimethyl-, diethyl- and diisopropylammonium salts, monoethanol-, diethanol- and diisopropanolammonium salts, cyclohexyl- and dicyclohexylammonium salts, dibenzylethylenediammonium salts, furthermore, for example, salts with arginine or lysine.

On the other hand, if desired, the free bases of the formula I can be liberated from their salts using bases (for example sodium hydroxide, potassium hydroxide, sodium carbonate or potassium carbonate).

The invention relates to compounds of the formula I and physiologically acceptable salts and solvates thereof as medicaments.

The invention also relates to the compounds for the formula I and physiologically acceptable salts and solvates thereof as kinase inhibitors.

The invention furthermore relates to the use of the compounds of the formula I and/or physiologically acceptable salts and/or solvates thereof for the preparation of pharmaceutical compositions and/or pharmaceutical preparations, in particular by non-chemical methods. The invention furthermore relates to the use of the compounds of the formula I and/or physiologically acceptable salts and/or solvates thereof for the preparation of pharmaceutical compositions and/or pharmaceutical preparations, in particular by non-chemical methods. In this cases, one or more compounds according to the invention can be converted into a suitable dosage form together with at least one solid, liquid and/or semi-liquid excipient or adjuvant and, if desired, in combination with one or more further active ingredients.

The invention further relates to the use of one or more of the compounds according to the invention, selected from the group consisting of compounds of the formula I as free bases, pharmaceutically acceptable derivatives, preferably solvates of compounds of the formula and salts of compounds of formula I, for the production of pharmaceutical compositions and/or pharmaceutical preparations, in particular by a non-chemical route. In general, non-chemical routes for the production of pharmaceutical compositions and/or pharmaceutical preparations comprise processing steps on suitable mechanical means known in the art that transfer one or more compounds according to the invention into a dosage form suitable for administration to a patient in need of such a treatment. Usually, the transfer of one or more compounds according to the invention into such a dosage form comprises the addition of one or more compounds, selected from the group consisting of carriers, excipients, auxiliaries and pharmaceutical active ingredients other than the compounds according to the invention. Suitable processing steps include, but are not limited to combining, milling, mixing, granulating, dissolving, dispersing, homogenizing, casting and/or compressing the respective active and non-active ingredients. In this respect, active ingredients are preferably at least one compound according to this invention and one or more additional compounds other than the compounds according to the invention, which show valuable pharmaceutical properties, preferably those pharmaceutical active agents other than the compounds according to the invention which are disclosed herein.

The process for preparing pharmaceutical compositions and/or pharmaceutical preparations preferably comprises one or more processing steps, selected from the group consisting of combining, milling, mixing, granulating, dissolving, dispersing, homogenizing and compressing. The one or more processing steps are preferably performed on one or more of the ingredients which are to form the pharmaceutical composition and/or pharmaceutical preparation preferably according to the invention. Even more preferred, said processing steps are performed on two or more of the ingredients which are to form the pharmaceutical composition and/or pharmaceutical preparation, said ingredients comprising one or more compounds according to the invention and, additionally, one or more compounds, preferably selected from the group consisting of active ingredients other than the compounds according to the invention, excipients, auxiliaries, adjuvants and carriers. Mechanical means for performing said processing steps are known in the art, for example from Ullmann's Encyclopedia of Industrial Chemistry, 5th Edition.

Preferably, one or more compounds according to the invention are converted into a suitable dosage form together with at least one compound selected from the group consisting of excipients, auxiliaries, adjuvants and carriers, especially solid, liquid and/or semi-liquid excipients, auxiliaries, adjuvants and carriers, and, if desired, in combination with one or more further active ingredients.

Suitable dosage forms include, but are not limited to tablets, capsules, semi-solids, suppositories, aerosols, which can be produced according to methods known in the art, for example as described below:

| | |
|---|---|
| tablets | mixing of active ingredient/s and auxiliaries, compression of said mixture into tablets (direct compression), optionally granulation of part of mixture before compression |
| capsules | mixing of active ingredient/s and auxiliaries to obtain a flowable powder, optionally granulating powder, filling powders/granulate into opened capsules, capping of capsules |
| semi-solids (ointments, gels, creams) | dissolving/dispersing active ingredient/s in an aqueous or fatty carrier; subsequent mixing of aqueous/fatty phase with complementary fatty resp. aqueous phase, homogenisation (creams only) |
| suppositories (rectal and vaginal) | dissolving/dispersing active ingredient/s in carrier material liquified by heat (rectal: carrier material normally a wax; vaginal: carrier normally a heated solution of a gelling agent), casting said mixture into suppository forms, annealing and withdrawal suppositories from the forms |
| aerosols: | dispersing/dissolving active agent/s in a propellant, bottling said mixture into an atomizer |

The invention thus relates to pharmaceutical compositions and/or pharmaceutical preparations comprising at least one compound of the formula I and/or one of its physiologically acceptable salts and/or solvates and especially to pharmaceutical compositions and/or pharmaceutical preparations comprising at least one compound of the formula I and/or one of its physiologically acceptable salts and/or solvates.

Preferably, the pharmaceutical compositions and/or pharmaceutical preparations according to the invention contain a therapeutic effective amount of one or more compounds according to the invention. Said therapeutic effective amount of one or more of the compounds according to the invention is known to the skilled artisan or can be easily determined by standard methods known in the art. For example, the compounds according to the invention can be administered to a patient in an analogous manner to other compounds that are effective as kinase inhibitors, preferably as raf-kinase inhibitors, especially in an analogous manner to the compounds described in WO 00/42012 (Bayer). Usually, suitable doses that are therapeutically effective lie in the range between 0.0005 mg and 1000 mg, preferably between 0.005 mg and 500 mg and especially between 0.5 and 100 mg per dose unit. The daily dose comprises preferably more than 0.001 mg, more preferred more than 0.01 mg, even more preferred more than 0.1 mg and especially more than 1.0 mg, for example more than 2.0 mg, more than 5 mg, more than 10 mg, more than 20 mg, more than 50 mg or more than 100 mg, and preferably less than 1500 mg, more preferred less than 750 mg, even more preferred less than 500 mg, for example less than 400 mg, less than 250 mg, less than 150 mg, less than 100 mg, less than 50 mg or less than 10 mg.

The specific dose for the individual patient depends, however, on the multitude of factors, for example on the efficacy of the specific compounds employed, on the age, body weight, general state of health, the sex, the kind of diet, on the time and route of administration, on the excretion rate, the kind of administration and the dosage form to be administered, the pharmaceutical combination and severity of the particular disorder to which the therapy relates. The specific therapeutic effective dose for the individual patient can readily be determined by routine experimentation, for example by the doctor or physician which advises or attends the therapeutic treatment.

However, the specific dose for each patient depends on a wide variety of factors, for example on the efficacy of the specific compound employed, on the age, body weight, general state of health, sex, on the diet, on the time and method of administration, on the rate of excretion, medicament combination and severity of the particular illness to which the therapy applies. Parenteral administration is preferred. Oral administration is especially preferred.

These compositions and/or preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or vaseline. Examples for suitable dosage forms, which are especially suitable for oral administration are, in particular, tablets, pills, coated tablets, capsulees, powders, granules, syrups, juices or drops. Further examples for suitable dosage forms, which are especially suitable for rectal administration are suppositories, further examples for suitable dosage forms, which are especially suitable for parenteral administration are solutions, preferably oil-based or aqueous solutions, furthermore suspensions, emulsions or implants, and suitable for topical application are ointments, creams or powders. The novel compounds may also be lyophilised and the resultant lyophilisates used, for example, for the preparation of injection preparations. The compositions and/or preparations indicated may be sterilized and/or comprise assistants, such as lubricants, preservatives, stabilizers and/or wetting agents, emulsifiers, salts for modifying the osmotic pressure, buffer substances, dyes and flavors and/or one or more further active ingredients, for example one or more vitamins.

For administration as an inhalation spray, it is possible to use sprays in which the active ingredient is either dissolved or suspended in a propellant gas or propellant gas mixture (for example $CO_2$ or chlorofluorocarbons). The active ingredient is advantageously used here in micronized form, in which case one or more additional physiologically acceptable solvents may be present, for example ethanol. Inhalation solutions can be administered with the aid of conventional inhalers.

The compounds of the formula I and their physiologically acceptable salts and solvates and especially the compounds of formula I and their physiologically acceptable salts and solvates can be employed for combating one or more diseases, for example allergic diseases, psoriasis and other skin diseases, especially melanoma, autoimmune diseases, such as, for example, rheumatoid arthritis, multiple sclerosis, Crohn's disease, diabetes mellitus or ulcerative colitis.

In general, the substances according to the invention are preferably administered in doses corresponding to the compound rolipram of between 1 and 500 mg, in particular between 5 and 100 mg per dosage unit. The daily dose is preferably between about 0.02 and 10 mg/kg of body weight. However, the specific dose for each patient depends on a wide variety of factors, for example on the efficacy of the specific compound employed, on the age, body weight, general state of health, sex, on the diet, on the time and method of administration, on the excretion rate, medicament combination and severity of the particular illness to which the therapy applies.

The compounds of the formula I according to claim 1 and/or their physiologically acceptable salts are also used in pathological processes which are maintained or propagated by angiogenesis, in particular in tumours, restenoses, diabetic retinopathy, macular degenerative disease or rheumatoid arthritis.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with pharmaceutically active agents other than the compounds according to the invention, particularly other anti-metastatic, antitumor or anti-angiogenic agents. Angiostatic compounds of interest include angiostatin, enclostatin, carboxy terminal peptides of collagen alpha (XV), etc. Cytotoxic and cytostatic agents of interest include adriamycin, aleran, Ara-C, BICNU, busulfan, CNNU, cisplatinum, cytoxan, daunorubicin, DTIC, 5-FU, hydrea, ifosfamicle, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

The compounds of the invention preferably show antiproliferative effects, for example in an in vivo xenograft tumor model. The subject compounds can be administered to a subject having a hyperproliferative disorders, e.g., to inhibit tumor growth, to decrease inflammation associated with a lymphoproliferative disorder, to inhibit graft rejection, or neurological damage due to tissue repair, etc. The present compounds can be useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g., to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

Furthermore, the compounds according the invention preferably can be utilized in the treatment of infectious diseases of diverse genesis.

Infections according the invention include, but are not limited to infections caused by pathogenic microorganisms, such as bacteria, fungi, viruses and protozoans, for example influenza (Pleschka, S. et al. Nature Cell Biol. 2001, 3, page 301-305), retroviruses, for example HIV infection (Yang, X. et al. J. Biol. Chem. 1999, 274, page 27981-27988; Popik, W et al Mol Cel Biol. 1996, 16, page 6532-6541), Hepatitis B (Benn, J et al., Proc. Natl. Acad. Sci. 1995, 92, page 11215-11219), Hepatitis C (Aoki et al. J. Virol. 2000, 74, page 1736-1741), papillomavirus, parainfluenza, rhinoviruses, adenoviruses, *Heliobacter pylori*, and viral and bacterial infections of the skin (e.g. cold sores, warts, chickenpox, molluscum, contagiosum, herpes zoster, boils, cellulitis, erysipelas, impetigo, tinea, Althlete's foot and ringworm).

Furthermore, the compounds according the invention preferably show anti-angiogenic properties.

Thus, compounds of the present invention can be advantageously employed in the treatment of one or more diseases afflicting mammals which are characterized by cellular proliferation in the area of disorders associated with neo-vascularization and/or vascular permeability including blood vessel proliferative disorders including arthritis and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, organ transplant rejection and glomerulopathies; and metabolic disorders include psoriasis, diabetes mellitus, chronic wound healing, inflammation and neurodegenerative diseases.

The host, or patient, may be from any mammalian species, e.g., primate sp., particularly human; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one hour and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g., at least about 50%, decrease in the cell burden, and may be continued until there are essentially none of the undesirable cells detected in the body.

The compounds according to the invention are preferably administered to human or nonhuman animals, more preferred to mammalian animals and especially to humans.

The compounds also find use in the specific inhibition of a signaling pathway mediated by protein kinases. Protein kinases are involved in signaling pathways for such important cellular activities as responses to extracellular signals and cell cycle checkpoints. Inhibition of specific protein kinases provided a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in the signaling mediated by protein kinases. Such conditions include those associated with defects in cell cycle regulation or in response to extracellular signals, e.g., immunological disorders, autoimmune and immunodeficiency diseases; hyperproliferative disorders, which may include psoriasis, arthritis, inflammation, endometriosis, scarring, cancer, etc. The compounds of the present invention are active in inhibiting purified kinase proteins preferably raf kinases, e.g., there is a decrease in the phosphorylation of a specific substrate in the presence of the compound. The compounds of the invention may also be useful as reagents for studying signal transduction or any of the clinical disorders listed throughout this application.

There are many disorders associated with a dysregulation of cellular proliferation. The conditions of interest include, but are not limited to, the following conditions. The subject compounds are useful in the treatment of a variety of conditions where there is proliferation and/or migration of smooth muscle cells, and/or inflammatory cells into the intimal layer of a vessel, resulting in restricted blood flow through that vessel, e.g., neointimal occlusive lesions. Occlusive vascular conditions of interest include atherosclerosis, graft coronary vascular disease after transplantation, vein graft stenosis, peri-anastomatic prothetic graft stenosis, restenosis after angioplasty or stent placement, and the like.

Diseases where there is hyperproliferation and tissue remodelling or repair or reproductive tissue, e.g., uterine, testicular and ovarian carcinomas, endometriosis, squamous and glandular epithelial carcinomas of the cervix, etc. are reduced in cell number by administration of the subject compounds. The growth and proliferation of neural cells is also of interest.

Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature.

Tumors of interest for treatment include carcinomas, e.g., colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies; e.g. neuroplastoma, gliomas, etc.; hematological malignancies, e.g., childhood acute leukaemia, non-Hodgkin's lymphomas, chronic lymphocytic leukaemia, malignant cutaneous T-cells, mycosis fungoides, non-MF cutaneous T-cell-lymphoma, lymphomatoid papulosis, T-cell rich cutaneous lymphoid hyperplasia, bullous pemphigoid, discoid lupus erythematosus, lichen planus, etc.; and the like.

Tumors of neural tissue are of particular interest, e.g., gliomas, neuromas, etc. Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltration (or invasive) ductal carcinoma (IDC) has metastasized through the wall of the duct and invaded the fatty tissue of the breast. Infiltrating (or invasive) lobular carcinoma (ILC) is similar to IDC, in that it has the potential to metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue, remodeling and repair. For example, the chronic skin inflammation of psoriasis is associated with hyperplastic epidermal keratinocycles as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemia's and lymphomas. Symptoms of allergies to environmental and food agents, as well as inflammatory bowel disease, may also be alleviated by the compounds of the invention.

Surprisingly, it has been found that benzimidazole derivatives according to invention are able to interact with signaling pathways, especially the signaling pathways described herein, preferably one or more kinase pathways as described herein, and more preferred the raf-kinase signaling pathway.

Benzimidazole derivatives according to the invention preferably show advantageous biological activity which can easily be demonstrated according to methods known in the art, for example by enzyme based assays. Suitable assays are known in the art, for example from the literature cited herein and the references cited in the literature, or can be developed and/or performed in an analogous manner thereof. In such enzyme based assays, benzimidazole derivatives according to invention show an effect, preferably a modulating and especially an inhibiting effect which is usually documented by $IC_{50}$ values in a suitable range, preferably in the micromolar range and more preferred in the nanomolar range.

In general, compounds according to the invention are to be regarded as suitable kinase-modulators and especially suitable kinase-inhibitors according to the invention if they show an effect or an activity to one or more kinases, preferably to one or more kinase is as defined herein and more preferably to one or more raf-kinases, that preferably lies, determined as $IC_{50}$-value, in the range of 100 µmol or below, preferably 10 µmol or below, more preferably in the range of 3 µmol or below, even more preferably in the range of 1 µmol or below and most preferably in the nanomolar range. Especially preferred for use according to the invention are kinase-inhibitors as defined above/below, that show an activity, determined as $IC_{50}$-value, to one or more kinases, preferably kinases as defined herein and more preferably to one or more raf-kinases, preferably including A-raf, B-raf and c-raf1 or consisting of A-raf, B-raf and c-raf1 and more preferred including c-raf1 or consisting of c-raf1, in the range of 0.5 µmol or below and especially in the range of 0.1 µmol or below. In many cases an $IC_{50}$-value at the lower end of the given ranges is advantageous and in some cases it is highly desirable that the $IC_{50}$-value is as small as possible or the $IC_{50}$-values are as small as possible, but in general $IC_{50}$-values that lie between the above given upper limits and a lower limit in the range of 0.0001 µmol, 0.001 µmol, 0.01 µmol or even above 0.1 µmol are sufficient to indicate the desired pharmaceutical activity. However, the activities measured can vary depending on the respective testing system or assay chosen.

Alternatively, the advantageous biological activity of the compounds according to the invention can easily be demonstrated in in vitro assays, such as in vitro proliferation assays or in vitro growth assays. Suitable in vitro assays are known in the art, for example from the literature cited herein and the references cited in the literature or can be performed as described below, or can be developed and/or performed in an analogous manner thereof.

As an example for an in vitro growth assay, human tumor cell lines, for example HCT116, DLD-1 or MiaPaCa, containing mutated K-ras genes can be used in standard proliferation assays, for example for anchorage dependent growth on plastic or anchorage independent growth in soft agar. Human tumor cell lines are commercially available, for example from ATCC (Rockville Md.), and can be cultured according to methods known in the art, for example in RPMI with 10% heat inactivated fetal bovine serum and 200 mM glutamine. Cell culture media, fetal bovine serum and additives are commercially available, for example from Invitrogen/Gibco/BRL (Karlsruhe, Germany) and/or QRH Biosciences (Lenexa, Kans.). In a standard proliferation assay for anchorage dependent growth, $3 \times 10^3$ cells can be seeded into 96-well tissue culture plates and allowed to attach, for example overnight at 37° C. in a 5% $CO_2$ incubator. Compounds can be titrated in media in dilution series and added to 96 well cell cultures. Cells are allowed to grow, for example for 1 to 5 days, typically with a feeding of fresh compound containing media at about half of the time of the growing period, for example on day 3, if the cells are allowed to grow 5 days. Proliferation can be monitored by methods known in the art, such as measuring metabolic activity, for example with standard XTT calorimetric assay (Boehringer Mannheim) measured by standard ELISA plate reader at OD 490/560, by measuring $^3$H-thymidine incorporation into DNA following an 8 h culture with 1 µCu $^3$H-thymidine, harvesting the cells onto glass fiber mats using a cell harvester and measuring $^3$H-thymidine incorporation by liquid scintillation counting, or by staining techniques, such as crystal violet staining. Other suitable cellular assay systems are known in the art.

Alternatively, for anchorage independent cell growth, cells can be plated at $1 \times 10^3$ to $3 \times 10^3$ in 0.4% Seaplaque agarose in RPMI complete media, overlaying a bottom layer containing only 0.64% agar in RPMI complete media, for example in 24-well tissue culture plates. Complete media plus dilution series of compounds can be added to wells and incubated, for example at 37° C. in a 5% $CO_2$ incubator for a sufficient time, for example 10-14 days, preferably with repeated feedings of fresh media containing compound, typically at 3-4 day intervals. Colony formation and total cell mass can be monitored, average colony size and number of colonies can be quantitated according to methods known in the art, for example using image capture technology and image analysis software. Image capture technology and image analysis software, such as Image Pro Plus or media Cybernetics.

As discussed herein, these signaling pathways are relevant for various disorders. Accordingly, by interacting with one or more of said signaling pathways, benzimidazole derivatives are useful in the prevention and/or the treatment of disorders that are dependent from said signaling pathways.

The compounds according to the invention are preferably kinase modulators and more preferably kinase inhibitors. According to the invention, kinases include, but are not limited to one or more Raf-kinases, one or more Tie-kinases, one or more VEGFR-kinases, one or more PDGFR-kinases, p38-kinase and/or SAPK2alpha.

Preferably, kinases according to the invention are selected from Serine/Threonine kinases (STK) and Receptor-Tyrosine kinases (RTK).

Serine/Threonine kinases according to the invention are preferably selected from one or more Raf-kinases, p38-kinase and SAPK2alpha.

Receptor-Tyrosine kinases according to the invention are preferably selected from one or more PDGFR-kinases, one or more VEGFR-kinases and one or more Tie-kinases.

Preferably, kinases according to the invention are selected from one or more Raf-kinases, one or more Tie-kinases, one or more VEGFR-kinases, one or more PDGFR-kinases, p38-kinase and SAPK2alpha.

Raf-kinases in this respect are respect preferably include or consist of A-Raf, B-Raf and c-Raf1.

Tie-kinases in this respect preferably include or consist of Tie-2 kinase.

VEGFR-kinases in this respect preferably include or consist of VEGFR-2 kinase.

Preferred signalling pathways according to the invention are signalling pathways, wherein one or more of the kinases given above are involved.

Due to the kinase modulating or inhibiting properties of the compounds according to the invention, the compounds according to the invention preferably interact with one or more signalling pathways which are preferably cell signalling pathways, preferably by downregulating or inhibiting said signaling pathways. Examples for such signalling pathways include, but are not limited to the raf-kinase pathway, the Tie-kinase pathway, the VEGFR-kinase pathway, the PDGFR-kinase pathway, the p38-kinase pathway, the SAPK2alpha pathway and/or the Ras-pathway.

Modulation of the raf-kinase pathway plays an important role in various cancerous and noncancerous disorders, preferably cancerous disorders, such as dermatological tumors, haematological tumors, sarcomas, squamous cell cancer, gastric cancer, head cancer, neck cancer, oesophageal cancer, lymphoma, ovary cancer, uterine cancer and/or prostate cancer. Modulation of the raf-kinase pathway plays a even more important role in various cancer types which show a constitutive activation of the raf-kinase dependent signalling pathway, such as melanoma, colorectal cancer, lung cancer, brain cancer, pancreatic cancer, breast cancer, gynecological cancer, ovarian cancer, thyroid cancer, chronic leukaemia and acute leukaemia, bladder cancer, hepatic cancer and/or renal cancer. Modulation of the raf-kinase pathway plays also an important role in infection diseases, preferably the infection diseases as mentioned above/below and especially in *Helicobacter pylori* infections, such as *Helicobacter pylori* infection during peptic ulcer disease.

One or more of the signalling pathways mentioned above/below and especially the VEGFR-kinase pathway plays an important role in angiogenesis. Accordingly, due to the kinase modulating or inhibiting properties of the compounds according to the invention, the compounds according to the invention are suitable for the prophylaxis and/or treatment of pathological processes or disorders caused, mediated and/or propagated by angiogenesis, for example by inducing anti-angiogenesis. Pathological processes or disorders caused, mediated and/or propagated by angiogenesis include, but are not limited to tumors, especially solid tumors, arthritis, especially rheumatic or rheumatoid arthritis, diabetic retinopathy, psoriasis, restenosis; fibrotic disorders; mesangial cell proliferative disorders, diabetic nephropathy, malignant nephrosclerosis, thrombotic microangiopathy syndromes, organ transplant rejection, glomerulopathies, metabolic disorders, inflammation and neurodegenerative diseases, and especially solid tumors, rheumatic arthritis, diabetic retinopathy and psoriasis.

Modulation of the p38-signalling pathway plays an important role in various cancerous and although in various noncancerous disorders, such as fibrosis, atherosclerosis, restenosis, vascular disease, cardiovascular disease, inflammation, renal disease and/or angiogenesis, and especially noncancerous disorders such as rheumatoid arthritis, inflammation, autoimmune disease, chronic obstructive pulmonary disease, asthma and/or inflammatory bowel disease.

Modulation of the PDGF-signalling pathway plays an important role in various cancerous and although in various noncancerous disorders, such as rheumatoid arthritis, inflammation, autoimmune disease, chronic obstructive pulmonary disease, asthma and/or inflammatory bowel disease, and especially noncancerous disorders such as fibrosis, atherosclerosis, restenosis, vascular disease, cardiovascular disease, inflammation, renal disease and/or angiogenesis.

As discussed herein, these signaling pathways are relevant for various disorders. Accordingly, by interacting with one or more of said signaling pathways, benzimidazole derivatives are useful in the prevention and/or the treatment of disorders that are dependent from said signaling pathways.

Subject of the present invention are therefore benzimidazole derivatives according to the invention as promoters or inhibitors, preferably as inhibitors, of the signaling pathways described herein. Preferred subject of the invention are therefore benzimidazole derivatives according to the invention as promoters or inhibitors, preferably as inhibitors, of one or more kinase pathways, preferably one or more kinase pathways as defined herein and more preferred of the raf-kinase pathway. More preferred subject of the invention are therefore benzimidazole derivatives according to the invention as promoters or inhibitors, preferably as inhibitors of the raf-kinase. Even more preferred subject of the invention are benzimidazole derivatives according to the invention as promoters or inhibitors, preferably as inhibitors of one or more raf-kinases, selected from the group consisting of A-raf, B-raf and c-raf1. Especially preferred subject of the invention are benzimidazole derivatives according to the invention as promoters or inhibitors, preferably as inhibitors of c-raf1.

Thus, subject of the present invention are benzimidazole derivatives according to the invention as medicaments. Subject of the present invention are benzimidazole derivatives according to the invention as medicament active ingredients. Further subject of the present invention is the use of one or more benzimidazole derivatives according to the invention as a pharmaceutical. Further subject of the present invention is the use of one or more benzimidazole derivatives according to the invention in the treatment and/or the prophylaxis of disorders, preferably the disorders described herein, more preferred disorders that are caused, mediated and/or propagated by signalling pathways discussed herein, even more preferred disorders that are caused, mediated and/or propagated by raf-kinases and especially disorders that are caused, mediated and/or propagated by raf-kinases, selected from the group consisting of A-raf, B-raf and c-raf1.

Usually, the disorders discussed herein are divided into two groups, hyperproliferative and non hyperproliferative disorders.

In this context, infections or infectious diseases, psoriasis, arthritis, inflammation, endometriosis, scarring, begnin prostatic hyperplasia, immunological diseases, autoimmune diseases and immunodeficiency diseases are to be regarded as noncancerous disorders, of which infections, arthritis, inflammation, immunological diseases, autoimmune diseases and immunodeficiency diseases are usually regarded as non hyperproliferative disorders.

In this context, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynecological cancer, thyroid cancer, lymphoma, chronic leukaemia and acute leukaemia are to be regarded as cancerous disorders, all of which are usually regarded as hyperproliferative disorders.

Especially cancerous cell growth and especially cancerous cell growth mediated by raf-kinase is a disorder which is a target of the present invention.

Subject of the present invention therefore are benzimidazole derivatives according to the invention as medicaments and/or medicament active ingredients in the treatment and/or the prophylaxis of said disorders and the use of benzimidazole derivatives according to the invention for the manufacture of a pharmaceutical for the treatment and/or the prophylaxis of said disorders as well as a method of treatment of said disorders, comprising administering one or more benzimidazole derivatives according to the invention to a patient in need of such an administration.

Accordingly, subject of the present invention are pharmaceutical compositions that contain one or more benzimidazole derivatives according to the invention. Subject of the present invention are especially pharmaceutical compositions that contain one or more benzimidazole derivatives according to the invention and one or more additional compounds (other than the compounds of the instant invention), preferably selected from the group consisting of physiologically acceptable excipients, auxiliaries, adjuvants, carriers and pharmaceutically active ingredients other than the compounds according to the invention.

Accordingly, subject of the present invention is a process for the manufacture of a pharmaceutical composition, wherein one or more benzimidazole derivatives according to the invention and one or more compounds (other than the compounds of the instant invention), preferably selected from the group consisting of carriers, excipients, auxiliaries, adjuvants and pharmaceutically active ingredients other than the compounds according to the invention.

Accordingly, the use of the compounds according to the invention in the treatment of hyperproliferative disorders is a subject of the instant invention.

Accordingly, the use of the compounds according to the invention for producing a medicament for the treatment of hyperproliferative disorders is a subject of the instant invention.

Especially preferred subject of the invention as a method for the treatment of cancerous cell growth mediated by one or more kinases and especially cancerous cell growth mediated by one or more raf-kinases.

Above and below, all temperatures are given in ° C. In the examples below, "conventional work-up" means that the organic phase is washed with saturated NaHCO$_3$ solution, if desired with water and saturated NaCl solution, the phases are separated, the organic phase is dried over sodium sulfate and evaporated, and the product is purified by chromatography on silica gel, by preparative HPLC and/or by crystallization.

The present invention relates to benzimidazole derivatives of formula I, the use of the compounds of formula I as inhibitors of raf-kinase, the use of the compounds of formula I for the manufacture of a pharmaceutical composition and a method of treatment, comprising administering said pharmaceutical composition to a patient.

EXAMPLES

Synthesis of the Carboxylic Acid Building Blocks 3-(2-Methylcarbamoyl-4-pyridinyloxy)benzoic acid 4 and 4-(2-Methylcarbamoyl-4-pyridinyloxy)benzoic acid 10

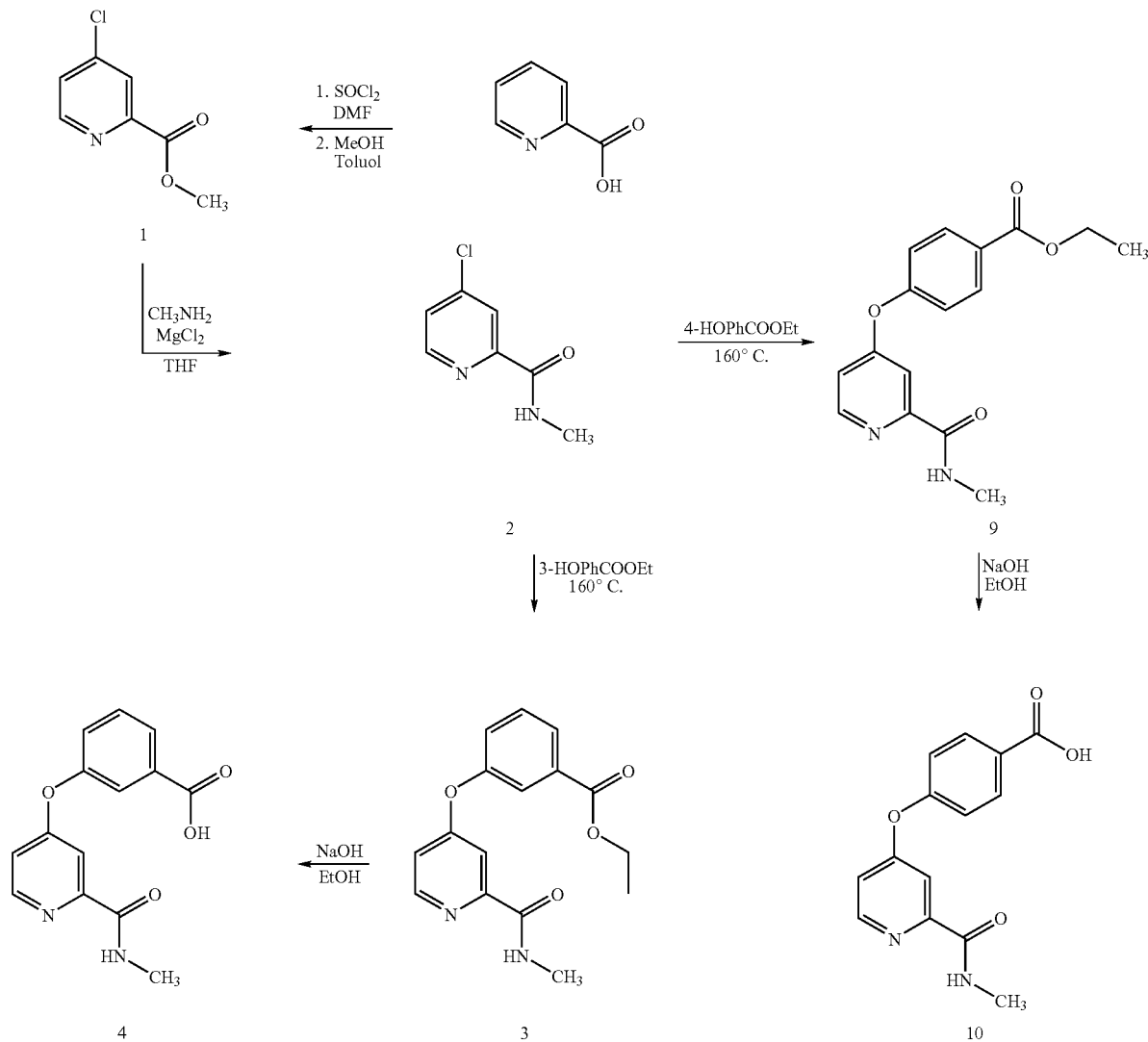

60 ml Thionylchloride are heated to a temperature of 45° C. under a nitrogen atmosphere and 1.83 ml dimethylformamide is added slowly. 20 g Pyridin-2-carboxylic acid is added to the solution in portions, the reaction mixture is stirred another 15 min at 45° C. and then heated to 80° C. for 24 hrs. The reaction mixture is evaporated and the resulting residue treated with dry toluene as a carrier and then evaporated. This procedure is repeated several times. The resulting oil is dissolved in toluene, cooled to 0° C., slowly treated with methanol and stirred for one hour. The resulting precipitate is filtered by suction, washed with toluene and recrystallised from acetone.

Yield: 15 g (44%) 1, colourless crystals 13 g (62.5 mmol) 1 are dissolved together with 2.98 g (31.24 mmol) dry magnesiumchloride in THF. After 5 min 110 ml methylamin-solution (2M in THF) are added dropwise within 10 min and the suspension stirred for 2 h at room temperature. 120 ml water and 63 mL 1M HCl-solution are added and the mixture is extracted three times with ethyl acetate. The combined organic phases are washed with brine, dried with $Na_2SO_4$, filtered and evaporated.

Yield: 10.5 g (98.5%) 2, colourless oil.

0.5 g (2.93 mmol) 2 are heated to a temperature of 160° C. together with 0.97 g (5.86 mmol) 4-hydroxy benzoic acid, ethyl ester, for 18 hrs in an argon atmosphere. The reaction mixture is cooled down, diluted with 50 ml ethyl acetate, washed consecutively 4× with 50 ml 1N NaOH— solution and twice with 30 ml water. The organic phase is separated, dried over $Na_2SO_4$, filtered and evaporated. The thus obtained crude product is used in the next step of the synthesis without further purification.

Yield: 0.68 g (66%) 3.

0.68 g (1.92 mmol) 3 are dissolved in methanol (5 ml), treated with 1N NaOH-solution (8 ml) and stirred for 2 hrs at room temperature. The reaction mixture is concentrated and extracted with ethyl acetate (2×10 ml). The water phase is made acidic with 6 ml 1N HCl-solution (pH=4), whereby an oil separates which crystallises when allowed to stand for a longer period. The thus obtained precipitate is filtered by suction and dried.

Yield: 0.402 g (77%) 4, colourless solid 5 g (29.31 mmol) 2 and 9.84 g (58.62 mmol) 4-hydroxybenzoic acid ethylester are heated to 160° C. for 36 hrs in an argon atmosphere. The reaction mixture is cooled down, the brown syrup is treated with 50 ml ethyl acetate and washed 4× with 50 ml 1N NaOH and 2× with 50 ml water. The organic phase is dried over $Na_2SO_4$ filtered and evaporated. The residue is purified by chromatography (650 g silica gel, eluent: ethyl acetate).

Yield: 6 g (64%) 9, colourless crystals 0.4 g (1.33 mmol) 9 are dissolved in 4 ml methanol, treated with 6 ml 1N NaOH-solution and stirred for 1 h at room temperature. The reaction mixture is made acidic (pH=5) with 1N HCl-solution and concentrated until a precipitate is obtained. The precipitate is separated by filtration by suction and dried.

Yield: 310 mg (85%) 10, colourless crystals

Synthesis of the Amino Benzimidazole Building Blocks

5-Trifluoromethyl-1-benzimidazole-2-ylamine

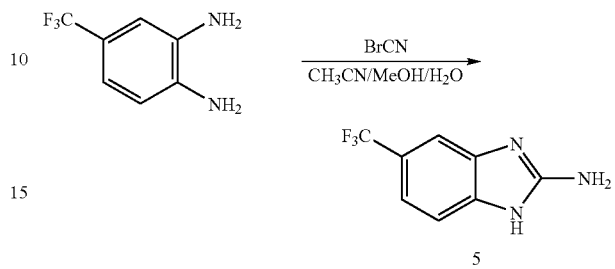

1.32 g (12.49 mmol) BrCN are dissolved in 2.5 ml acetonitrile and treated with 24 ml water. 2 g (11.35 mmol) 3,4-diamino benzotrifluoride, dissolved in 24 ml methanol, are added dropwise within 1 hour. After three hours of stirring at room temperature, the reaction mixture is concentrated and the aqueous phase is extracted twice with ethyl acetate. The combined organic phases are extracted once with water. The pH value of the obtained aqueous phase is adjusted to pH=8 with saturated $NaHCO_3$-solution and extracted twice with ethyl acetate. The combined organic phases are dried, filtered and evaporated.

Yield: 1.95 g (84%) of 5, pale beige crystals

5-Chloro-6-trifluoromethyl-1H-benzoimidazole-2-ylamine

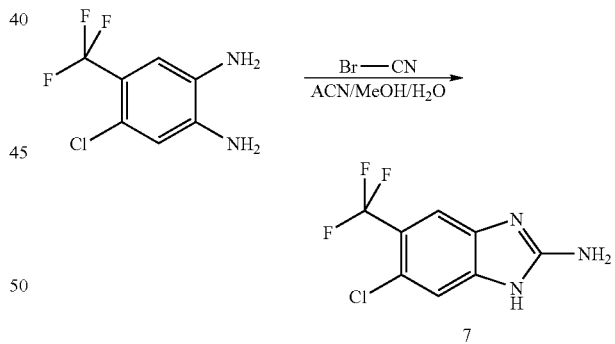

318 mg (3 mmol) BrCN are dissolved in 0.6 ml acetonitrile and treated with 6 ml water. To this solution, 575 mg (2.73 mmol) 5-chloro-6-trifluoromethyl-benzene-1,2-diamine, dissolved in 6 ml methanol, are added dropwise within 30 min. After 2 hrs of stirring at room temperature, the reaction mixture is concentrated and the water solution extracted 2× with ethyl acetate. The combined organic phases where re-extracted 1× with water. The combined water phases where made alkaline (pH=8) with saturated $NaHCO_3$-solution and extracted 2× with ethyl acetate. The combined organic phases where dried, filtered and evaporated.

Yield: 611 mg (95%) 7, red solid

Synthesis of the Amides

4-[3-(5-Trifluoromethyl-1H-benzimidazol-2-yl)carbamoyl))phenoxy]pyridine-2-carboxylic acid, methyl amide

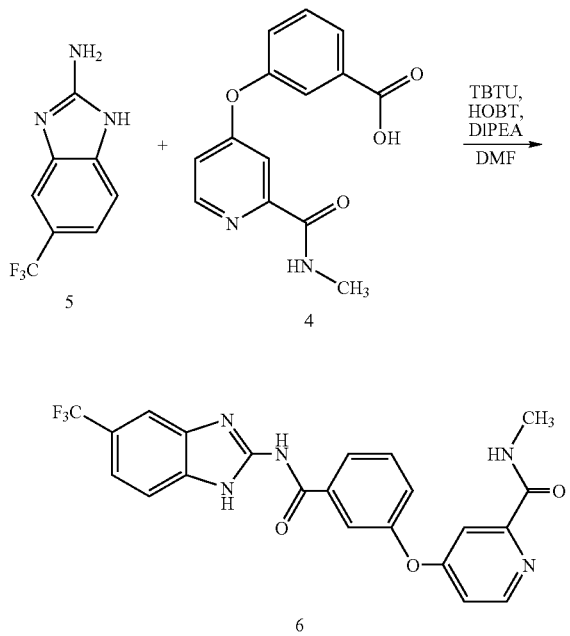

48.8 mg (0.179 mmol) 4, 32.8 mg (0.163 mmol) 5, 68 mg (0.212 mmol) TBTU and 7.5 mg (0.049 mmol) HOBT are dissolved in 1.8 ml DMF and treated with 0.11 ml (0.652 mmol) DIPEA. After three hours of stirring at room temperature, approx. 2 ml water are added to the reaction mixture, whereby a precipitate is obtained. The precipitate is filtered by suction, washed with water and digested with little methanol.

Yield: 27.5 mg (37%) 6, colourless solid

4-[3-(5-Chloro-6-trifluoromethyl-1H-benzoimidazole-2-yl)carbamoyl))phenoxy]pyridine-2-carboxylic acid methyl amide

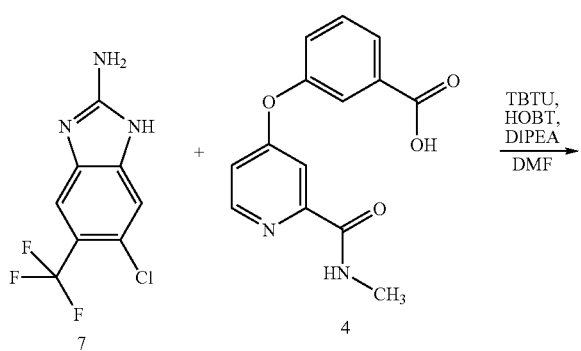

-continued

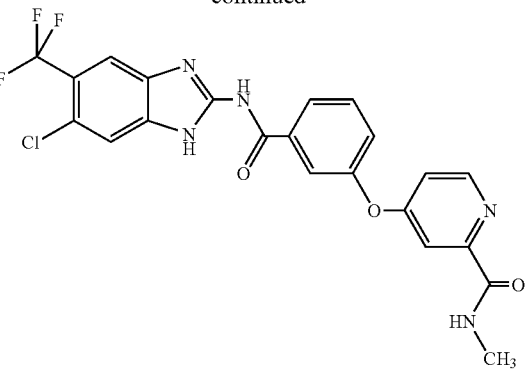

38.9 mg (0.143 mmol) 4, 31.9 mg (0.13 mmol) 7, 54.3 mg (0.169 mmol) TBTU and 6 mg (0.039 mmol) HOBT are dissolved in 0.8 ml DMF and treated with 0.09 ml (0.52 mmol) DIPEA. After 2 h of stirring at room temperature, the reaction mixture is added dropwise to 2 ml of water, resulting in a precipitate. The precipitate is separated by filtration by suction and recrystallised from little methanol.

Yield: 13 mg (20%) 8, colourless solid

The compounds (1) to (78) as described above can preferably be produced according to the procedures described herein or in an analogous manner thereof.

Example A

Injection Vials

A solution of 100 g of an active compound of the formula I and 5 g of disodium hydrogenphosphate is adjusted to pH 6.5 in 3 l of double-distilled water using 2N hydrochloric acid, sterile-filtered, dispensed into injection vials, lyophilized under sterile conditions and aseptically sealed. Each injection vial contains 5 mg of active compound.

Example B

Suppositories

A mixture of 20 g of an active compound of the formula I is fused with 100 g of soya lecithin and 1400 g of cocoa butter, poured into moulds and allowed to cool. Each suppository contains 20 mg of active compound.

Example C

Solution

A solution of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. It is adjusted to pH 6.8, made up to 1 l and sterilized by irradiation. This solution can be used in the form of eye drops.

Example D

Ointment 500 mg of an active compound of the formula I is mixed with 99.5 g of petroleum jelly under aseptic conditions.

Example E

Tablets

A mixture of 1 kg of active compound of the formula I, 4 kg of lactose, 1.2 kg of potato starch, 0.2 kg of talc and 0.1 kg of magnesium stearate is compressed to give tablets in a customary manner such that each tablet contains 10 mg of active compound.

Example F

Coated Tablets

Analogously to Example E, tablets are pressed and are then coated in a customary manner using a coating of sucrose, potato starch, talc, tragacanth and colourant.

Example G

Capsules 2 kg of active compound of the formula I are dispensed into hard gelatin capsules in a customary manner such that each capsule contains 20 mg of the active compound.

Example H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

The invention claimed is:

1. A compound or compounds of formula I

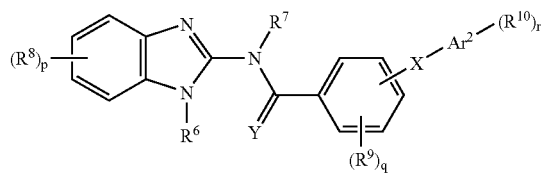

I wherein,
$Ar^2$ is pyridinyl,
$R^6$, $R^7$ independently from one another, are H or unbranched or branched alkyl comprising 1 to 6 carbon atoms, optionally substituted by one or more Hal atoms,
$R^8$, $R^9$ independently from one another, are selected from the group consisting of A, H, Hal and unbranched or branched alkyl comprising 1 to 6 carbon atoms, optionally substituted by one or more Hal atoms,
$R^{10}$ is selected from the group consisting of H, alkyl comprising 1 to 4 carbon atoms and $(CH_2)_n CONR^{11}R^{12}$,
$R^{11}$, $R^{12}$ independently from one another, are selected from the group consisting of H, Hal and branched or unbranched alkyl comprising 1 to 6 carbon atoms, optionally substituted by one or more Hal atoms,
n is 0, 1, 2, 3, 4, or 5,
X is O
Y is O
p is 0, 1, 2, 3, 4 or 5,
q is 0, 1, 2, 3 or 4,
r is 0, 1, 2 or 3,
and
Hal is selected from the group consisting of F, Cl, Br and I,
or tautomeric forms, salts, stereoisomers or mixtures thereof in all ratios.

2. The compound or compounds according to claim 1, wherein
$R^6$, $R^7$ independently from one another, are H or are selected from the group consisting of methyl, ethyl, trifluoro methyl, pentafluoro ethyl, isopropyl, and tert.-butyl,
$R^8$, $R^9$ independently from one another, are H or Hal or are selected from the group consisting of methyl, ethyl, trifluoro methyl, pentafluoro ethyl, isopropyl, and tert.-butyl, and
Hal is selected from the group consisting of F, Cl and Br,
or tautomeric forms, salts, stereoisomers or mixtures thereof in all ratios.

3. The compound or compounds according to claim 1, selected from the group consisting of the compounds of formulae Ia, Ib, Ic and Id,

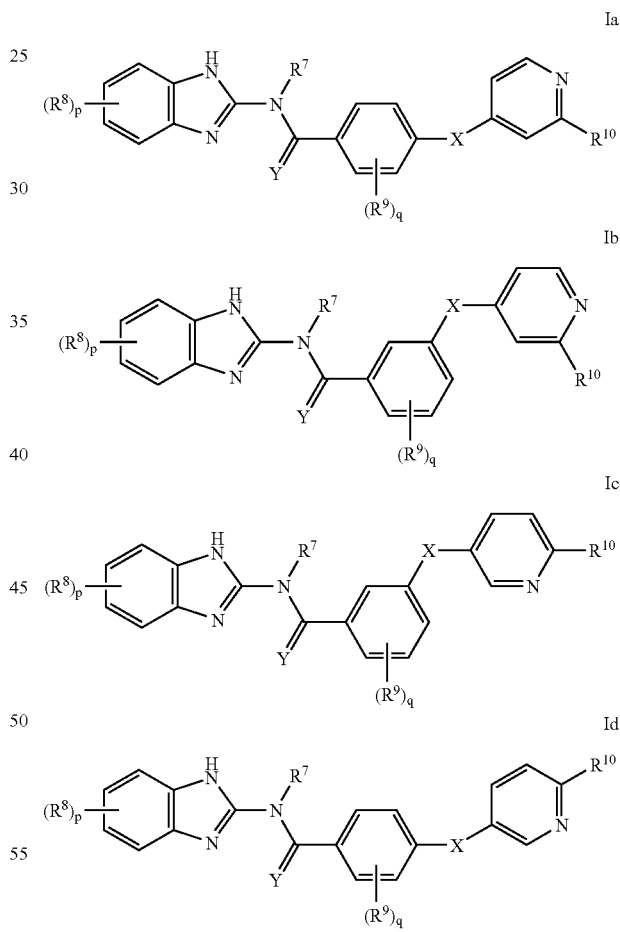

wherein
$R^7$, $R^8$, p, X, Y, $R^9$, q and $R^{10}$ are as defined in claim 1, and tautomeric forms, salts, stereoisomers or mixtures thereof in all ratios.

4. The compound or compounds according to claim 1, having formula A—NH—CO—B, wherein A— and —B are selected from the group consisting of,

| | A- | ,-B |
|---|---|---|
| (1) | 2-methylbenzimidazole | 4-(pyridin-4-yloxy)phenyl |
| (2) | 2-methylbenzimidazole | 3-(pyridin-4-yloxy)phenyl |
| (3) | 2-methylbenzimidazole | 3-(pyridin-3-yloxy)phenyl |
| (4) | 2-methylbenzimidazole | 4-(pyridin-3-yloxy)phenyl |
| (5) | 2-methylbenzimidazole | 4-(3-methylphenoxy)-N-methylpyridine-2-carboxamide |
| (6) | 2-methylbenzimidazole | 4-(4-methylphenoxy)-N-methylpyridine-2-carboxamide |
| (7) | 5-chloro-2-methylbenzimidazole | 4-(pyridin-4-yloxy)phenyl |
| (8) | 5-chloro-2-methylbenzimidazole | 3-(pyridin-4-yloxy)phenyl |
| (9) | 5-chloro-2-methylbenzimidazole | 3-(pyridin-3-yloxy)phenyl |
| (10) | 5-chloro-2-methylbenzimidazole | 4-(pyridin-3-yloxy)phenyl |

-continued
| | A- | ,-B |
|---|---|---|
| (11) | 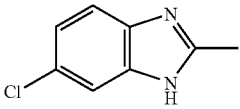 | 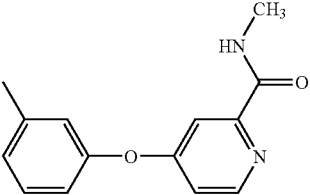 |
| (12) | 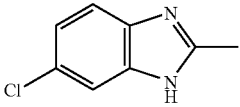 | 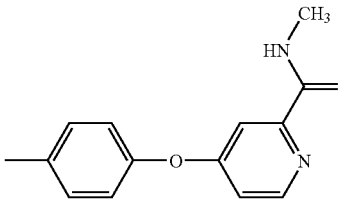 |
| (13) | 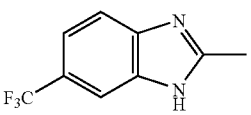 | 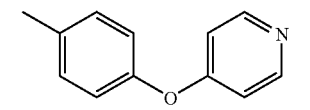 |
| (14) | 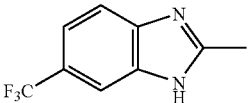 | 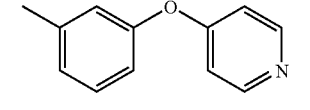 |
| (15) | 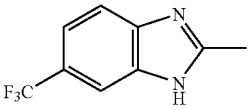 | 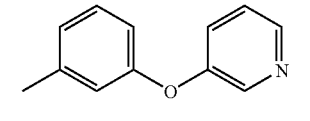 |
| (16) | 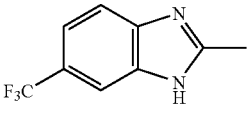 | 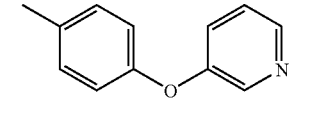 |
| (17) | 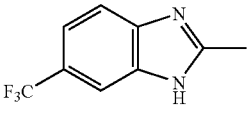 | 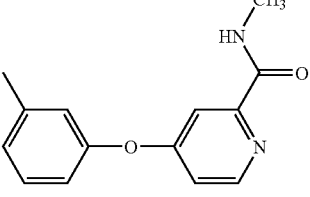 |
| (18) | 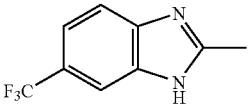 | 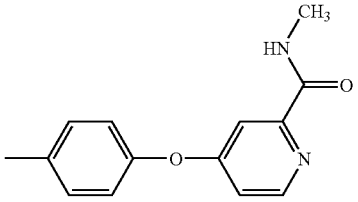 |
| (19) | 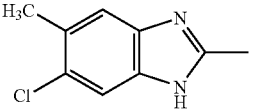 | 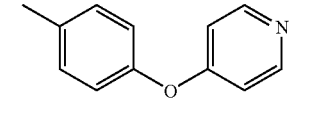 |

-continued
| | A- | ,-B |
|---|---|---|
| (20) | 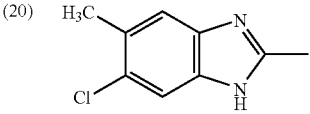 | 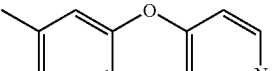 |
| (21) | 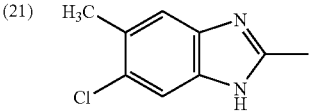 |  |
| (22) | 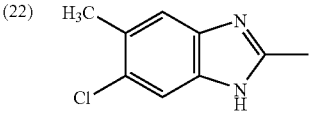 |  |
| (23) | 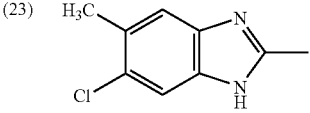 | 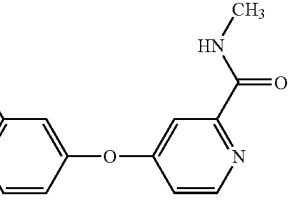 |
| (24) | 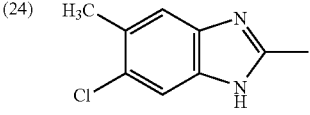 | 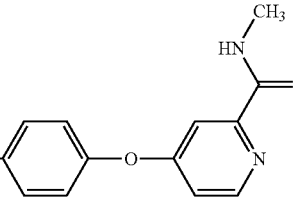 |
| (25) | 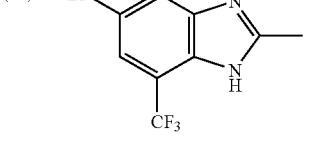 | 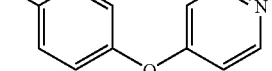 |
| (26) | 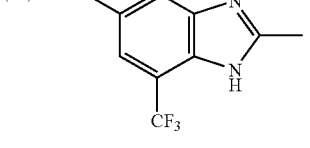 | 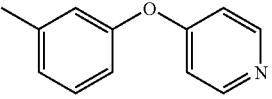 |
| (27) | 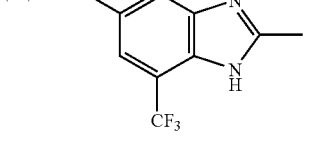 | 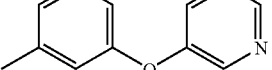 |
| (28) | 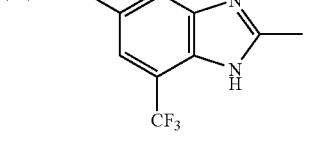 | 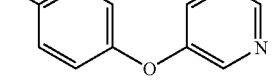 |

-continued

| A- | ,-B |
|---|---|
| (29) 5-bromo-7-(trifluoromethyl)-2-methyl-1H-benzimidazole | N-methyl-4-(3-methylphenoxy)pyridine-2-carboxamide |
| (30) 5-bromo-7-(trifluoromethyl)-2-methyl-1H-benzimidazole | N-methyl-4-(4-methylphenoxy)pyridine-2-carboxamide |
| (31) 5-chloro-7-(trifluoromethyl)-2-methyl-1H-benzimidazole | 4-(4-methylphenoxy)pyridine |
| (32) 5-chloro-7-(trifluoromethyl)-2-methyl-1H-benzimidazole | 4-(3-methylphenoxy)pyridine |
| (33) 5-chloro-7-(trifluoromethyl)-2-methyl-1H-benzimidazole | 3-(3-methylphenoxy)pyridine |
| (34) 5-chloro-7-(trifluoromethyl)-2-methyl-1H-benzimidazole | 3-(4-methylphenoxy)pyridine |
| (35) 5-chloro-7-(trifluoromethyl)-2-methyl-1H-benzimidazole | N-methyl-4-(3-methylphenoxy)pyridine-2-carboxamide |
| (36) 5-chloro-7-(trifluoromethyl)-2-methyl-1H-benzimidazole | N-methyl-4-(4-methylphenoxy)pyridine-2-carboxamide |

-continued
| | A- | ,-B |
|---|---|---|
| (37) | 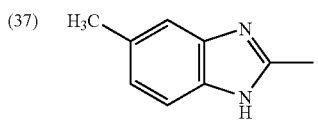 | 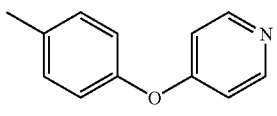 |
| (38) | 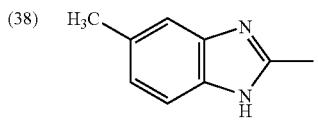 | 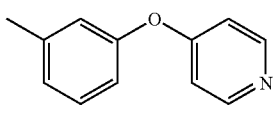 |
| (39) | 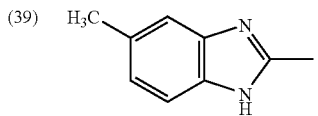 | 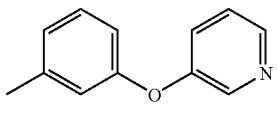 |
| (40) | 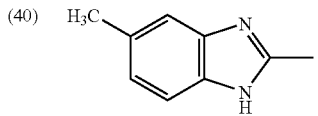 | 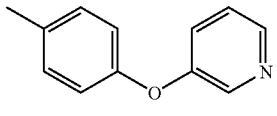 |
| (41) | 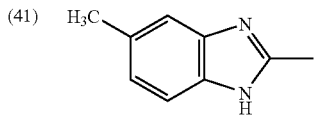 |  |
| (42) | 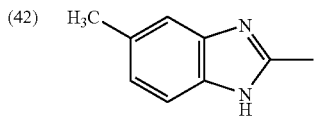 |  |
| (43) | 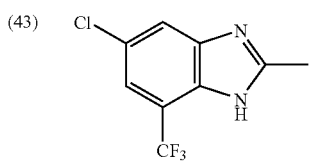 | 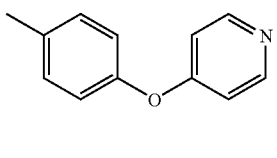 |
| (44) | 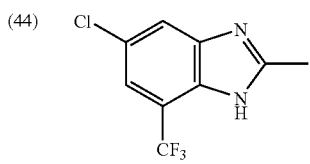 | 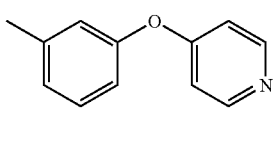 |
| (45) | 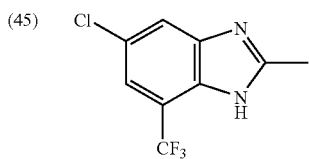 | 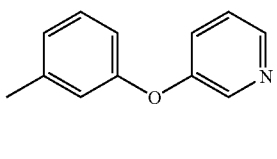 |

-continued
| | A- | ,-B |
|---|---|---|
| (46) | 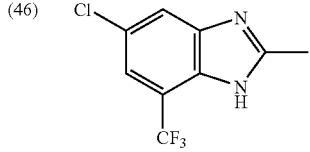 | 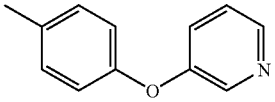 |
| (47) | 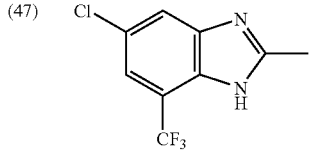 | 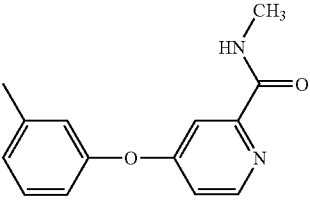 |
| (48) | 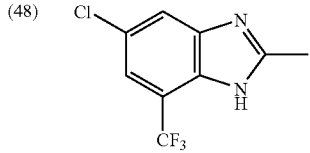 | 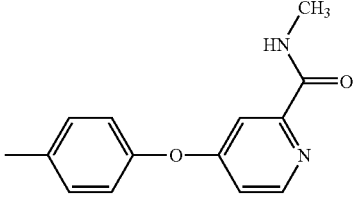 |
| (49) | 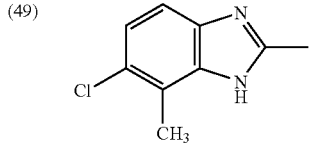 | 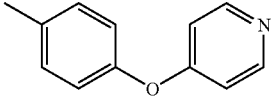 |
| (50) | 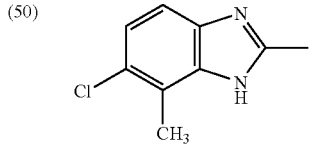 | 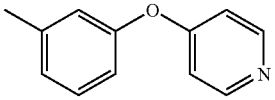 |
| (51) | 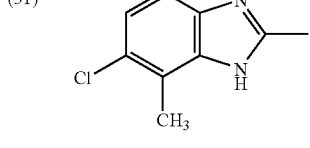 | 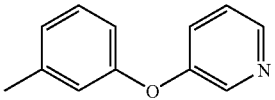 |
| (52) | 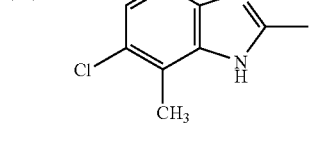 | 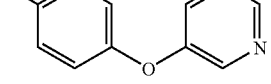 |
| (53) | 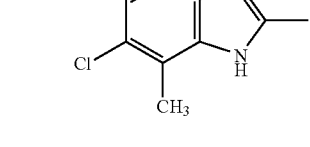 | 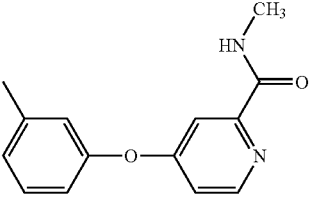 |

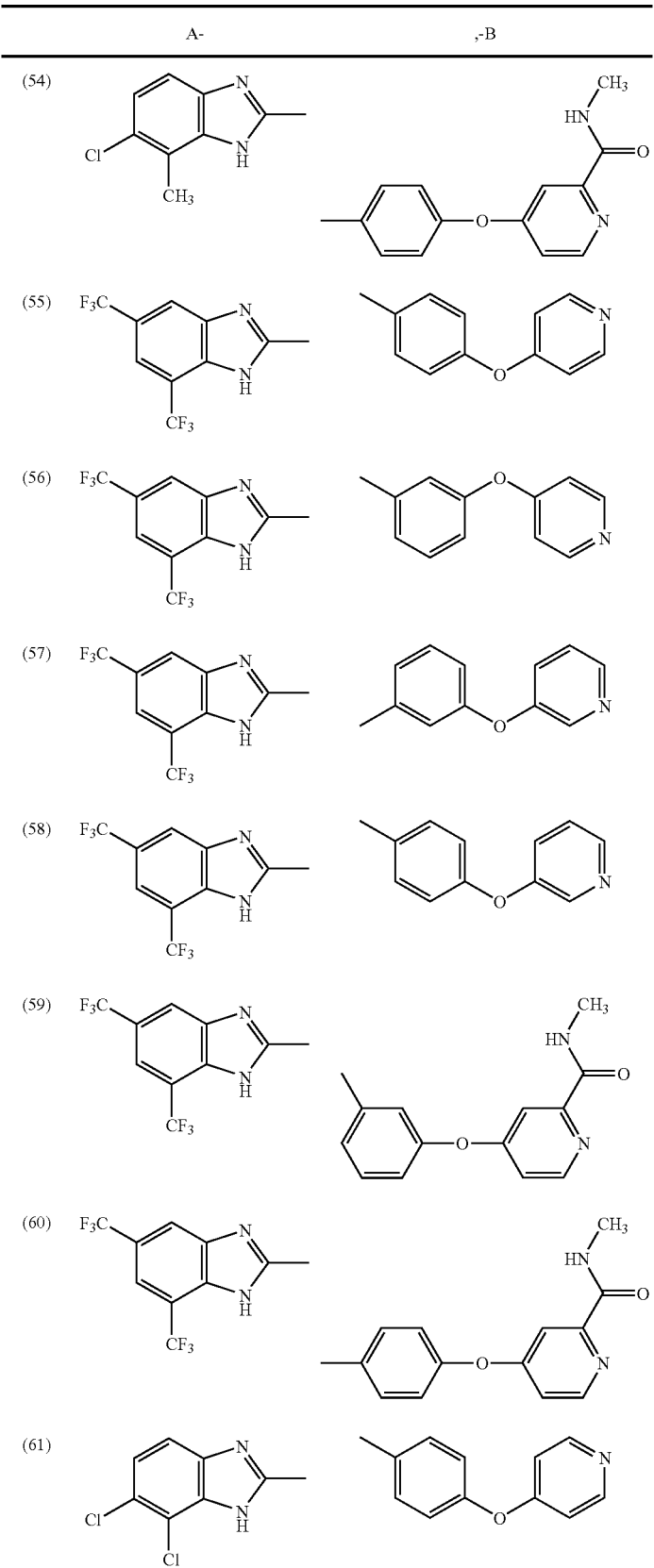

-continued

| | A- | ,-B |
|---|---|---|
| (62) | 4,5-dichloro-2-methyl-1H-benzimidazole | 3-methylphenyl 4-pyridyl ether |
| (63) | 4,5-dichloro-2-methyl-1H-benzimidazole | 3-methylphenyl 3-pyridyl ether |
| (64) | 4,5-dichloro-2-methyl-1H-benzimidazole | 4-methylphenyl 3-pyridyl ether |
| (65) | 4,5-dichloro-2-methyl-1H-benzimidazole | 4-(3-methylphenoxy)-N-methylpyridine-2-carboxamide |
| (66) | 4,5-dichloro-2-methyl-1H-benzimidazole | 4-(4-methylphenoxy)-N-methylpyridine-2-carboxamide |
| (67) | 2,6-dimethyl-1H-benzimidazole | 4-methylphenyl 4-pyridyl ether |
| (68) | 2,6-dimethyl-1H-benzimidazole | 3-methylphenyl 4-pyridyl ether |
| (69) | 2,6-dimethyl-1H-benzimidazole | 3-methylphenyl 3-pyridyl ether |
| (70) | 2,6-dimethyl-1H-benzimidazole | 4-methylphenyl 3-pyridyl ether |

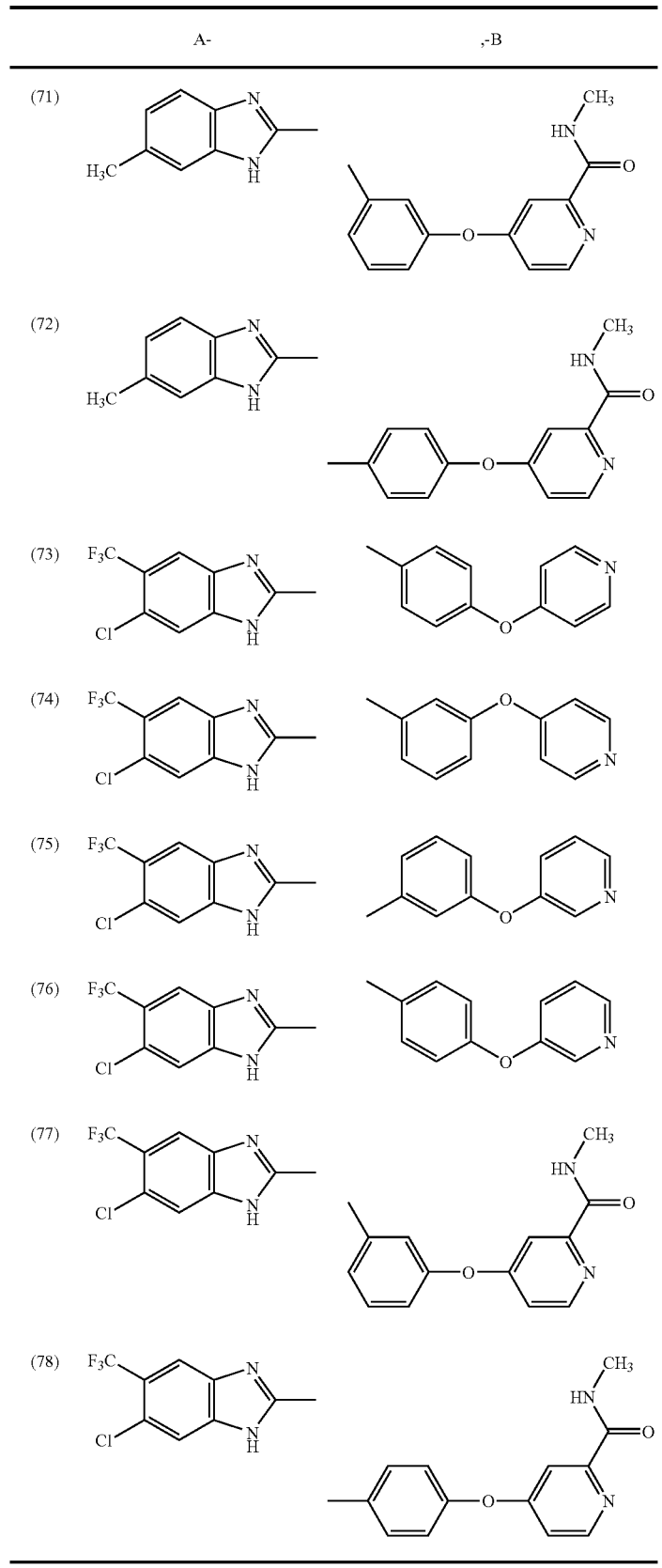

or tautomeric forms, salts, stereoisomers or mixtures thereof in all ratios.

5. A pharmaceutical composition, comprising one or more of the compound or compounds according to claim 1, or tautomeric forms, salts, stereoisomers or mixtures thereof in all ratios, in a pharmaceutical composition.

6. The pharmaceutical composition according to claim 5, characterized in that it contains one or more additional compounds, selected from the group consisting of physiologically acceptable excipients, auxiliaries, adjuvants, carriers and pharmaceutical active ingredients.

7. A process for the manufacture of a pharmaceutical composition, comprising one or more of the compound or compounds according to claim 1, or tautomeric forms, salts, stereoisomers or mixtures thereof in all ratios, and one or more compound or compounds, selected from the group consisting of carriers, excipients, auxiliaries and pharmaceutical active ingredients other than the compound or compounds according to claim 1, is processed by mechanical means into a pharmaceutical composition that is suitable as dosage form for application and/or administration to a patient.

8. A method comprising administering to a patient the compound or compounds according to claim 1, or tautomeric forms, salts, stereoisomers or mixtures thereof in all ratios, as a pharmaceutical composition.

9. A method for producing the compound or compounds of claim 1, or tautomeric forms, salts, stereoisomers or mixtures thereof in all ratios, comprising that a) a compound of formula II

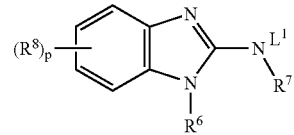

II wherein
$L^1$ is H or a metal ion, and $R^6$, $R^7$, $R^8$ and p are as defined in claim 1, is reacted
b) with a compound of formula III,

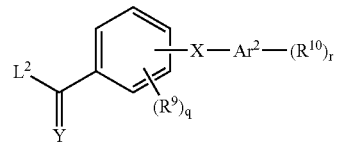

III wherein
$L^2$ is Cl, Br, I, OH, an esterified OH-group or a diazonium moiety, and Y, $R^9$, q, X, $Ar^2$, $R^{10}$ and r are as defined in claim 1,
and optionally
c) isolating and/or treating the compound or compounds of claim 1 obtained by said reaction with an acid, to obtain the salt thereof.

* * * * *